US009066976B2

(12) United States Patent
Im et al.

(10) Patent No.: US 9,066,976 B2
(45) Date of Patent: Jun. 30, 2015

(54) METHOD FOR THERAPEUTIC ANGIOGENESIS

(75) Inventors: Dong-Soo Im, Daejeon (KR); Cho-Rok Jung, Daejeon (KR); Kyung-Sun Hwang, Daejeon (KR); Jung Hwa Lim, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 173 days.

(21) Appl. No.: 13/215,085

(22) Filed: Aug. 22, 2011

(65) Prior Publication Data

US 2012/0107297 A1       May 3, 2012

Related U.S. Application Data

(63) Continuation-in-part of application No. 12/789,670, filed on May 28, 2010, now abandoned, which is a continuation of application No. 12/093,093, filed as application No. PCT/KR2006/004749 on Nov. 13, 2006, now abandoned.

(30) Foreign Application Priority Data

Nov. 11, 2005   (KR) .................. 10-2005-0108014

(51) Int. Cl.
*A61K 48/00*     (2006.01)
*C07K 14/00*     (2006.01)
*C07H 21/04*     (2006.01)
*A61K 38/53*     (2006.01)
*C07K 14/47*     (2006.01)
*C12N 9/00*      (2006.01)
*C12N 15/85*     (2006.01)

(52) U.S. Cl.
CPC .............. *A61K 48/005* (2013.01); *A61K 38/53* (2013.01); *C07K 14/4703* (2013.01); *C07K 14/4738* (2013.01); *C12N 9/93* (2013.01); *C12N 15/85* (2013.01); *C12N 2310/111* (2013.01); *C12N 2310/14* (2013.01); *C12Y 603/02019* (2013.01)

(58) Field of Classification Search
None
See application file for complete search history.

(56) References Cited

U.S. PATENT DOCUMENTS

| 6,737,244 | B2 | 5/2004 | Issakani et al. |
|---|---|---|---|
| 6,858,709 | B1 | 2/2005 | Conaway et al. |
| 6,982,277 | B2 | 1/2006 | Gudkov et al. |
| 6,989,383 | B1 | 1/2006 | Rosen et al. |
| 7,049,058 | B2 | 5/2006 | Singh |
| 7,101,543 | B2 | 9/2006 | Fakhrai |
| 2003/0003564 | A1 | 1/2003 | Tyers et al. |
| 2003/0232436 | A1 | 12/2003 | Monia et al. |
| 2005/0037389 | A1 | 2/2005 | Santin |
| 2008/0269158 | A1 | 10/2008 | Im et al. |
| 2011/0213016 | A1 | 9/2011 | Im et al. |

FOREIGN PATENT DOCUMENTS

WO     2006/044366      4/2006

OTHER PUBLICATIONS

Jung et al. (Nature Medicine, Jul. 2006, vol. 12, No. 7, pp. 809-816).*
Prosecution history for grandparent U.S. Appl No. 12/093,093, filed May 8, 2008 (downloaded Oct. 18, 2011), last document dated Aug. 12, 2010, 83 pp.
Prosecution history for parent U.S. Appl. No. 12/789,670, filed May 28, 2010 (downloaded Oct. 18, 2011), last document dated Oct. 18, 2011, 21 pp.
Search Report, dated Feb. 13, 2007, corresponding to International Application No. PCT/KR2006/004749 (filed Nov. 23, 2006), parent of the present application, 4 pp.
Chen et al., NCBI Nucleotide Accession No. NP_055316.2, Oct. 5, 2009, "Human ubiquitin-conjugating enzyme", 2 pp.
Vershaysky, NCBI Nucleotide Accession No. AAC52884.1, Nov. 7, 1996, "Mouse ubiquitin-conjugating enzyme E2".
Auger et al. (2005) "Quantitative Assays of Mdm2 Upiquitin Ligase Activity and Other Ubiquitin-Utilizing Enzymes for Inhibitor Discovery", Methods in Enzymology, 399:701-171, Elsevier Inc.
Bertrand et al. (2002) "Comparison of antisense oligonucleotides and siRNAs in cell culture and in vivo", Biochemical and Biophysical Research Communications, 296:1000-1004.
Kamura T. et al. (2002) "A Molecular Basis for Stabilization of the von Hippel-Lindau (VHL) Tumor Suppressor Protein by Components of the VHL Ubiquitin Ligase" J. Bio. Chem., 277(33):30388-30393.
Lewis et al. (Aug. 25, 2009) "High-Throughput Screening Reveals a Small-Molecule Inhibitor of ROMK and Kir7.1", Mol Pharmacol, 1 p. (ahead of print).
Li et al. (2005) "VHL Protein-Interacting Deubiquitinating Enzyme 2 Deubiquitinates and Stabilizes HIF-1α", EMBO Reports, 6(4):373-378.
Li et al. Supplementary Information, "VHL Protein-Interacting Deubiquitinating Enzyme 2 Deubiquitinates and Stabilizes HIF-1α", 12pp.
Mahato et al. (Jan. 2005) "Modulation of gene expression by antisense and antigene oligodeoxynucleotides and small interfering RNA", Expert Opinion on Drug Delivery, 2(1):3-28.

(Continued)

*Primary Examiner* — Amy Bowman
(74) *Attorney, Agent, or Firm* — Lathrop & Gage LLP

(57) ABSTRACT

The present invention relates to the $E2_{EPF}$ UCP-VHL interaction and the uses thereof, more precisely a method for increasing or reducing VHL activity or level by regulating UCP activity or level to inhibit cancer cell proliferation or metastasis or to increase angiogenesis. The inhibition of UCP activity is accomplished by any UCP activity inhibitor selected from a group consisting of a small interfering RNA (RNAi), an antisense oligonucleotide, and a polynucleotide complementarily binding to mRNA of UCP, a peptide, a peptide mimetics and an antibody, and a low molecular compound. In the meantime, the increase of angiogenesis is accomplished by the following mechanism; UCP over-expression is induced by a gene carrier and thus endogenous VHL is reduced, leading to the stabilization of HIF-1α which enhances VEGF activation based on the HIF-1α stabilization. The method for regulating UCP activity or level results in the increase or decrease of VHL activity or level, so that it can be applied to the development of an anticancer agent and an angiogenesis inducer.

5 Claims, 45 Drawing Sheets

(56) References Cited

OTHER PUBLICATIONS

Maynard et al. (Aug. 2005) "Molecular Targets from VHL Studies into the Oxygen-Sensing Pathway", Current Cancer Drug Targets, 5:345-356.

Na et al. (Aug. 2003) "Overproduction of Vascular Endothelial Growth Factor Related to von Hippel-Lindau Tumor Suppressor Gene Mutations and Hypoxia-Inducible Factor-1[alpha] Expression in Renal Cell Carcinomas", J. Of Urology, 170(2, part 1): 588-592.

Nalepa et al. (Jul. 2006) "Drug discovery in the ubiquitin-proteasome system", Nature Reviews, Drug Discovery, 5:596-613.

Scherer et al. (2003) "Approaches for the sequence-specific knockdown of mRNA", Nat. Biotechnol., 21(12):1457-1465.

Tisdale, M.J. (2003) "The 'cancer cachectic factor'", Support Care Cancer, 11:73-78.

Li et al. (2005) *supplementary Information* for "VHL Protein-Interacting Deubiquitinating Enzyme 2 Deubiquitinates and Stabilizes HIF-1α," EMBO reports, doi: 10.1038/sj.embor.7400377, (supplemental information available at nature.com/embor/journal/vaop/ncurrent/extref/7400377-s1.pdf), 12 pages.

Wagner et al. (2004) "Overexpression, Genomic Amplification and Therapeutic Potential of Inhibiting the UbcH10 Ubiquitin Conjugase in Human Carcinomas of Diverse Anatomic Origin," Oncogene 23:6621-6629.

\* cited by examiner

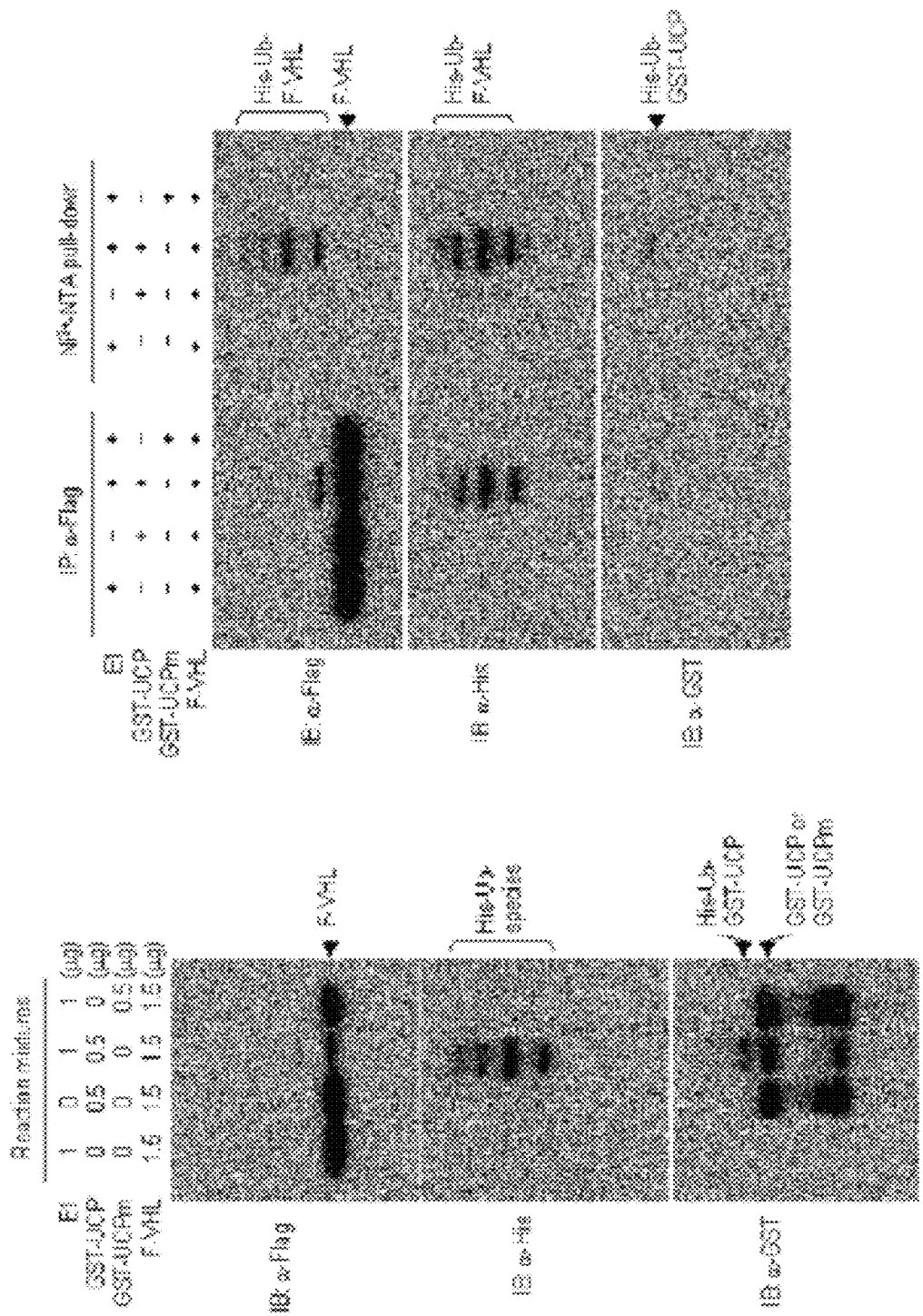

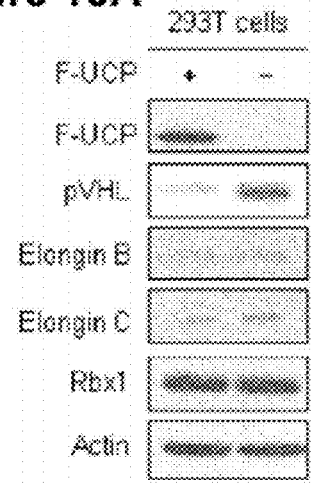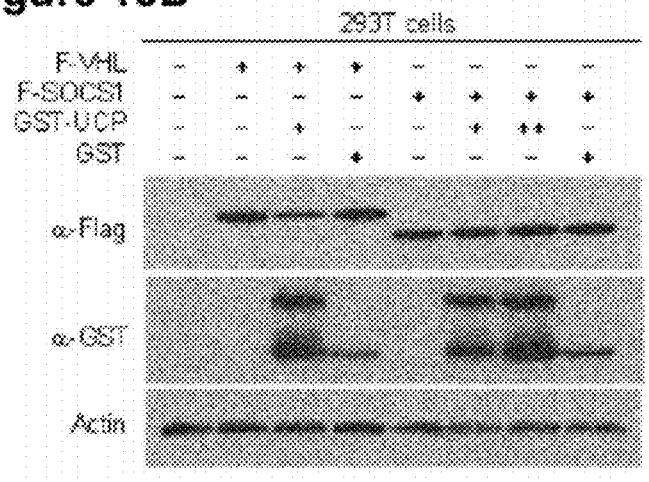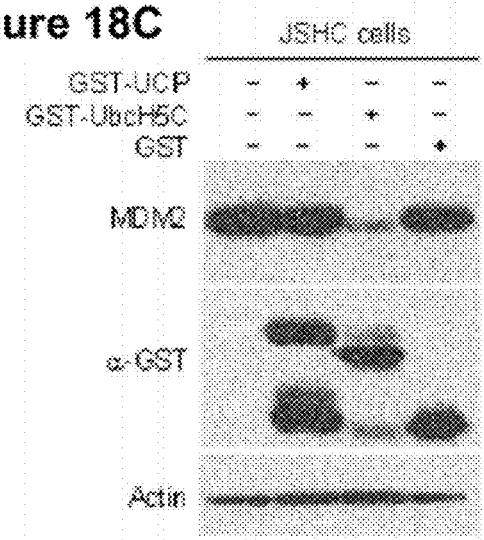

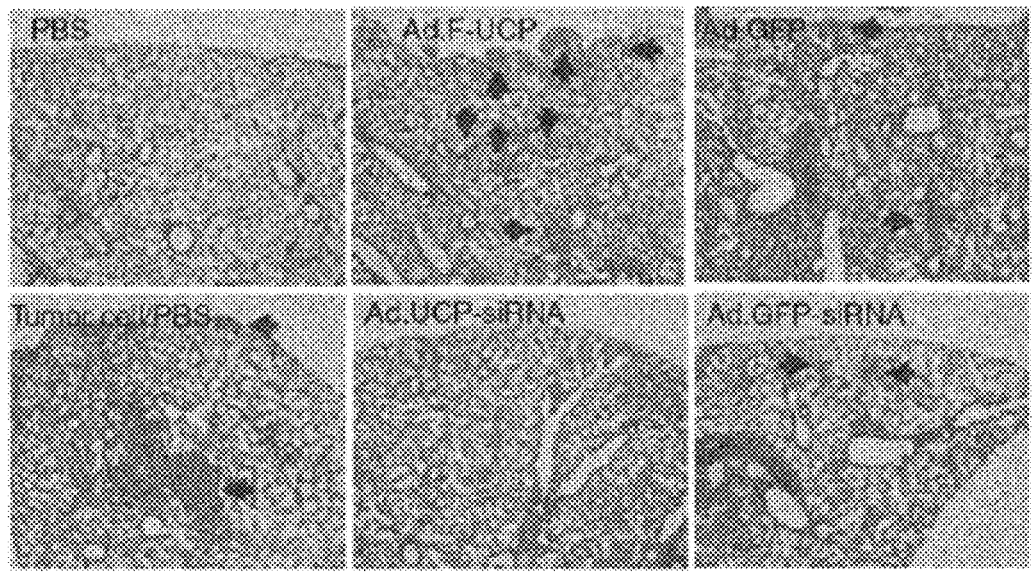
Figure 39
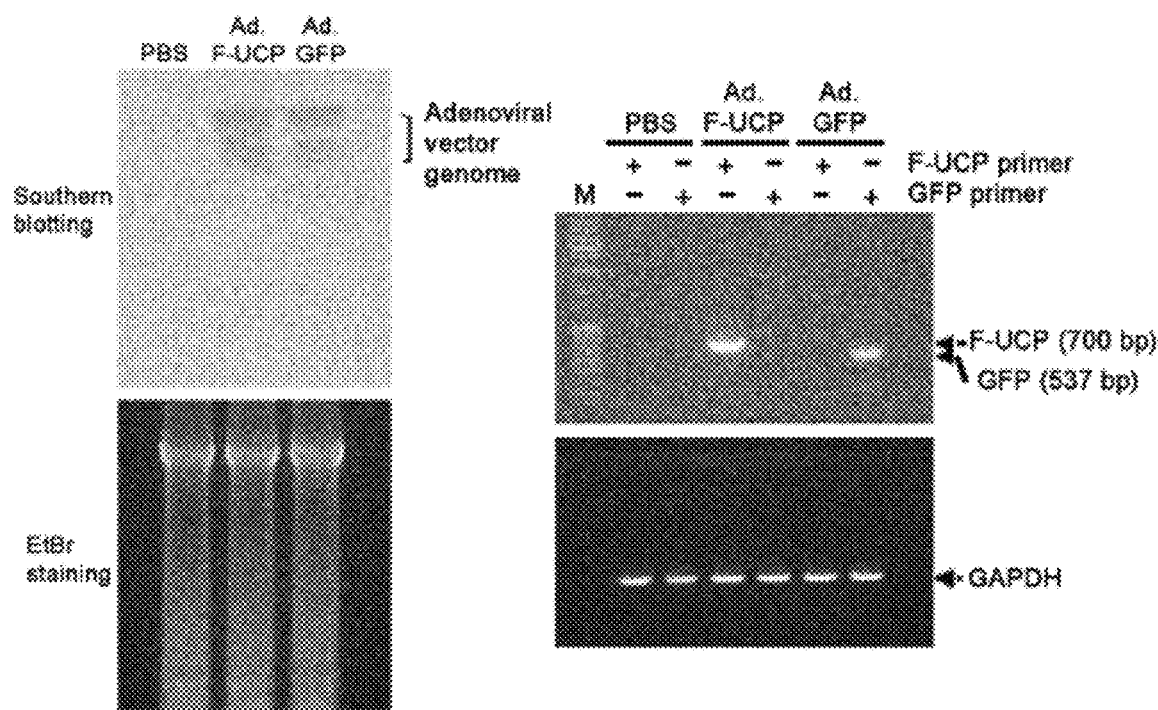
Figure 40A
Figure 40B

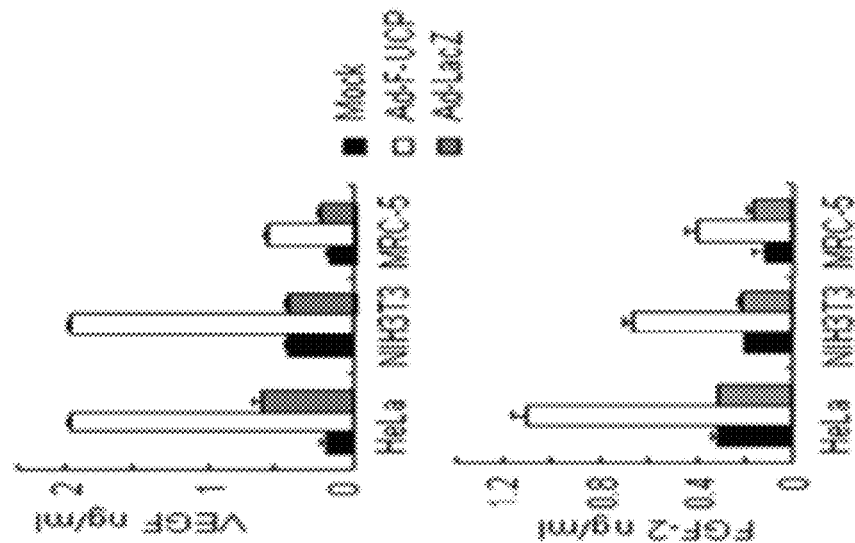
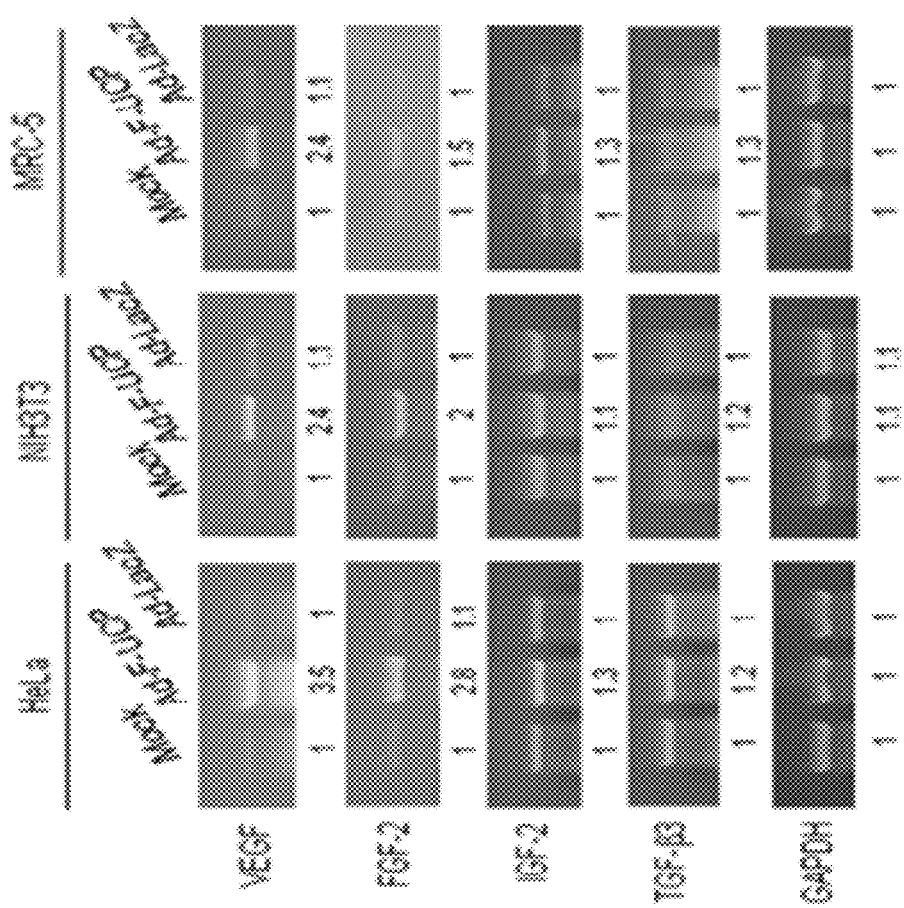
Figure 48A
Figure 48B

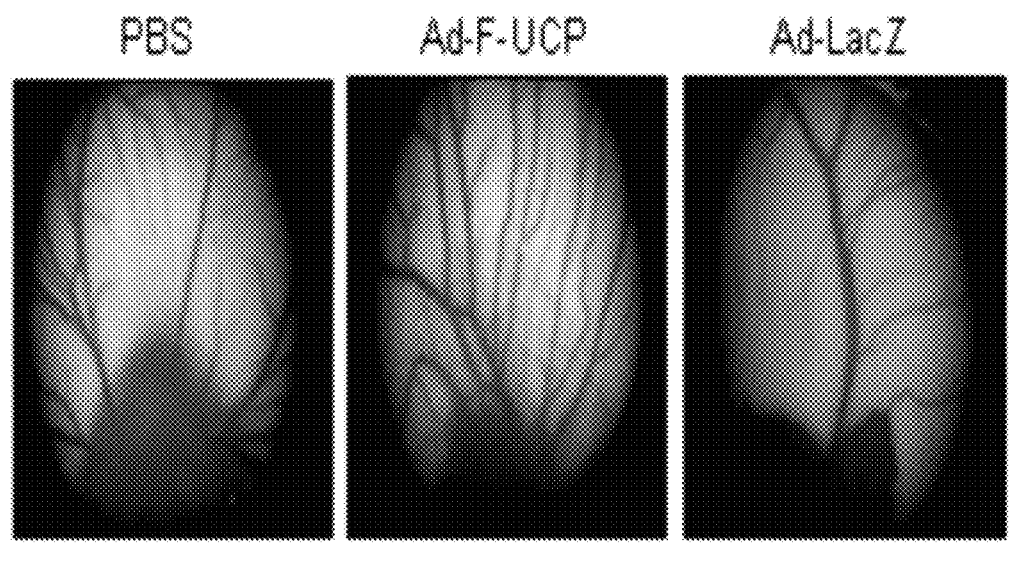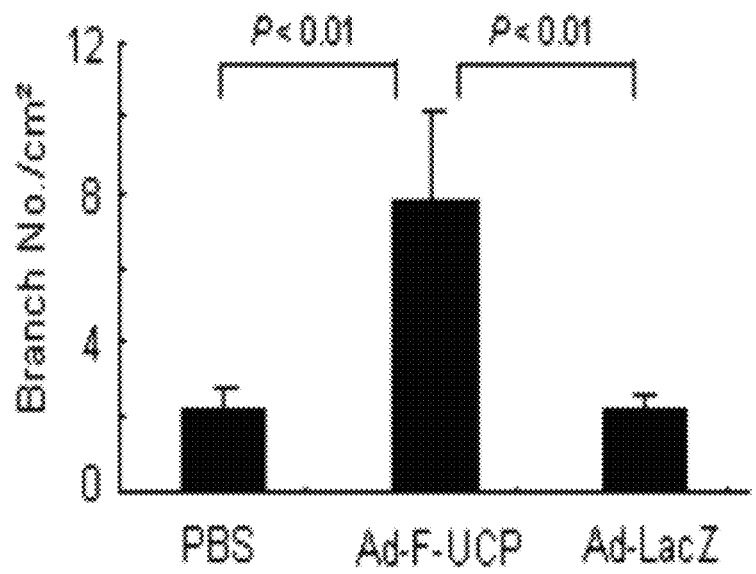
Figure 51

METHOD FOR THERAPEUTIC ANGIOGENESIS

CROSS-REFERENCE TO RELATED APPLICATIONS

This application is a continuation-in-part patent application of U.S. patent application Ser. No. 12/789,670 on May 28, 2010, which is a continuation/divisional of U.S. patent application Ser. No. 12/093,093, filed under 35 U.S.C. 371 on May 8, 2008 as a national stage application of International Application PCT/KR2006/004749, filed Nov. 13, 2006, which claims priority to Korean Patent Application No. KR10-2005-0108014, filed Nov. 11, 2005.

TECHNICAL FIELD

The present invention relates to $E2_{EPF}$ UCP-VHL interaction and the uses thereof, more precisely a method for increasing or reducing VHL activity or level by regulating UCP to inhibit cancer cell proliferation or metastasis or to increase angiogenesis, in which an UCP inhibitor selected from a group consisting of a small interfering RNA (RNAi), an antisense oligonucleotide, and a polynucleotide complementarily binding to UCP mRNA, a peptide, a peptide mimetics, an antibody binding to UCP protein, and a low molecular compound, is used to inhibit UCP activity and the increase of angiogenesis is accomplished by enhancing VEGF expression based on the stabilization of HIFα by reducing endogenous VHL level, for which a gene carrier mediated UCP over-expression is induced.

BACKGROUND OF THE INVENTION $E2_{EPF}$-UCP (E2 Endemic pemphigus foliaceus ubiquitin carrier protein, thereinafter 'UCP') was first isolated from a human keratinocyte and was identified as a member of the ubiquitin conjugating enzyme family. This protein is functioning as an E2 ubiquitin carrier of E3 ubiquitin ligase in vitro and UCP alone exhibits E3 ubiquitin ligase activity with inducing auto/multiubiquitination (Liu Z. et al., JBC 267, 15829-15835, 1992; Liu Z. et al., JBC 271, 2817-2822, 1996; Baboshina O V and Haas A L., JBC 271, 2823-2831, 1996). In addition, the nucleotide sequence of UCP has been known as a prognostic factor for breast cancer (Mutter G L and Baak J P A., J Clin Pathol. 58 (1):1-6, 2005; U.S. Pat. No. 6,703,204), which has been confirmed to be over-expressed 5 times higher in various cancer tissues including ovarian cancer tissues than in normal tissues (Welsh J B et al., PNAS USA 98, 1176-81, 2001; Wagner K W, Oncogene 23, 6621-6629, 2004). However, the substrate specificity, intracellular functions and the involvement of UCP in tumorigenesis, tumor progression, metastasis and angiogenesis still remain unexplained.

The mutation of a tumor suppressor gene VHL (von-Hippel-Lindau) is closely related to the development of kidney cancer and hemangioblastoma in central nervous system and retina (Kaelin W G Jr., Nat Rev Cancer 2, 673-682, 2002; Curr Opi Gen Dev 13, 56-60, 2003; Trends Mol Med 10, 146-149, 2004; Trends Mol Med 10, 466-472, 2004). The over-expression of VHL in cancer cells inhibits tumor progression (Gene Ther 10, 2081-2089, 2003). VHL forms a multiple complex together with Elongin B and C, Rbx1 and Cullin 2, and then exhibits E3 ubiquitin ligase activity (Nat Rev Cancer 2, 673-682, 2002; Curr Opi Gen Dev 13, 56-60, 2003; Trends Mol Med 10, 146-149, 2004; Trends Mol Med 10, 466-472, 2004). That is, VHL functions as the substrate-recognition module of the E3 ubiquitin ligase complex composed of Elongin B and C, Rbx1 and Cullin2 (Nat Rev Cancer 2, 673-682, 2002; Curr Opi Gen Dev 13, 56-60, 2003; Trends Mol Med 10, 146-149, 2004; Trends Mol Med 10, 466-472, 2004). The famous VHL E3 ubiquitin ligase substrates are HIF1α and HIF2α, which are hydroxylated by a proline hydroxylase in the presence of oxygen and then hydroxylated HIFα is bound to VHL and ubiquitinated by VHL E3 ubiquitin ligase, followed by degradation by 26S proteasome (Nat Rev Cancer 2, 673-682, 2002; Curr Opi Gen Dev 13, 56-60, 2003; Trends Mol Med 10, 146-149, 2004; Trends Mol Med 10, 466-472, 2004). By binding with HIF1β, HIF1α or HIF2α acts as HIF1 or HIF2 transcription factor to maintain oxygen-dependent cellular homeostasis. HIF1α or HIF2α is stabilized under hypoxia, under which HIFα is not hydroxylated so that it is not ubiquitinated by VHL E3 ubiquitin ligase. HIF1 or HIF2 activates transcription of such genes as VEGF, angiopoietin 2, erythropoietin, and GLUT1 (Nat Med 9, 677-684, 2003). Vascular endothelial growth factor (VEGF) is a crucial factor involved in angiogenesis (Nat 359, 843-845, 1992; Nat 359, 845-848, 1992). Oxygen and nutrition need to be supplied to cancer cells by blood vessels. The HIF-VEGF pathway is closely associated with tumor progression, metastasis and angiogenesis (PNAS USA 94, 8104-8109, 1997; Can Res 60, 4010-4015, 2000) and in fact HIFα and VEGF are molecular targets for the development of an anti-cancer agent (Ophthalmology 109, 1745-1751, 2002). In fact, VEGF inhibitor is now being used as anticancer drug (ex. Avastin) (Proc Am Soc Clin Oncol 21, 15, 2002).

In parallel with the attempt to develop a VEGF inhibitor as an anticancer agent, study to treat vascular disorders such as ischemic diseases by using the VEGF gene is undergoing. Ischemic diseases include cardiovascular disease caused by the interruption of bloodstream are exemplified by myocardial ischemia and peripheral vascular disease. To make the bloodstream run smoothly, VEGF gene inducing angiogenesis has been tried to treat the above ischemic diseases (Yla-Herttuala S and Alitalo K. Nat Med. 9 (6):694-701, 2003; Khan T A et al., Gene Ther. 10 (4):285-91, 2003) and VEGF gene transfer has actually induced angiogenesis in an animal model (Leung D W et al., Science 8; 246 (4935):1306-9, 1989; Dvorak H F et al., Am J Pathol. 146 (5):1029-39, 1995). The effect of adenoviral vector encoding VEGF (Ad.VEGF) was examined in ischemic myocardium and muscle models, and the result confirmed that angiogenesis was clearly detected (Mkinen K et al., Mol. Ther. 6, 127-133, 2002). Particularly, when VEGF had been expressed in an animal model for 4 weeks, the induced angiogenesis did not vanish and rather the functions of tissues were improved even after the VEGF expression was terminated (Dor Y et al., EMBO J. 21, 1939-1947, 2002). The Ad.VEGF vector has been tested for the possibility of using as a therapeutic agent for coronary occlusion and peripheral deficiency in clinical phase 1-3 (Maekimen K et al., Mol Ther 6, 127-133, 2002; Stewart D J et al. Circulation 106, 23-26, 2002; Rajagopalan S et al., J Am Coll Cardil 41, 1604, 2003) and adenoviral vector encoding HIF1α has been also tested for the possibility of using as a therapeutic agent for myocardial ischemia in clinical phase 1 (Vincent K A et al., Circulation 102, 2255-2261, 2000). Although such clinical trials for the treatment of ischemic diseases by gene therapy using HIF-1α or VEGF gene have been undergoing, the underlying mechanisms of angiogenesis promotion by increasing VEGF expression induced by UCP mediated HIF-1α stabilization have not been explained, yet.

There are patent documents describing a method for inhibiting a gene involved in tumorigenesis and metastasis; International Patent Publication No. WO 2003/029292 describes a method for treating cancer by providing a peptide or its functional analogue to cells for targeting the cancer, International Patent Publication No. WO 1998/18480 describes a nucleic acid ligand inhibiting tumor growth by binding to VEGF, and International Patent Publication No. WO 98/45331 describes the inhibition mechanism of VEGF function by using an anti-VEGF antibody. However, the above methods are not much efficient. Thus, a more efficient novel method for regulating a tumor has to be developed. Korean Patent Publication No. 2005-0012082 describes a method for recovering the functions of aged cells by using siRNA. International Patent Publication No. WO 2003/006477 and No. WO 2004/015107 describe a method to inactivate a gene by using siRNA, but specific anticancer activity of siRNA has not been explained therein.

Thus, the present inventors experimentally proved that UCP binds specifically to VHL, UCP over-expression results in ubiquitin-mediated proteasomal degradation of a tumor suppressor VHL, and thereby HIF-1α is stabilized and VEGF expression is increased. The present inventors further examined the functions of UCP involved in tumor growth and metastasis by using siRNA that specifically inhibits UCP expression and as a result confirmed that UCP depletion resulted in anticancer effect and antimetastasis-effect in a mouse model. The present inventors also confirmed that UCP increases the expression of angiogenic factors including VEGF, VEGF level is high in UCP over-expressing cell culture media and the increased HUVEC (human umbilical vascular endothelia cell) proliferation in the presence of the culture media provides a clue for gene therapy for ischemic vascular diseases.

SUMMARY OF THE INVENTION

Technical Problem

It is an object of the present invention to provide a method for stimulating angiogenesis in a subject, by administering a pharmaceutically effective dosage of a Ubiquitin Carrier Protein (UCP) activity enhancer, an expression vector with the insertion of UCP gene or a UCP protein to the subject.

It is another object of the present invention to provide a method for treating ischemic diseases, including the step of administering a pharmaceutically effective dosage of a Ubiquitin carrier protein (UCP) activity enhancer, an expression vector with the insertion of UCP gene or a UCP protein to the subject.

Technical Solution

The present invention provides a method for stimulating angiogenesis in a subject, by administering a pharmaceutically effective dosage of a Ubiquitin Carrier Protein (UCP) activity enhancer, an expression vector with the insertion of UCP gene or a UCP protein to the subject.

The present invention also provides a treatment method for ischemic diseases, including the step of administering a pharmaceutically effective dosage of a Ubiquitin carrier protein (UCP) activity enhancer, an expression vector with the insertion of UCP gene or a UCP protein to the subject.

Hereinafter, the present invention is described in detail.

1. The present invention provides a method for stimulating angiogenesis in a subject, including the step of administering a pharmaceutically effective dosage of a Ubiquitin Carrier Protein (UCP) activity enhancer, an expression vector with the insertion of UCP gene or a UCP protein to the subject.

With regard to the method of stimulating angiogenesis, UCP activity enhancer preferably decreases von Hippel-Lindau (VHL) activity or level, increases stability of Hypoxia-inducible factor (HIF), and thereby induces angiogenesis factors, such as vascular epithelial growth factor (VEGF), but not strictly limited to these examples only.

In the specific embodiment of the present invention, it was demonstrated that over-expression of UCP results in increases in the mRNA level of angiogenesis factors (FIG. 48a), and angiogenesis factors were secreted out of the cell (FIG. 48b), promoting proliferation, tubule formation, and invasion of human umbilical vein endothelial cell (HUVEC) (FIG. 49). Based on these results, in order to prove that UCP over-expression stimulates in vivo angiogenesis, the inventors of the present invention injected UCP over-expressing cells into mouse muscle subcutaneously. As a result, mature blood vessels were significantly increased compared to controls (FIG. 50a, 50b). Also, sprouting of blood vessels was increased in muscular tissue of mouse where Ad-F-UCP virus is injected (FIG. 50c), and expression of angiogenesis related factors was increased in the muscular tissue (FIG. 50d). Furthermore, when chicken chorioallantoic membrane (CAM) assay was performed, culture medium of UCP over-expressing cells induced neo-vascularization (FIG. 51).

Therefore, as UCP over-expression is effectively stimulating angiogenesis by promoting both expression and secretion of angiogenesis factors in vitro and in vivo, the UCP activity enhancer can be efficaciously used as an angiogenesis promoter.

2. The present invention also provides a method for treating ischemic diseases, including the step of administering a pharmaceutically effective dosage of a Ubiquitin carrier protein (UCP) activity enhancer, an expression vector with the insertion of UCP gene or a UCP protein to the subject.

With regard to the method of treating ischemic diseases, UCP activity enhancer preferably decreased von Hippel-Lindau (VHL) protein level, and consequently stabilized hypoxia-inducible factor 1α (HIF1α), which resulted in inducing expression of angiogenesis factors such as vascular endothelial growth factor (VEGF), although the embodiment is not strictly limited to these examples only. Also, with regard to the method of treating ischemic diseases, the UCP activity enhancer is preferably carried by a plasmid or a virus gene carrier inducing UCP expression, although the embodiment is not strictly limited to these examples only.

In the specific embodiment of the present invention, limb loss and foot necrosis that can be observed in the mouse ischemia hindlimb model were significantly recovered or prevented when Ad-F-UCP virus was injected, and upon observing the tissue with tomographic imaging device, it was observed that the capillaries were increased and blood vessels were thickened (FIG. 52b). Furthermore, when expression of angiogenesis factors in the muscular tissue of ischemia model was investigated, mRNA level of angiogenesis factors in tissue where Ad-F-UCP was injected increases more than in the tissue with or without Ad-LacZ injection (FIG. 52d). As a result of immunoblot analysis (FIG. 52c) and limb tissue staining (FIG. 52e), expression of mature blood vessel markers, such as CD31 and smooth muscle actin (SMA), was increased (FIG. 52c). In other words, it was confirmed that in mouse ischemia hindlimb model, limb loss and foot necrosis were recovered by injection of Ad-F-UCP, and that this recovery was due to generation of new blood vessels resulted from increased expression of angiogenesis factors by UCP over-expression. Therefore, it can be easily inferred that the UCP activity enhancer can be used as a treatment for ischemia diseases.

3. The present invention also provides a method for diagnosis and prognosis of cancer by measuring UCP expression in a diagnostic sample of a patient and a diagnostic kit for the above diagnosis and prognosis.

1) The present invention provides a diagnostic method of cancer including the step of measuring UCP expression in a diagnostic sample of a patient.

UCP over-expression in a diagnostic sample indicates the patient gets a cancer. UCP expression according to this diagnostic method is measured by the same manner as described in the above screening method to detect UCP gene expression or protein activity.

2) The present invention provides a method for evaluation of a cancer treatment effect including the step of measuring UCP expression in a diagnostic sample of a subject who had gotten cancer treatment or has been under the treatment.

In this diagnostic sample, normal UCP expression indicates that the cancer treatment was successful, while UCP over-expression indicates the further treatment is required.

3) The present invention provides a method for predicting prognosis of a cancer model including the step of measuring UCP expression in a diagnostic sample of a subject.

Herein, normal UCP expression is a good sign for prognosis, but UCP over-expression in the diagnostic sample means the prognosis is poor.

4) The present invention provides a diagnostic kit for cancer which additionally includes one or more compounds reacted with UCP and a reagent for the detection of a reaction product and instructions for the same. One or more compounds reacted with UCP herein can be RNA complementarily binding to RNA or DNA of UCP or DNA and UCP protein binding antibody. The reagent for the detection of a reaction product can be a nucleic acid or a protein label and a coloring reagent.

4. The present invention provides a method for increasing VHL activity or level, reducing HIFα stability and inhibiting VEGF expression by reducing UCP activity or level.

The present inventors examined the relation of UCP with VHL, HIF-1α and VEGF.

First, the present inventors confirmed that UCP binds specifically to VHL (see FIG. 4-FIG. 7) but not to Elongin B, Elongin C, Rbx1 and Cullin 2 which form a complex with VHL (see FIG. 7 FIG. 8b). The expression of VEGF mRNA, a target molecule of HIF-1α and HIF-2α, in the presence of UCP was investigated. As a result, the expression levels of VHL and HIF-1α mRNAs were not changed but the expression of VEGF mRNA was increased by UCP over-expression (see FIG. 11), suggesting that UCP post-translationally regulated the level of VHL that targets HIF-1α for ubiquitination and thereby VHL mediated HIF-1α degradation was reduced and consequently intracellular HIF-1α level was increased, which meant the VEGF transcription was activated. From the reporter assay using HRE (hypoxia response element)-luc activated by HIF-1α, it was confirmed that HRE-luc activity was increased UCP dose-dependently in both hypoxic and normoxic conditions, indicating that stabilized HIF-1α was active (see FIG. 10 and FIG. 15b).

To examine whether the UCP mediated VHL degradation in cells was attributed to ubiquitin-mediated proteolysis or not, UCP mediated ubiquitination of VHL was investigated in vitro and in vivo. A UCP mutant was also generated, with which autoubiquitination assay was performed in vitro. As a result, UCP enzyme activity of the mutant was lost (see FIG. 14) and intracellular level of VHL was UCP enzyme activity-dependently reduced (see FIG. 12). Multiubiquitination of VHL was confirmed to be induced by the enzyme activity of UCP (see FIGS. 13, 14, 16 and 17). These results indicated that UCP induces ubiquitin-mediated proteolysis of VHL (see FIG. 14 and FIG. 16). Also, UCP acts as an E2 ubiquitin carrier and contains E3 ubiquitin ligase activity as well.

VHL is known to form a VHL E3 ubiquitin ligase complex that targets HIF1α and HIF2α for ubiquitination and degradation. The present inventor identified UCP had the E3 ubiquitin ligase activity targeting VHL for ubiquitination and degradation (see FIG. 9-FIG. 14, FIG. 16 and FIG. 17). Accordingly the present inventors proved that UCP over-expression led to VHL degradation (see FIG. 9-FIG. 14) with increasing the stability of HIF1α and HIF2α (see FIG. 9-FIG. 14 and FIG. 41-FIG. 45), and thereby increased the expression of VEGF, an angiogenic factor, regulated by HIF1α and HIF2α (see FIG. 11 and FIG. 24). In the meantime, UCP depletion resulted in the increase of endogenous VHL level, the decrease of HIFα stability and the inhibition of tumor growth and metastasis (see FIG. 23-FIG. 29, FIG. 32-FIG. 39 and FIG. 41-FIG. 45).

Inhibition of UCP activity is realized by a UCP transcription inhibitor, a transcribed UCP mRNA translation inhibitor or a UCP protein function inhibitor.

The UCP activity inhibitor can be selected from a group consisting of an antisense oligonucleotide complementarily binding to UCP mRNA, a UCP specific small interfering RNA, an inactivated UCP like protein or its fragment, a UCP binding peptide, a UCP specific antibody, a compound inhibiting the transcription or translation of UCP mRNA and a compound inhibiting the functions of UCP.

The UCP protein function inhibitor can be a low-molecular compound, a peptide or a protein that is able to interrupt UCP enzyme activity or UCP-VHL interaction.

The transcription inhibitor herein can be a protein or a compound that inhibits UCP transcription, regulation of which is mediated by a transcription factor or enhancer that binds to the UCP promoter.

The mRNA translation inhibitor can be selected from a group consisting of a low molecular compound, a RNA constructed by using an antisense nucleic acid sequence or RNAi technique, and siRNA.

5. The present invention also provides a UCP-siRNA oligomer, an expression vector thereof and a preparing method of the same.

A plasmid expression vector containing UCP-siRNA is composed of H1 promoter, UCP-siRNA and five T nucleotides (T5) which is a transcription termination sequence. RNA is composed of the antisense sequence complementarily binding to the 17-25-mer sense sequence selected from UCP mRNA nucleotide sequences, which is represented by SEQ. ID. NO: 6, but not always limited thereto.

The present inventors constructed a recombinant expression vector by cloning the 615-633 region of UCP mRNA represented by SEQ. ID. NO: 5 into pSuper plasmid vector including H1 promoter for the expression. The pSuper plasmid vector were digested with restriction enzymes and resulting DNA fragment was inserted into the adenoviral pShuttle vector, resulting in the construction of an adenoviral UCP-siRNA expression vector composed of H1 promoter, UCP-siRNA, and five T nucleotides. The vector for expressing UCP-siRNA herein is not limited to pSuper vector or pShuttle vector, and the promoter for expressing UCP-siRNA is not limited to H1 promoter, either. For example, any expression vector that is able to express a target gene such as U6 promoter or CMV promoter in a mammalian cell can be used. After constructing the adenoviral expression vector using the above described expression vector, adenoviral particles are prepared by the method described in Example 5 and introduced into cells or a subject to express siRNA therein. In addition to the adenoviral vector, any viral vector selected from a group consisting of adeno-associated virus, retrovirus, vaccinia virus and oncolytic virus can be used.

6. The present invention further provides an anticancer agent containing a UCP activity inhibitor as an effective ingredient.

The composition of the present invention contains the above effective ingredient by 0.0001-50 weight % for the gross weight of the composition.

The composition of the present invention can additionally include one or more effective ingredients having the same or similar functions to the above effective ingredient.

The composition of the present invention can also include, in addition to the above-mentioned effective ingredients, one or more pharmaceutically acceptable carriers for the administration. Pharmaceutically acceptable carrier can be selected or be prepared by mixing more than one ingredients selected from a group consisting of saline, sterilized water, Ringer's solution, buffered saline, dextrose solution, maltodextrose solution, glycerol and ethanol. Other general additives such as anti-oxidative agent, buffer solution, bacteriostatic agent, etc, can be added. In order to prepare injectable solutions, pills, capsules, granules or tablets, diluents, dispersing agents, surfactants, binders and lubricants can be additionally added. The composition of the present invention can further be prepared in suitable forms for each disease or according to ingredients by following a method represented in Remington's Pharmaceutical Science (the newest edition), Mack Publishing Company, Easton Pa.

The anticancer agent of the present invention can be administered orally or parenterally (for example, intravenous, hypodermic, local or peritoneal injection). But, parenteral administration is preferred and particularly intravenous injection is more preferred. The effective dosage of the composition can be determined according to weight, age, gender, health condition, diet, administration frequency, administration method, excretion and severity of a disease. The dosage of the composition is 0.1-100 mg/kg per day, and preferably 0.5-10 mg/kg per day. Administration frequency is once a day or preferably a few times a day.

The siRNA or siRNA expression vector of the present invention was i.v. injected to mice to investigate toxicity. As a result, it was evaluated to be safe substance since its estimated LD50 value was much greater than 1,000 mg/kg in mice.

The UCP activity inhibitor of the present invention targets the proliferation of such cancer cells exhibiting UCP over-expression as ovarian cancer, cholangiocarcinoma, liver cancer, colorectal cancer, stomach cancer, breast cancer, kidney cancer, prostate cancer and skin cancer cells.

The present inventors generated small interfering RNA complementarily binding to UCP mRNA (UCP-siRNA) and introduced it into cancer cells to suppress UCP expression. When UCP expression was inhibited by UCP-siRNA, VHL level was increased (see FIG. 23-FIG. 31 and FIG. 41-FIG. 45) and cell growth was significantly reduced (see FIG. 23-FIG. 29 and FIG. 41-FIG. 46). Invasion assay was also performed to investigate the effect of UCP-siRNA on the metastasis of cancer cells. As a result, cell invasion was significantly inhibited by UCP-siRNA (see FIG. 23-FIG. 29 and FIG. 41-FIG. 45). Tumor cells were hypodermically injected into a nude-mouse. After detecting a 3 mm tumor, adenoviral vector encoding UCP-siRNA was intratumorally injected. As a result, tumor growth and metastasis were markedly inhibited (see FIG. 32-FIG. 39 and FIG. 41-FIG. 45).

The above results indicate that UCP plays an important role in tumor growth and metastasis and thus inhibition of UCP expression can suppress tumor growth and metastasis.

7. The present invention also provides a method for reducing VHL activity or level, enhancing HIFα stability or activity and promoting VEGF expression by increasing UCP activity or level.

As explained hereinbefore, UCP targets VHL for ubiquitination and degradation (see FIG. 9-FIG. 15), so accordingly VHL E3 ubiquitin ligase substrates HIF1α and HIF2α are stabilized (see FIG. 9-FIG. 15, FIG. 23-FIG. 39 and FIG. 41-FIG. 45), resulting in increased expression of VEGF, an angiogenic factor regulated by HIF1α and HIF2α (see FIG. 11 and FIG. 24). The expressed VEGF was detected in culture media of the cells expressing UCP (see FIG. 47a) and the detected VEGF was confirmed to enhance HUVEC proliferation (see FIG. 47b). VEGF expression was increased with the increase of UCP activity or level. An increase of VEGF expression by UCP is achieved by a compound inducing UCP mRNA expression or plasmid or viral expression vectors encoding UCP.

8. The present invention also provides a VEGF expression enhancer containing a UCP activity enhancer, a UCP introduced expression vector or a UCP protein as an effective ingredient.

The UCP activity enhancer herein includes a compound inducing UCP mRNA expression by activating UCP promoter (ex. a substance isolated from a strain (Korean Patent No. 2003-0013795) was used as a promoter expression inducer), a plasmid inducing UCP expression (ex: Korean Patent No. 10-0375890, Method of Artificial Regulation of Target Gene Expression Using Inducible Zinc Finger Expression System) or a viral gene carrier (ex: Korean Patent No. 2001-0006460, A gene delivery vehicle expressing the apoptosis-inducing proteins).

UCP over-expression induces VEGF expression. Thus, UCP over-expression like effect such as direct insertion of a UCP protein or a plasmid inducing UCP expression to an individual might bring the promotion of VEGF expression.

9. The present invention also provides an angiogenesis stimulator containing a UCP activity enhancer, a UCP introduced expression vector or a UCP protein as an effective ingredient.

UCP over-expression results in the increase of endogenous HIF-1α, CD31 protein (see FIG. 34), VEGF expression (see FIG. 11 and FIG. 24) and the proliferation of human vascular cells (see FIG. 47b). CD31 is a marker of vascular cells, which is detected when angiogenesis is induced by such factor as VEGF.

It has been well known that the increase of VEGF expression is effective for the treatment of ischemic vascular diseases (Yla-Herttuala S and Alitalo K. Nat. Med., 9 (6):694-701, 2003; Khan T A et al., Gene Ther. 2003, 10 (4):285-91). Thus, an angiogenesis stimulator containing a UCP gene introduced expression vector promoting VEGF expression can be effectively used for the patients who are supposed to get amputation because of critical limb ischemia (CLI) caused by deficient blood vessels or are suffering from inoperable coronary artery disease (CAD). UCP can also be a new target of gene therapy for those patients with incurable diseases such as dementia caused by insufficient blood supply, amyotrophic lateral sclerosis (ALS), diabetic neuropathy, stroke, etc.

10. The present invention also provides a screening method for a UCP activity regulator (inhibitor or enhancer) comprising the following steps:

1) Searching a UCP activity inhibitor by using a VHL expressing cell line; or

2) Searching a transcription factor involved in UCP transcription regulation;

3) Screening a substance regulating the transcription factor; and

4) Confirming UCP gene expression regulating activity of the screened substance.

Particularly, the present invention provides a screening method of a UCP activity regulator including the steps of:

1) Treating a sample compound to a cell line expressing UCP and VHL;

2) Measuring VHL activity or level of the cell line of step 1); and

3) Selecting a compound significantly changing VHL activity or level by comparing the result of step 2) with the result of a control, a screening method of a UCP activity regulator including the steps of:

1) Treating a sample compound to a cell line expressing UCP and VHL;

2) Measuring the level of ubiquitinated VHL of the cell line of step 1); and

3) Selecting a compound significantly changing the level of ubiquitinated VHL by comparing the result of step 2) with the result of a control, a screening method of a UCP activity regulator including the steps of:

1) Treating a sample compound to a cell line expressing UCP and HIF;

2) Measuring HIF activity of the cell line of step 1); and

3) Selecting a compound significantly changing HIF activity by comparing the result of step 2) and the result of a control, and a screening method of a UCP activity regulator including the steps of:

1) Treating a sample compound to a cell line expressing UCP and HIF;

2) Measuring the ubiquitinated HIF in the cell line of step 1); and

3) Selecting a compound significantly changing the level of ubiquitinated HIF by comparing the result of step 2) with the result of a control.

When UCP expression was inhibited, VHL activity was recovered and thereby cancer cell line growth was inhibited (see FIGS. 45, 35, 42, 45, 46a and 46c).

According to the screening method above, whether the UCP activity regulator inhibited or increased the expression or activity of the UCP gene was determined by the conventional method commonly used for investigating the interaction between RNA-RNA, DNA-DNA, DNA-RNA, RNA-protein, RNA-compound, DNA-protein, DNA-compound, protein-protein or protein-compound.

For example, interaction between protein-compound, protein-protein, RNA-RNA, DNA-DNA, DNA-RNA, RNA-protein, RNA-compound, DNA-protein, and DNA-compound can be investigated by the methods of in vitro hybridization examining the binding between the gene and an activity regulator candidate, Northern blotting using mammalian cells transfected with an inhibitor candidate, semi-quantified/quantified PCR and real-time PCR measuring the expression level of the UCP gene, and a method in which a plasmid carrying a reporter gene under the transcriptional control of UCP promoter is introduced into a cell which is reacted with an inhibitor candidate and then the expression of the reporter gene is measured.

To investigate the interaction between protein-protein and protein-compound, UCP protein is reacted with an activity regulator candidate in vivo and in vitro and the activity is measured, or cell growth in the cell line now expressing VHL or GFP-VHL is measured, or yeast two-hybrid method, UCP protein binding phage-displayed peptide clone detection, HTS (high throughput screening) using a natural and synthetic compound library, cell-based screening or DNA array based screening can be used.

In the above screening method, the UCP expression or activity regulator candidate can be a nucleic acid, a protein, other extracts or a natural substance which presumably have a function of inhibiting or increasing the enzyme activity or expression of UCP, or is a randomly selected individual compound.

The regulator candidate of the present invention which has been obtained by the screening method above and is believed to inhibit or increase the expression of the gene or stability of the protein can be coincidentally the lead molecule for the development of an anticancer agent or an angiogenesis stimulator. The lead molecule can be modified or optimized in its structure to be effectively functioning as an inhibitor or enhancer of UCP gene expression or UCP protein function, leading to a novel anticancer agent or an angiogenesis stimulator.

BRIEF DESCRIPTION OF THE DRAWINGS

The application of the preferred embodiments of the present invention is best understood with reference to the accompanying drawings, wherein:

FIG. 17 is a photograph of Western blotting illustrating that wild type UCP induces in vitro multiubiquitination of VHL but UCPm does not.

FIG. 18 and FIG. 19 are photographs of Western blotting illustrating that UCP specifically targets VHL for degradation.

FIG. 39 is a set of H&E staining photographs illustrating that UCP depletion by Ad.UCP-siRNA inhibits the metastasis of melanoma cells into the mouse lung, as indicated in FIG. 38.

FIG. 40a is a photograph of Southern blotting illustrating that the adenoviral genome expressing F-UCP and GFP lived long in tumor cells still after 21 days from the injection, as indicated in experiments described in FIG. 32-FIG. 34.

FIG. 40b is a photograph of RT-PCR illustrating that the adenovirus expressing F-UCP and GFP still expressed F-UCP and GFP in excised tumor cells after 21 days from the injection as indicated in experiments described in FIG. 32-FIG. 34.

FIG. 46 is a set of graphs and a photograph illustrating that a UCP inhibitor can be screened by the changes of proliferation rate of the cell line expressing HA-VHL.

FIG. 48a is a photograph showing increase of mRNA expression of angiogenesis-related factors by RT-PCR, after UCP is over-expressed in human cervical cancer cell line (HeLa) and mouse fibroblast cell line (NIH3T3) and human normal fibroblast cell line (MRC-5).

FIG. 48b is a graph demonstrating quantitatively with ELISA that by UCP over-expression, angiogenesis inducers, such as VEGF (vascular endothelial growth factor) and FGF-2 (fibroblast growth factor-2) are secreted into culture media.

FIG. 50b is a graph illustrating quantitatively increase of blood vessels and expression of blood vessel markers when UCP is over-expressed in the in vivo Matrigel plug assay of FIG. 50a.

FIG. 51 illustrates that culture medium from HeLa cells with UCP over-expression induces neo-vascularization in the chicken chorioallantoic membrane (CAM) assay.

DETAILED DESCRIPTION OF THE INVENTION

Figure 1:
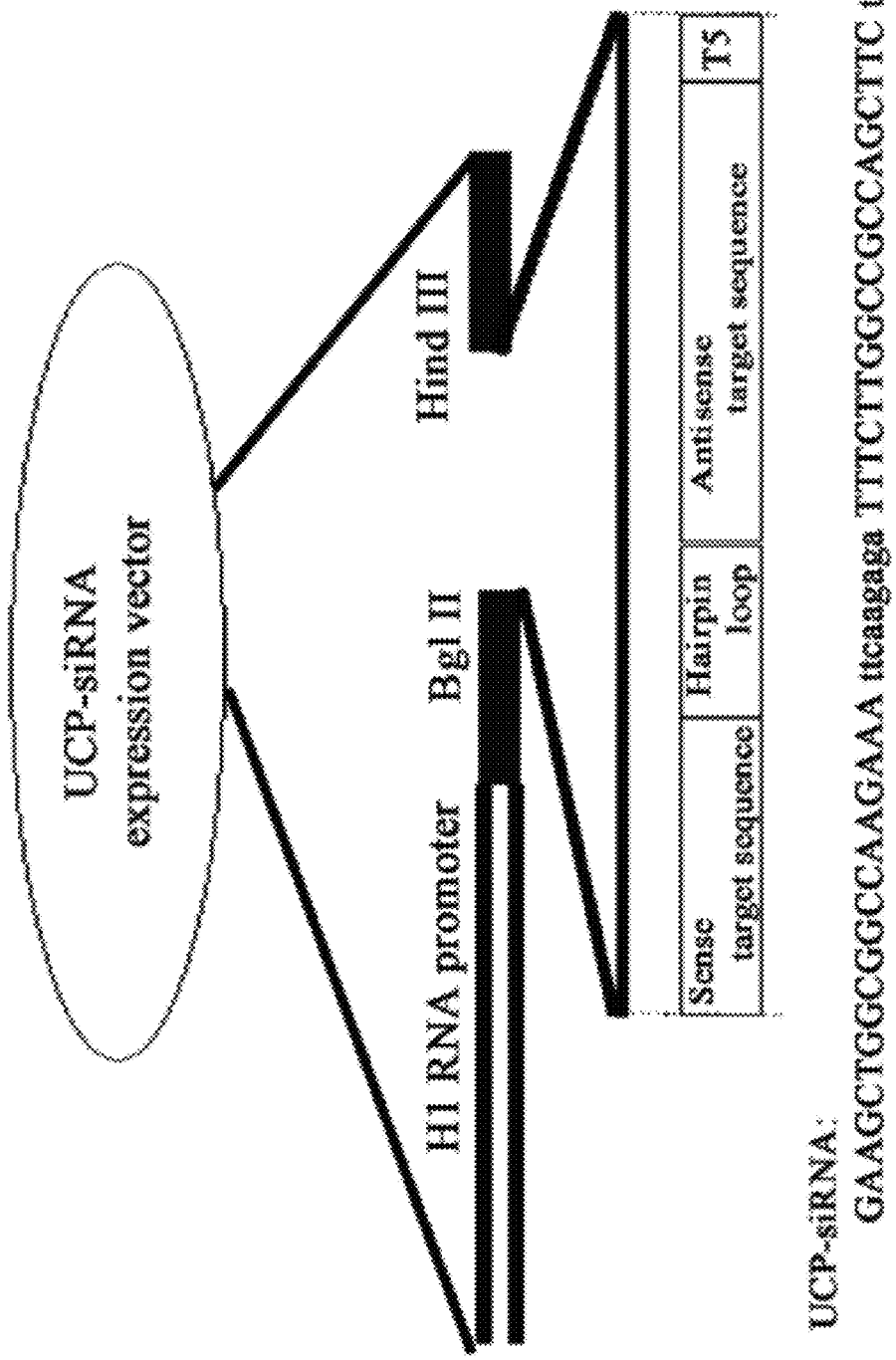
FIG. 1 is a schematic diagram showing the UCP-siRNA expression plasmid vector and the sequence of UCP-siRNA, see SEQ ID NO:6.
Figure 2:
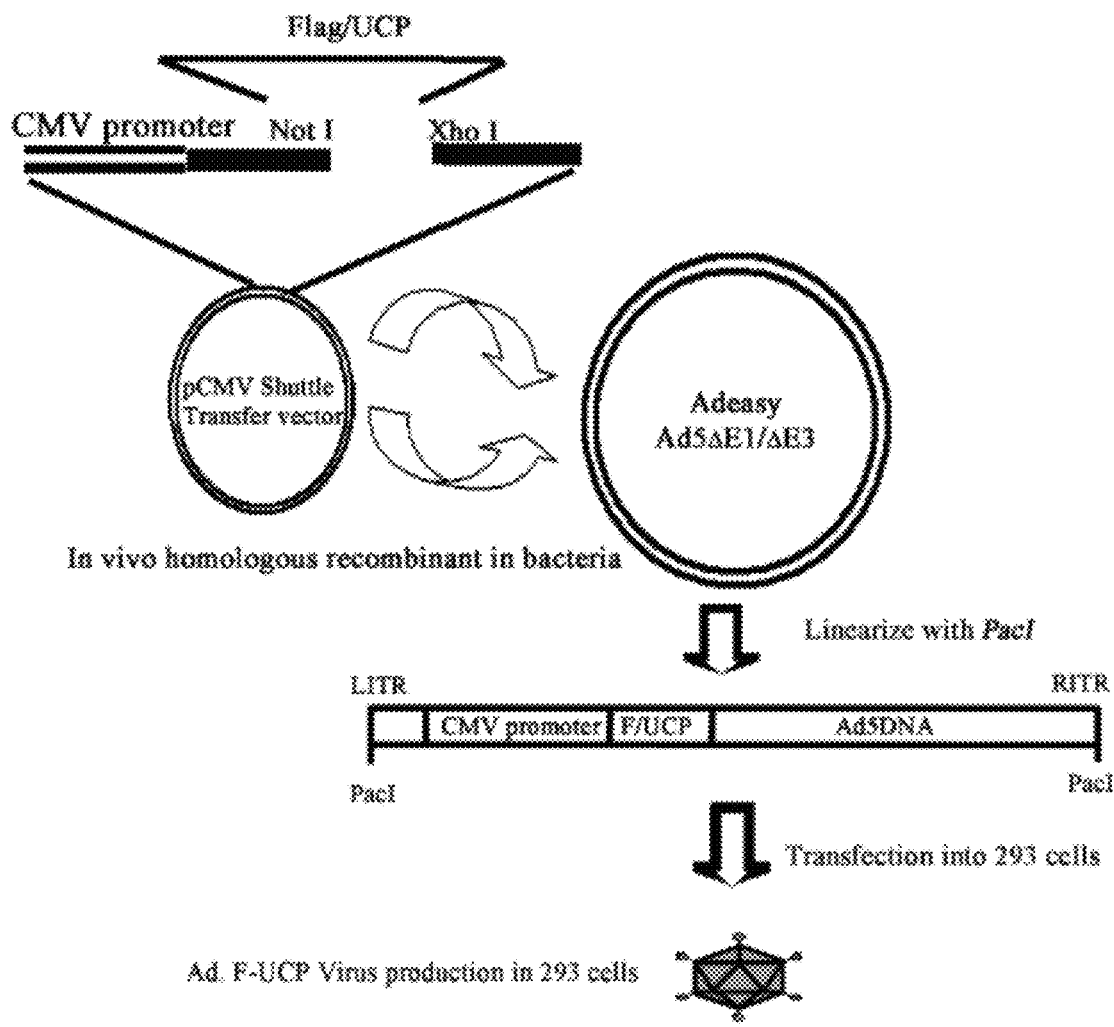
FIG. 2 is a schematic diagram illustrating the construction process of Ad.F-UCP vector.
Figure 3:
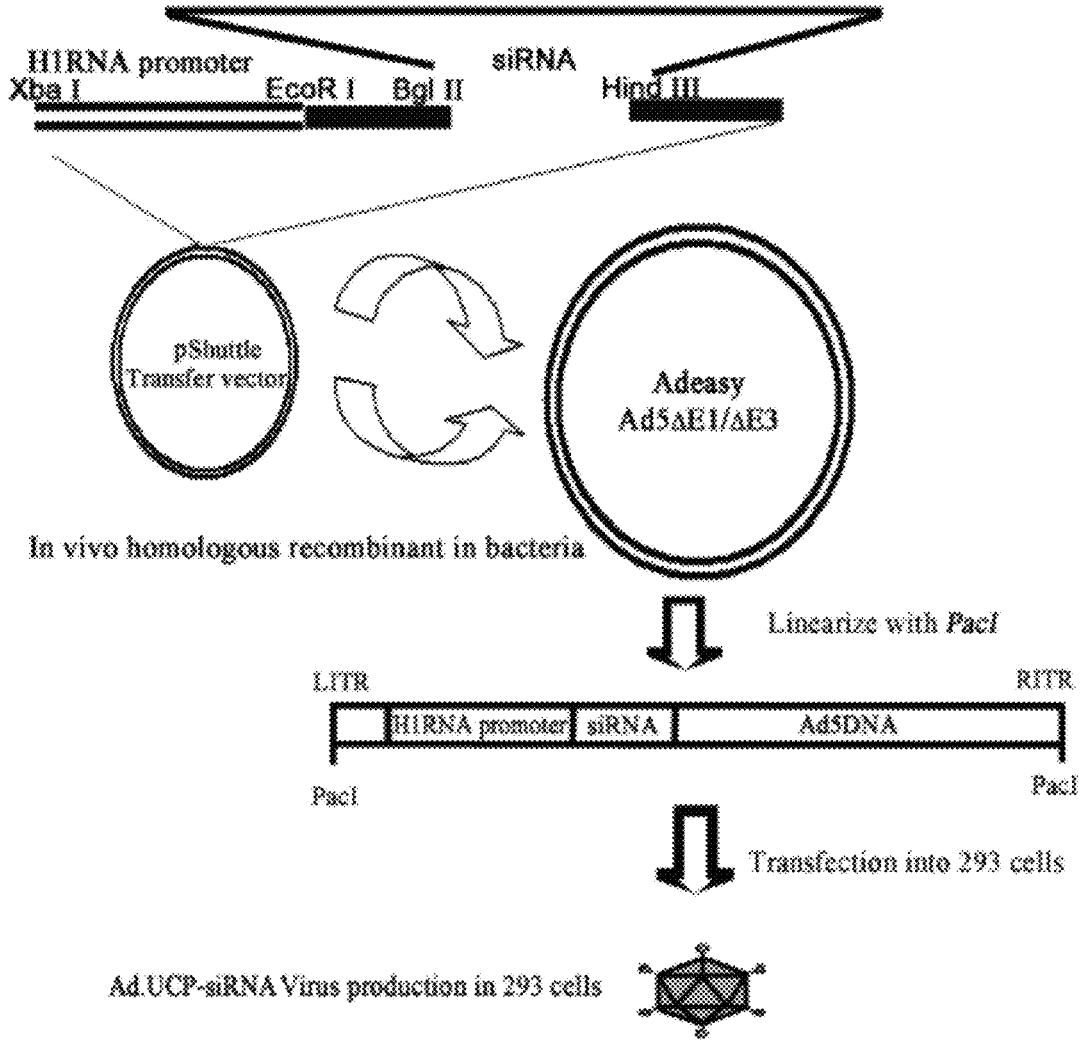
FIG. 3 is a schematic diagram illustrating the construction process of Ad.UCP-siRNA vector, see SEQ ID NO:6.
Figure 4:
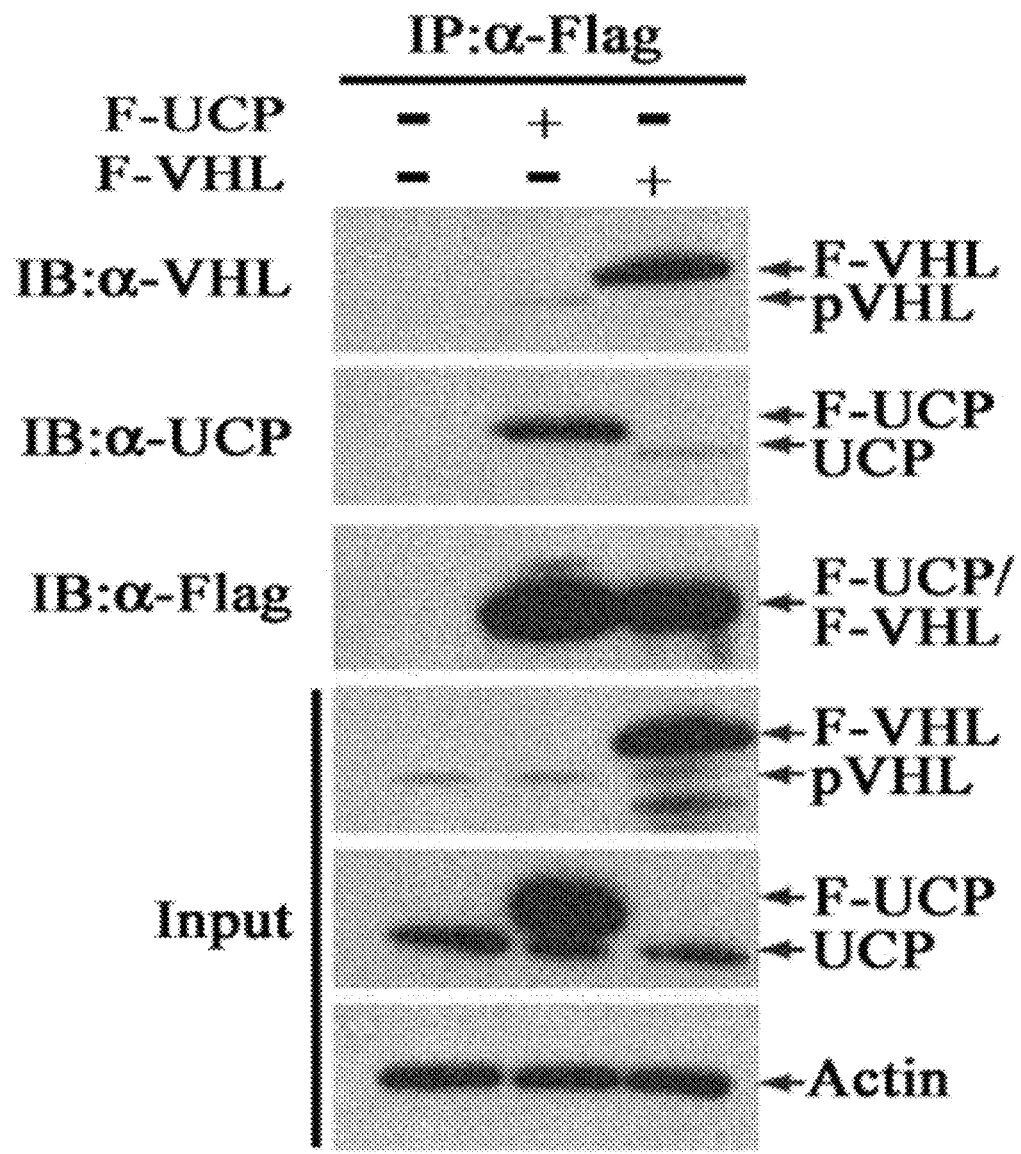
FIG. 4-FIG. 6 are photographs of Western blotting illustrating that UCP binds specifically to VHL in cells.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Intracellular Interaction Between UCP and VHL

To examine the interaction between UCP and VHL, an expression vector was constructed as follows. PCR was performed by using the UCP containing expression vector (pDEST$^{tm}$27GST-UCP) provided by The Center for Functional Analysis of Human Genome (Korea Research Institute of Bioscience and Biotechnology) as a template, followed by cloning of the resultant fragments into pCMV Tag1 (Stratagene) by using NotI/BamHI to construct Flag-UCP. PCR was performed as follows; predenaturation of the template with a primer set (SEQ. ID. NO: 1, Sense: 5'-tccgcggccgcat-gaactccaacgtggagaa-3', SEQ. ID. NO: 2, Antisense: 5'-accg-gatccctacagccgccgcagcgccc-3') using a DNA polymerase (pfu polymerase (Vent), New England Bioscience, USA) at 94° C. for 4 minutes, denaturation at 94° C. for 1 minute, annealing at 55° C. for 1 minute, polymerization at 72° C. for 1 minute, 30 cycles from denaturation to polymerization, and final extension at 72° C. for 5 minutes. GST-Rbx1, GST-Elongin B and GST-Elongin C were cloned into pEBG vector by using BamHI/NotI, and GST-VHL was cloned into pEBG vector by using BamHI/SpeI. Flag-VHL was provided from Dr. Sayeon Cho, Korea Research Institute of Bioscience and Biotechnology.

Among antibodies used herein, the mouse anti UCP antibody was directly generated by the present inventors. Particularly, UCP was cloned into pET28α vector by using BamHI/NotI and the protein was expressed in E. coli BL21. His-UCP was isolated from the E. coli by using $Ni^{2+}$-NTA resin. Purified His-UCP was inoculated with Freund's adjuvant (CHEMICON) into Balb/c mice (female, 6 week-old), four times, once a week. The obtained immunized serum was concentrated with protein A (SIGMA) for further use.

Flag-UCP expressing HEK293 cell line (293-F-UCP) was prepared as follows. Flag-UCP expression vector (pCMV Tag1-Flag-UCP) harboring the neomycin-resistant gene was introduced into cells by calcium-phosphate method, and the transfected cells were cultured on a selection medium (LD-MEM, containing 10% FBS, 100 μg/ml streptomycin and 100 unit/ml penicillin) supplemented with 1 mg/ml of neomycin.

Cell colonies expressing Flag-UCP were obtained for further use.

<1-1> Confirmation of Interaction Between UCP and VHL by Using Over-Expression System Interaction between over-expressed UCP and endogenous VHL and vice versa was investigated as follows. Flag-UCP and Flag-VHL expression vectors were transfected into HEK293T cells by using calcium phosphate method. Twelve hours before harvest, the cells were treated with 10 μM of MG132. The harvested cells were frozen at −70° C., and lysed in a lysis buffer (50 mM Tris, 0.5 mM EDTA, 0.1% NP-40, 0.5 mM PMSF). The mouse anti-Flag antibody conjugated to agarose (Sigma) was added to the lysates, followed by immunoprecipitation at 4° C. for 2 hours. The precipitates were mixed with SDS-sample buffer (62.5 mM Tris, 2% SDS, 5% beta-mercaptoethanol, 10% glycerol, 0.01% bromophenol blue), which was boiled at 95° C. for 5 minutes, followed by electrophoresis on 12.5% polyacrylamide gel. The proteins on the gel were transferred onto PVDF membrane, followed by blocking with 5% skim milk containing PBST (0.05% Tween-20 containing PBS) for 1 hour. Then, the membranes were incubated with mouse anti-Flag (Sigma), mouse anti-UCP or mouse anti-VHL antibodies (Pharmingen) at room temperature for 1 h. Upon completion of the reaction, remaining antibodies were washed out with PBST and reaction with horse radish peroxidase-conjugated rabbit anti-mouse antibody was performed at room temperature for one hour, followed by examination with ECL solution. Cell lysate of each group was subjected to Western blotting as described above. As a result, interaction between Flag-UCP and VHL and interaction between Flag-VHL and UCP were clearly detected.

<1-2> Interaction Between Endogenous UCP and VHL

Figure 5:
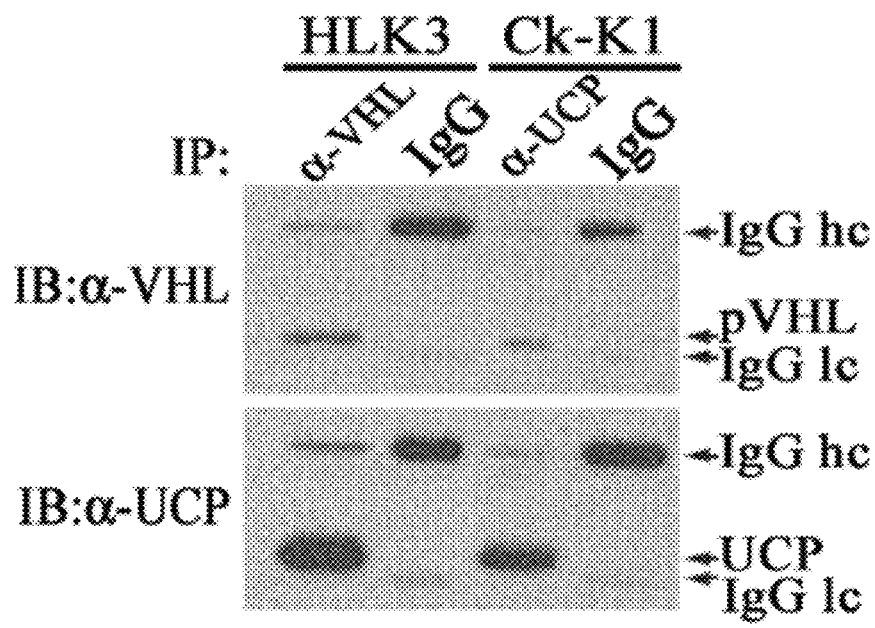

Interaction between endogenous UCP and VHL was investigated in HLK3 and Ck-K1 cancer cell lines expressing both VHL and UCP. HLK3 and Ck-K1 cancer cell lines cultured in HDMEM (containing 4.5 g/l glucose, 10% FBS, 100 μg/ml streptomycin and 100 unit/ml penicillin) in 5 100 mm dishes were recovered and frozen at −70° C. The frozen cells were lysed in a lysis buffer (50 mM Tris, 0.5 mM EDTA, 0.1% NP-40, 0.5 mM PMSF). 10 μg of each mouse anti-VHL antibody or mouse anti-UCP antibody and mouse immunoglobulin (as a control) were added to the cell lysate solution, followed by immunoprecipitation with the addition of protein A gel at 4° C. for 2 hours. Western blotting was performed with mouse anti-UCP antibody or mouse anti-VHL antibody by the same manner as described above. As a result, interaction between endogenous UCP and VHL was clearly detected (FIG. 5).

<1-3> Interaction Specificity of UCP to VHL

Figure 6:
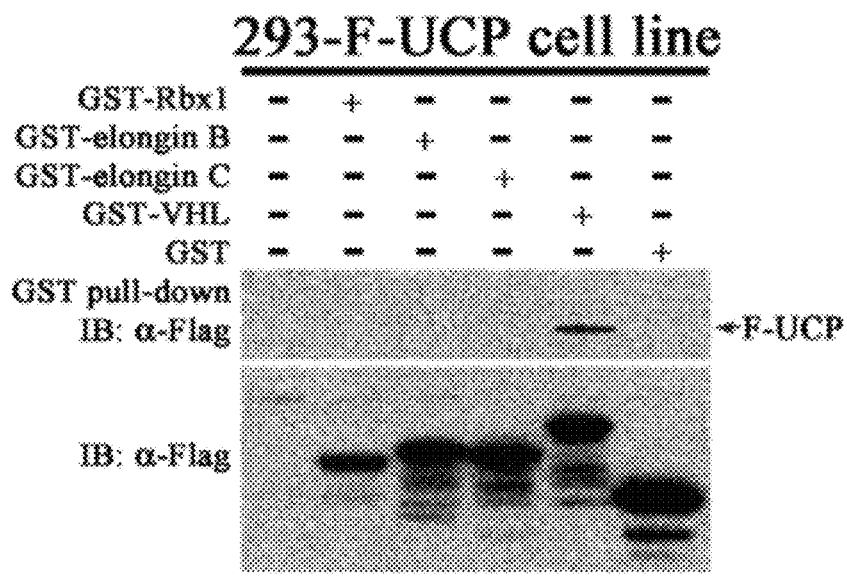

VHL forms E3 ubiquitin ligase complex with Elongin B, Elongin C, Rbx1 and Cullin 2, and HIF-1α is the representative substrate of this enzyme (Nat Rev Cancer 2, 673-682, 2002). The present inventors investigated if UCP interacting with VHL could interact with other molecules forming a VHL complex. HEK293 cells constitutively expressing Flag-UCP (293-F-UCP) were transfected with GST-Rbx1, GST-Elongin B, GST-Elongin C, GST-VHL and GST expression vectors respectively by calcium phosphate method. 12 hours before harvest, the cells were treated with 10 μM of MG132. The collected cells were frozen at −70° C. and then lysed in a cell lysis buffer (50 mM Tris, 0.5 mM EDTA, 0.1% NP-40, 0.5 mM PMSF). Glutathione-sepharose was added to the cell lysate solution, followed by GST pull-down at 4° C. for 2 hours. Western blotting was performed with mouse anti-Flag antibody by the same manner as described in the above. As a result, UCP was confirmed to interact specifically with VHL (FIG. 6).

Figure 7:
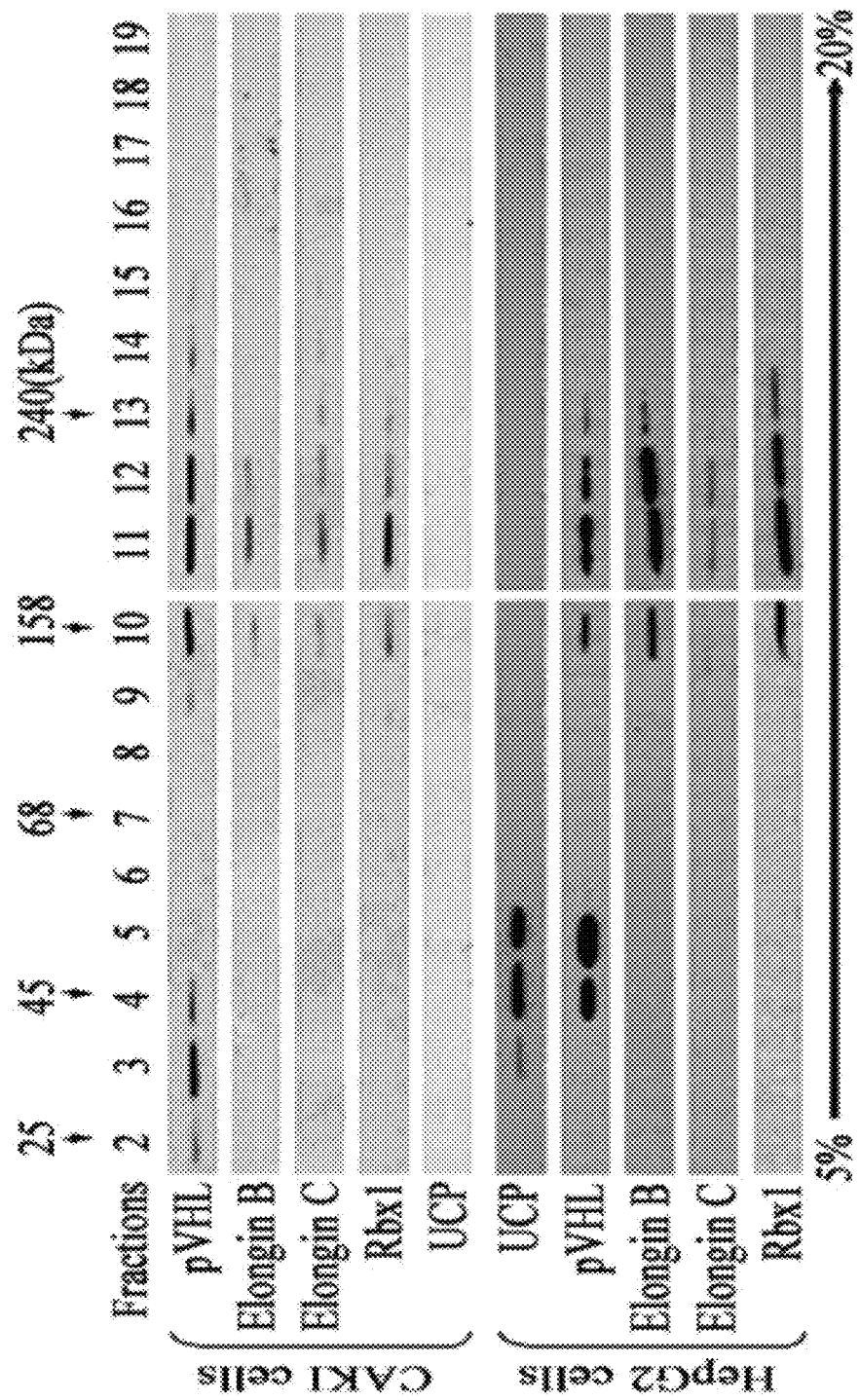
FIG. 7 is a photograph of Western blotting illustrating that VHL forms a VHL E3 ubiquitin ligase complex together with Elongin B, C and Rbx 1, but UCP is not a part forming VHL E3 ligase complex but independently forms a complex with VHL.

The intracellular interaction between UCP and VHL was also confirmed by detecting the molecular movement by sucrose density gradient centrifugation. CAKI (kidney cancer cell line) or HepG2 (liver cancer cell line) cells were collected from 10 100 mm culture dishes and frozen at −70° C. The frozen cells were lysed in 0.5 ml of a cell lysis buffer (50 mM Tris, 0.5 mM EDTA, 50 mM KCl, 10% glycerol, 1 mM DTT, 0.5% NP-40, 0.5 mM PMSF). The cell lysate was loaded in 10 ml of 5%-20% sucrose density gradient solution, followed by ultra-centrifugation at 35,000 rpm for 16 hours. 20 fractions were prepared by 0.5 ml, with which Western blotting was performed using mouse anti-UCP antibody, mouse anti-VHL antibody, rabbit anti-Elongin B, Elongin C, and Rbx1 antibodies (Santa Cruz). As a result, in CAKI cells, UCP was not detected in VHL E3 ligase complex (comprising VHL, Elongin B, Elongin c and Rbx1; fractions 10-12) and free VHL was detected at fractions 2-4 (FIG. 7, CAKI cell line). In the meantime, in HepG2 cells, UCP was also not detected in VHL E3 ligase complex at fractions 10-12, but co-sedimented with VHL (FIG. 7, HepG2 cell line, fractions 4-5).

<1-4> VHL-UCP Complex Formed by UCP Over-Expression

Figure 8A:
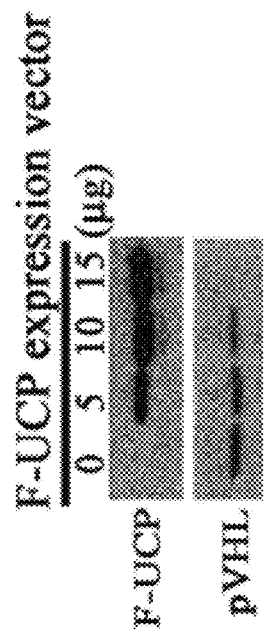
FIG. 8a is a photograph of Western blotting illustrating that the over-expression of UCP induces degradation of VHL in CAKI cell line.
Figure 8B:
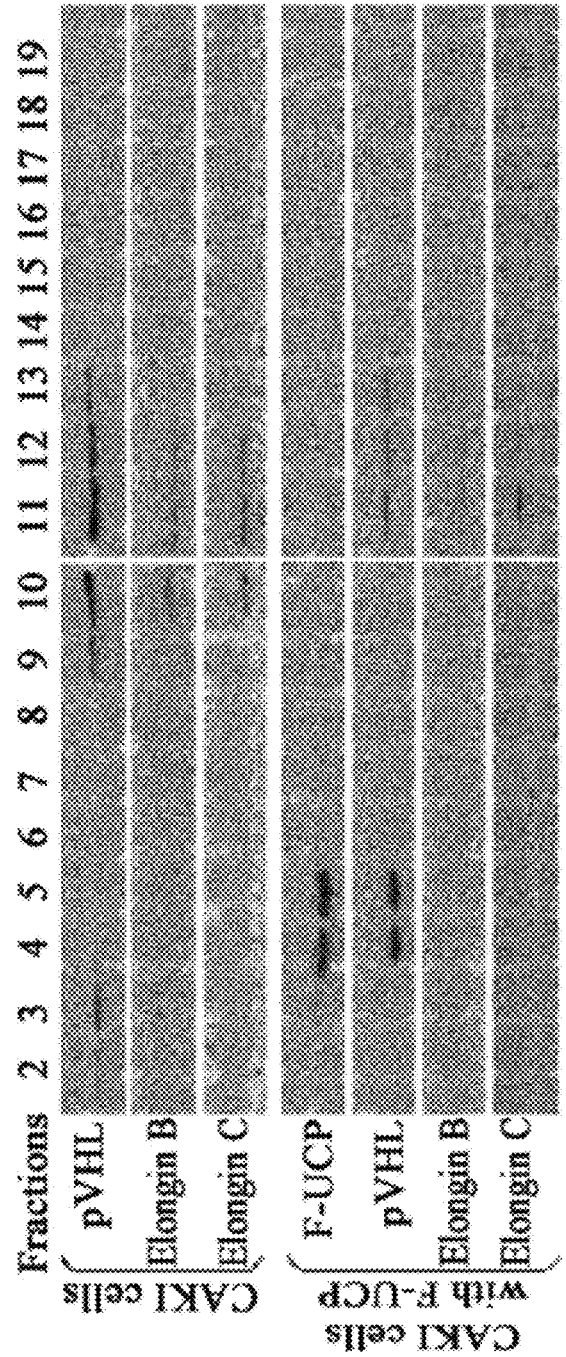
FIG. 8b is a photograph of Western blotting illustrating that the over-expressed UCP forms a complex with VHL in CAKI cell line.

F-UCP was over-expressed in a CAKI cell line where endogenous VHL level was high but endogenous UCP was not detected. The following experiment was performed to investigate UCP-VHL complex formation. Five 100 mm dishes of CAKI cell line were transfected with 10 μg of F-UCP plasmid or mock vector plasmid by using calcium phosphate method. 48 hours later, cells were harvested, followed by sucrose density gradient centrifugation as indicated in Example <1-3>. Western blotting was performed to investigate a complex formation. Free VHL detected at fractions 2-4 was detected in fractions 4-5 where UCP was co-sedimented with VHL when UCP was over-expressed, indicating that the UCP-VHL complex was formed (FIG. 8).

From the above results, it was confirmed that UCP interacts specifically with VHL to form a complex, which is though distinct from the VHL E3 ubiquitin ligase complex.

Example 2

The Effect of UCP on VHL Protein Stability

The decrease of endogenous VHL protein level by UCP might result from ubiquitin-mediated proteolysis of VHL and might result in stabilization of HIF-1α. To prove this hypothesis, following constructs were prepared.

HRE-luc reporter gene was generated by inserting 5×HREs derived from the VEGF promoter into pGL3-luciferase vector (Promega) containing SV40 TATA (Mol. Ther. 10, 938-949, 2004).

A mutant form of UCP 'Flag-UCPm' was constructed by replacing the active region of Flag-UCP, the $95^{th}$ cysteine, with serine by PCR. PCR was performed as follows; predenaturation of the template with a primer set (SEQ. ID. NO: 3, internal sense: 5'-AAA GGC GAG ATC AGC GTC AAC GTG CTC AAG-3', SEQ. ID. NO: 4, internal antisense: 5'-CTT GAG CAC GTT GAC GCT GAT CTC GCC ATT-3') using a DNA polymerase (pfu polymerase (Vent), New England Bioscience, USA) at 94° C. for 4 minutes, denaturation at 94° C. for 1 minute, annealing at 55° C. for 1 minute, polymerization at 72° C. for 1 minute, 30 cycles from denaturation to polymerization, and final extension at 72° C. for 5 minutes.

The 293 cell line was transfected with the expression vector pcDNA/HA-VHL harboring a neomycin-resistant gene by calcium phosphate method, which was then cultured in a selection medium (LDMEM containing 1 mg/ml of neomycin). From the culture, cell colonies expressing HA-VHL (293-HA-VHL cell line) were obtained for further use.

<2-1> Decrease of VHL Stability by UCP

Figure 9:
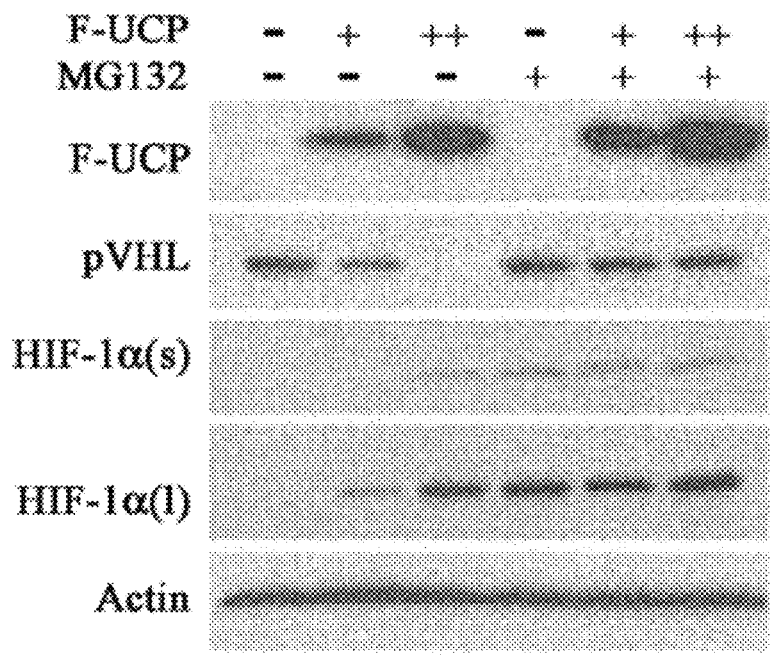
FIG. 9 is a photograph of Western blotting illustrating that the over-expressed UCP targets endogenous VHL for degradation by 26S proteasome and thereby stabilizes HIF-1α.
Figure 10:
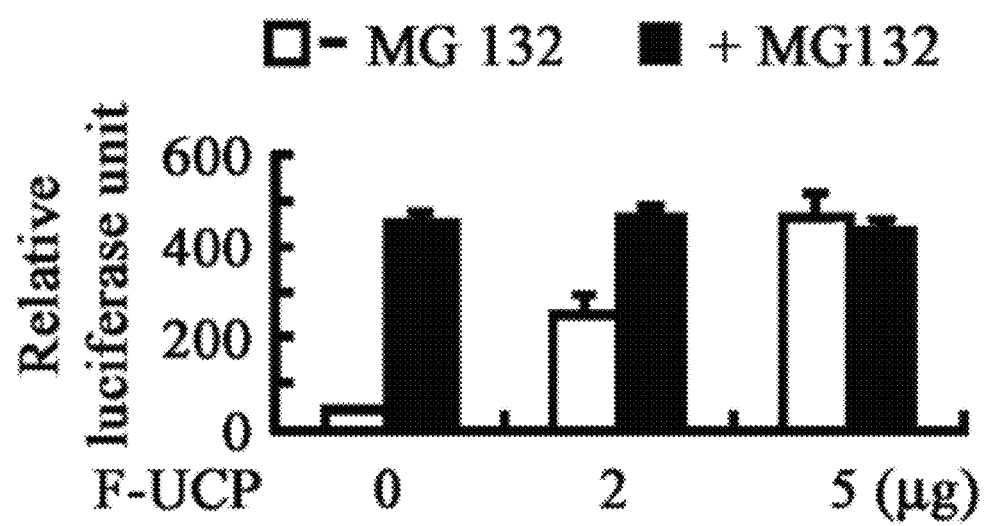
FIG. 10 is a graph illustrating that an activity of a reporter gene under the transcriptional control of hypoxia response element (HRE) is measured. The increase of HIF-1α induced the increase of HRE-reporter activity in UCP over-expressing cells.

HEK293T cells were transfected with 10 µg and 15 µg of Flag-UCP expression vector by calcium phosphate method respectively. 12 hours before harvest, the cells were treated with 10 µM of MG132 (26S proteasome inhibitor) or not treated. The harvested cells were frozen at −70° C. and then lysed in a cell lysis buffer (50 mM Tris, 0.5 mM EDTA, 50 mM KCl, 10% Glycerol, 1 mM DTT, 0.5% NP-40, 0.5 mM PMSF). Western blotting was performed with the lysates using mouse anti-Flag antibody, mouse anti-VHL antibody, mouse anti-HIF-1α (Pharmingen) antibody and mouse anti-β-actin antibody (Sigma). As a result, VHL level was reduced with the increase of UCP expression, which was inhibited by MG132. The level and transcription activity of HIF-1α were UCP content-dependently increased (FIG. 9 and FIG. 10). The above results indicate that UCP degrades VHL by 26S proteasome.

Figure 11:
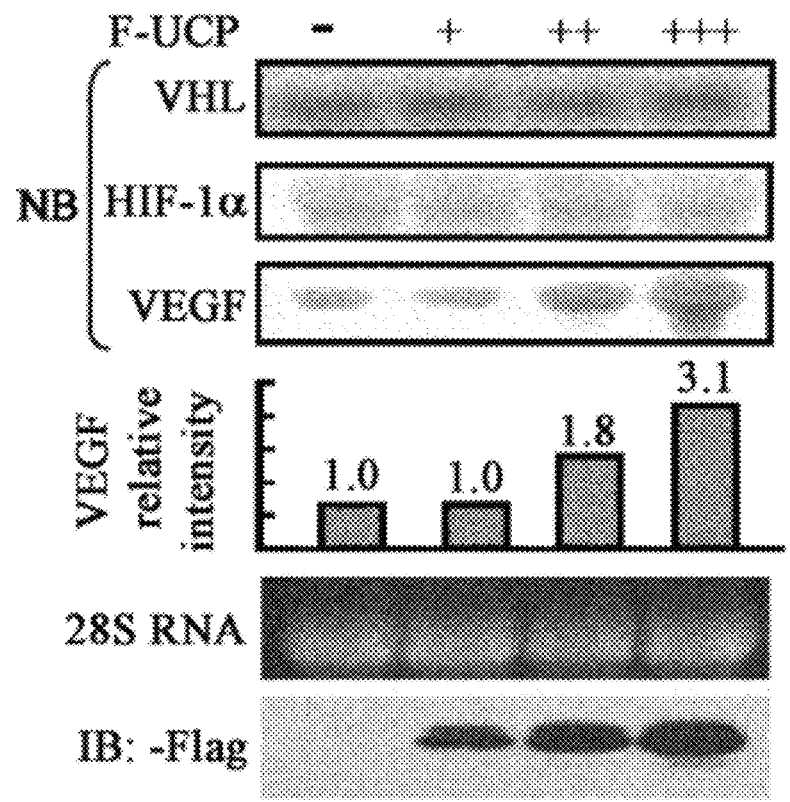
FIG. 11 is a photograph of Northern blotting illustrating that UCP did not affect the expressions of VHL and HIF-1α mRNAs but stabilized HIF-1α, which increased the expression of vascular endothelial growth factor (VEGF).

To prove the decrease of VHL level by UCP was post-translational level, the level of VHL mRNA in the presence of Flag-UCP was measured by Northern blotting. The levels of HIF-1α and VEFG mRNA, a target molecule of HIF-1α, were also measured. Total RNA was extracted from HEK293 cells transfected with 5, 10, and 15 µg of F-UCP by using RNasey kit (Qiagen). 25 µg of RNA was electrophoresed on formalin agarose gel, and then transferred onto a nylon membrane to be adhered thereon. Northern blotting was performed using the same. VHL, HIF-1α, VEGF, Actin cDNAs were radio-labeled with [$^{32}$P]dCTP using DNA labeling kit (Amersham/Pharmacia), followed by reaction with the nylon membrane at 65° C. for 16 hours. The remaining radio-labeled probes were washed out. The membrane was tested with BAS1500 (Fuji) PhosphorImager. As a result VHL and HIF-1α transcriptions were not affected by F-UCP but VEGF transcription was increased by F-UCP (FIG. 11).

From the results, it was confirmed that UCP reduced VHL protein at post-translational level, which forms a part of E3 ubiquitin ligase complex targeting HIF-1α for degradation. Accordingly, intracellular HIF-1α protein level was increased and thus promoted VEGF expression at transcriptional level.

<2-2> Changes of Endogenous VHL Level by UCP Under the Hypoxic Condition

The following experiment was performed to investigate the changes of endogenous VHL level by UCP in the hypoxic (1% $O_2$) and normoxic (20% $O_2$) conditions.

Figure 15A:
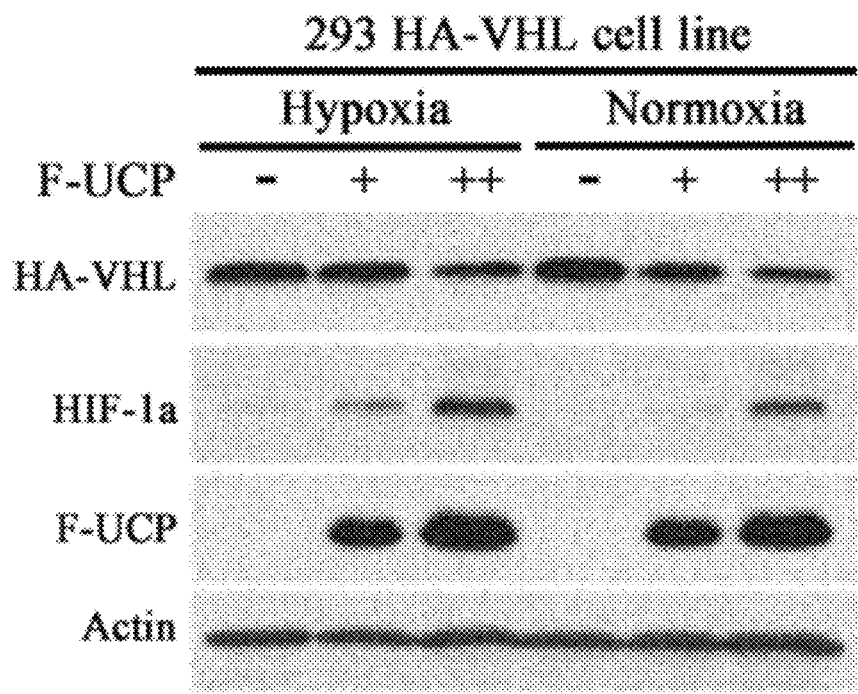
FIG. 15a is a photograph of Western blotting illustrating that VHL protein was decreased but HIF-1α protein was increased UCP-expression dependently when UCP over-expressing cells were cultured in normoxic and hypoxic conditions.

Ten and fifteen µg of Flag-UCP were transfected into 293-HA-VHL cells by calcium phosphate method. 24 hours later, the cells were transferred to a hypoxic chamber and incubated for 12 hours before harvest (hypoxic condition). After harvest, the cells were frozen at −70° C. and lysed in a cell lysis buffer. Western blotting was performed with the lysate using mouse anti-HA epitope antibody (Roche), mouse anti-Flag antibody, mouse anti-HIF-1α antibody and mouse anti-β-actin antibody. As a result, HA-VHL level was reduced with the increase of Flag-UCP expression in both hypoxic and normoxic conditions, indicating that endogenous HIF-1α was stabilized thereby (FIG. 15a).

Figure 15B:
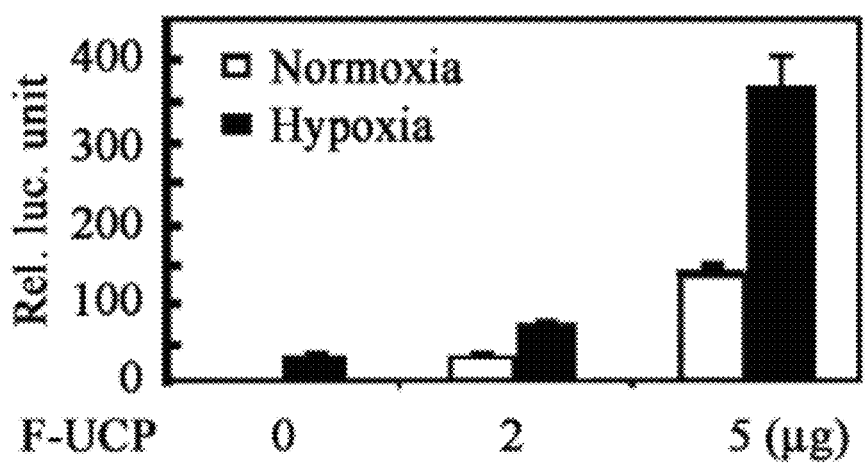
FIG. 15b is a graph illustrating the result of HRE reporter assay under the hypoxic conditions as described in FIG. 15a that the increase of HIF-1α protein level by UCP over-expression in cells induced the increase of HRE-reporter activity.

The functionality of the stabilized HIF-1α was confirmed once again by reporter assay using HRE-luc. HRE-luc was co-transfected with 5 µg and 10 µg of F-UCP expression vector into HEK293 cells cultured in a 6 well plate. The cells were left in a hypoxic chamber for approximately 16 hours before harvest (hypoxic condition). The harvested cells were frozen at −70° C. and then lysed in a reporter cell lysis buffer (Promega), to which luminal, a luciferase substrate, was added to measure the luciferase activity. As a result, HRE-luc activity was F-UCP dose-dependently increased (FIG. 15b). The above result indicates that UCP reduces endogenous VHL level which regulates endogenous HIF-1α under both hypoxic and normoxic conditions.

<2-3> Auto-Ubiquitination (E2/E3) Activity of UCP

Figure 16:
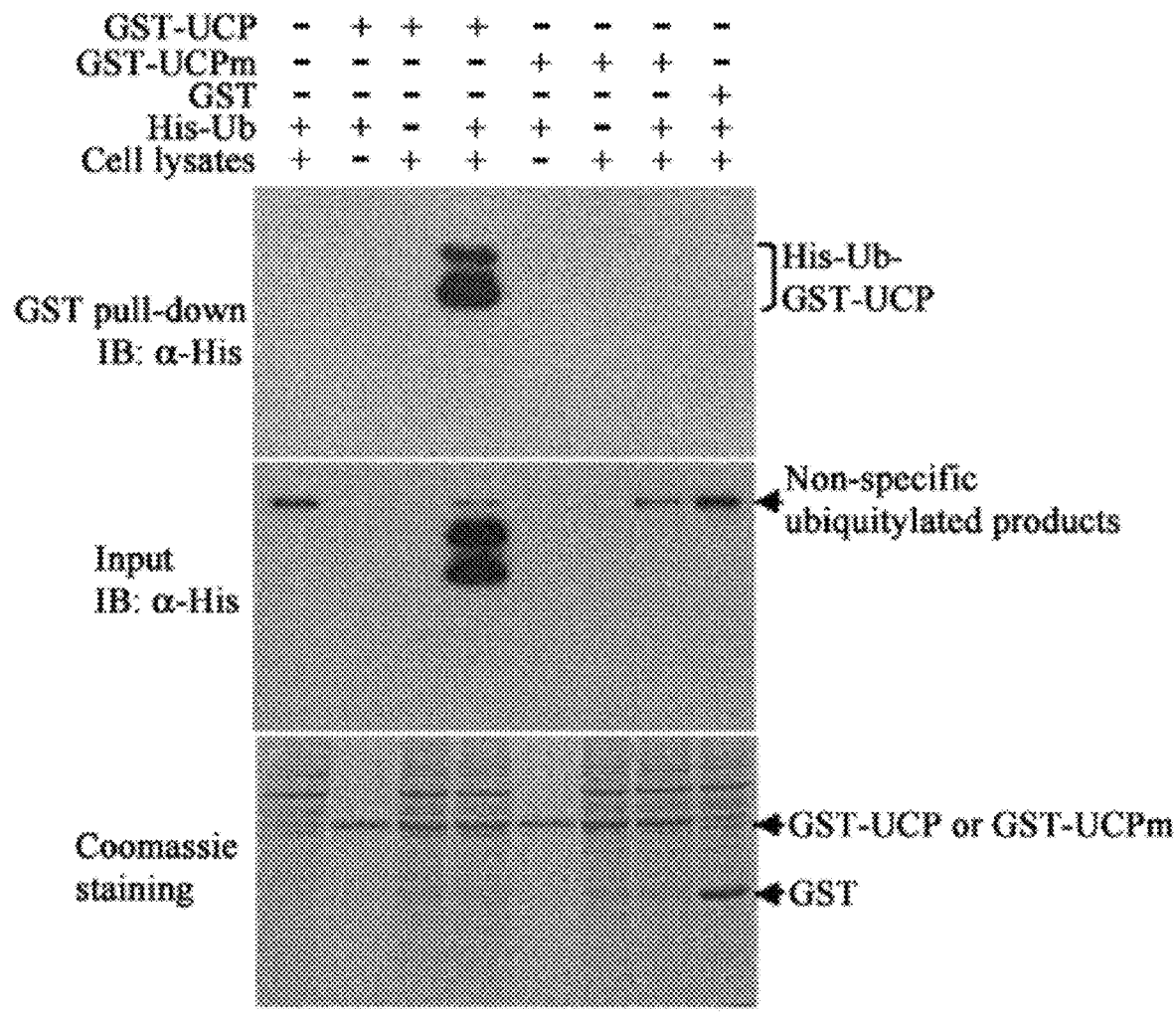
FIG. 16 is a photograph of Western blotting illustrating that wild type UCP exhibits enzyme activity but the mutant UCPm with the substitution of the $95^{th}$ cysteine with serine does not exhibit enzyme activity.

UCP is known as an E2 ubiquitin conjugating enzyme, which has an E3 ubiquitin ligase activity as well. The 95$^{th}$ amino acid of UCP 'cysteine' is well conserved in E2 family and plays an important role in ubiqutin conjugating enzyme activity (EMBO J. 22, 5241-5250, 2003). Thus, the present inventors investigated the role of E2 enzyme activity in regulation of endogenous VHL level by UCP. To do so, a wild type GST-UCP and the mutant GST-UCPm with the substitution of the 95$^{th}$ cysteine with serine were expressed in E. coli respectively and then isolated/purified. Cell lysate (S-100) of 786-0 cells (American Type Culture Collection: ATCC) was used as an E1 source. Each protein was mixed in ubiquitination buffer (50 mM Tris, 1 mM ATP, 10 mM creatine phosphate, 10 µg creatine phosphokinase, 0.5 mM DTT, 5 mM $MgCl_2$, 1 µg ubiquitin aldehyde, 1 µg His-ubiquitin), followed by reaction at 37° C. for 1 hour and then GST-pull down. Ubiquitinated UCP was screened by Western blotting using anti-His antibody and as a result auto-ubiquitination was detected only in the wild type GST-UCP (FIG. 16).

<2-4> Association of UCP Enzyme Activity with UCP Mediated VHL Degradation

Figure 12:
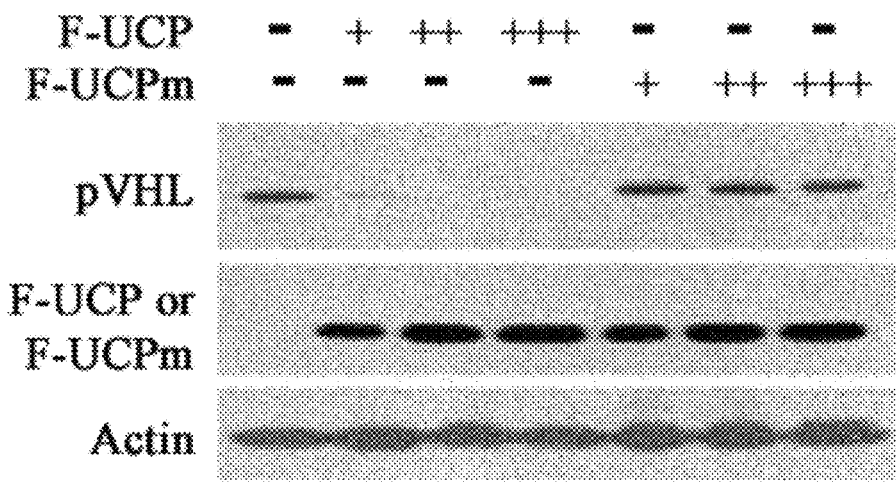
FIG. 12 is a photograph of Western blotting illustrating UCP enzyme activity dependent VHL protein reduction.

Flag-UCP and Flag-UCPm expression vectors were respectively transfected into HEK293T cells at different concentrations (5, 10, 15 µg). 48 hours later, the cells were recovered, frozen at −70° C. and lysed in a cell lysis buffer. Western blotting was performed with the lysate using mouse anti-VHL, mouse anti-Flag and mouse anti-actin antibodies. As a result, VHL level was reduced Flag-UCP concentration-dependently but not affected by Flag-UCPm, indicating that UCP enzyme activity is required for VHL protein degradation by UCP (FIG. 12).

Example 3

Multiubiquitination of VHL by UCP

To verify that the decrease of endogenous VHL by UCP was attributed to ubiqitin-mediated proteolysis, multiubiquitination of VHL was investigated. In vivo and in vitro VHL ubiquitination assays were performed. UCP and UCPm were cloned into pGEX4T-1 vector by using EcoR1/NotI, which were expressed in E. coli DH5α. GST-UCP and GST-UCPm were purified by glutathione-sepharose resin. Flag-VHL expression vector was transfected into HEK293 cells and expressed therein, followed by Flag-agarose gel immunoprecipitation to isolate Flag-VHL only.

<3-1> In Vivo VHL Ubiquitination by UCP

Figure 13:
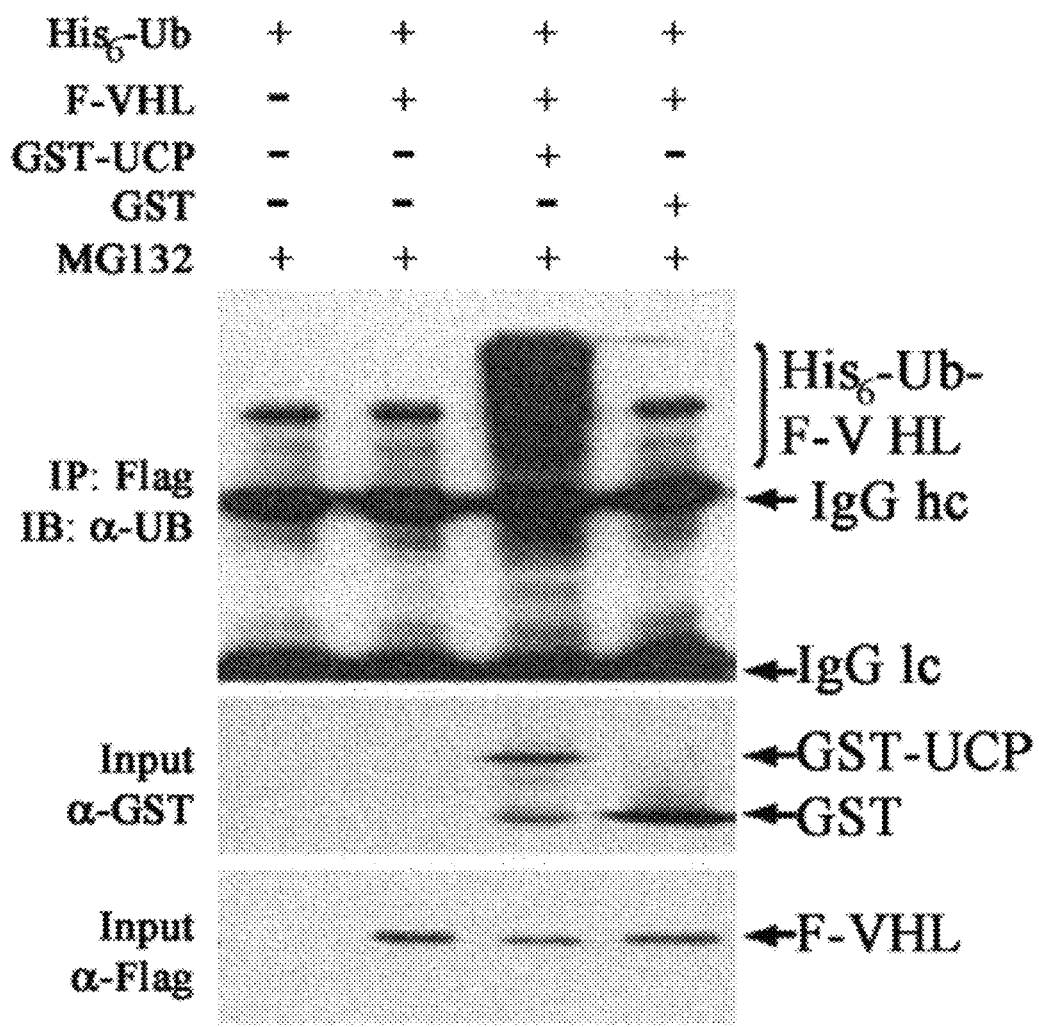
FIG. 13 and FIG. 14 are photographs of Western blotting illustrating UCP mediated VHL multiubiquitinations in culture cells and in vitro.

HEK293 cells were transfected with His-Ub expression vector by calcium phosphate method and cultured. The cells were equally distributed in 100 mm culture dishes and cultured, to which the expression vectors indicated in FIG. 13 were transfected. 12 hours before harvest, the cells were treated with 10 µM of MG132. The harvested cells were lysed in a denatured lysis buffer (50 mM Tris, 1% SDS, 4 M Urea) by ultrasonicator. Flag antibody-cojugated agarose was added to the cell lysate, followed by immunoprecipitation at room temperature for 2 hours. Western blotting was performed using mouse anti-Ub antibody. Some of the cell lysate was taken before immunoprecipitation, with which Western blotting was performed using mouse anti-GST and mouse anti-Flag antibodies by the same manner as the above. As a result, multiubiquitination of Flag-VHL by UCP was detected (FIG. 13).

<3-2> In Vitro VHL Ubiquitination by UCP

Figure 14:
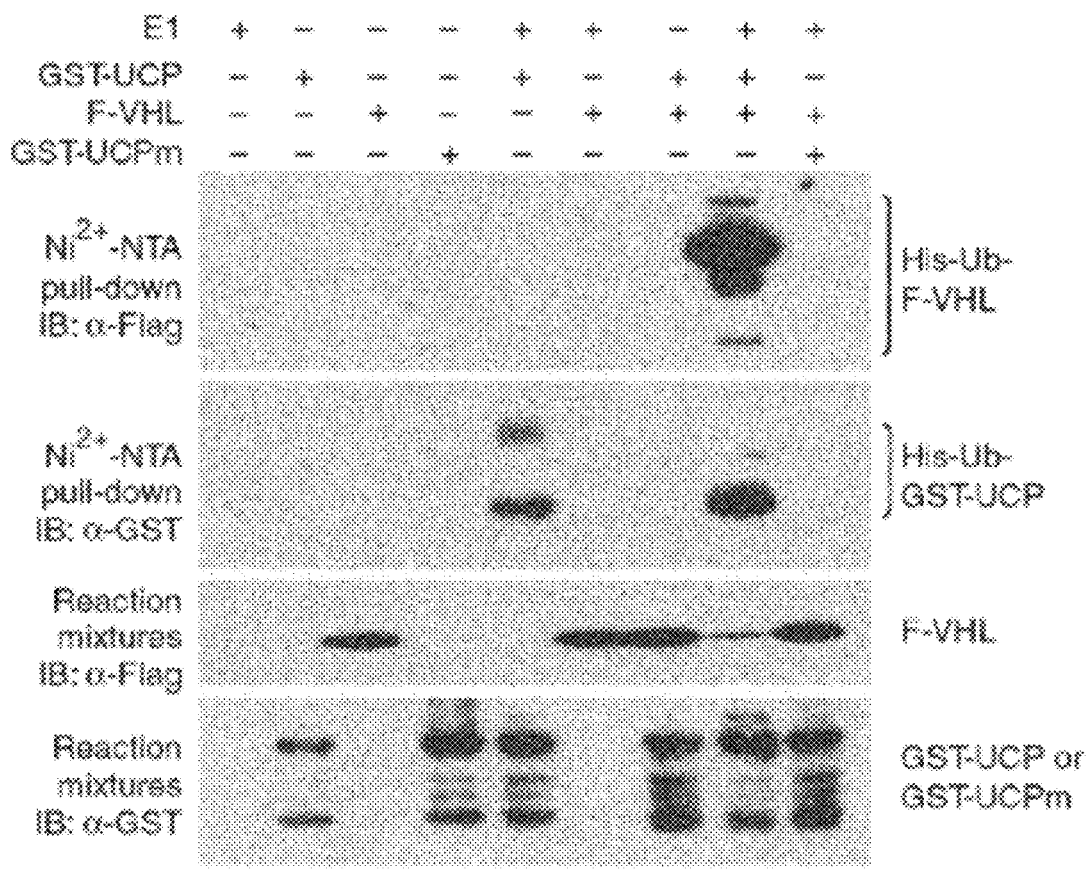

1 μg of E1 (Rabbit, Sigma), purified GST-UCP and GST-UCPm and Flag-VHL were mixed in the ubiquitination buffer, followed by reaction at 37° C. for one hour. The mixture was precipitated with $Ni^{2+}$-NTA resin at 4° C. for 2 hours, followed by Western blotting using mouse anti-Flag antibody and mouse anti-GST antibody. And 1/10 of the reacted sample was taken before $Ni^{2+}$-NTA resin (QIAGEN, GERMANY) pull-down, with which Western blotting was performed using anti-Flag antibody and mouse anti-GST antibody. As a result, in vitro ubiquitination of VHL by UCP was detected (FIG. 14).

To further verify the VHL ubiquitination by UCP, 1 μg of E1, purified GST-UCP and GST-UCPm, and Flag-VHL were mixed in the ubiquitination buffer, followed by reaction at 37° C. for 1 hour. Western blotting was performed using mouse anti-Flag, mouse anti-His and mouse anti-GST antibodies. The reaction solution was precipitated using Anti-Flag-agarose and $Ni^{2+}$-NTA resin respectively at 4° C. for 2 hours, followed by Western blotting using mouse anti-Flag, mouse anti-His and mouse anti-GST antibodies. As a result, VHL ubiquitination directly catalyzed by the wild type UCP was detected in vitro (FIGS. 17a and b).

The above results indicate that UCP functions as an E2 ubiquitin carrier and an E3 ubiquitin ligase, so that UCP ubiquitinates VHL and thereby induces degradation of the protein via 26S proteasome. That is, UCP has both E2 and E3 enzyme activities.

Example 4

Specificity of UCP to VHL Stability

The present inventors investigated if UCP targets other proteins for degradation or specifically targets VHL for degradation. That is, the inventors investigated if UCP ubiquitinates VHL specifically for degradation. To do so, GST-UbCH5C and GST-CDC34 were digested with BamHI/NotI and cloned into pEBG vector.

<4-1> The Effect of UCP on Stability of Elongin B, Elongin C and Rbx 1

Ten μg of Flag-UCP expression vector was transfected into HEK293T cells by calcium phosphate method and the cells were frozen at −70° C. The cells were lysed in a cell lysis buffer. Western blotting was performed by the same manner as described above using mouse anti-Flag antibody, mouse anti-VHL antibody, rabbit anti-Elongin B, rabbit anti-Elongin C antibody, rabbit anti-Rbx1 antibody and mouse anti-β-actin antibody. As a result, VHL protein level was significantly reduced by UCP and Elongin B and C levels were slightly reduced (FIG. 18a). The less decrease of Elongin B and C levels by UCP was presumably because VHL, Elongin B and Elongin C formed a complex so that each protein therein became more stabilized (PNAS USA 97, 8507-8512, 2000). In other words, the slight decrease of Elongin B and Elongin C was assumed to result from the significant decrease of VHL level and thereby a reduction of half-lives of independent Elongin B and Elongin C.

<4-2> The Effect of UCP on the Stability of SOCS1 and MDM2

Elongin B and C form a complex with SOCS1 (suppressor of cytokine signaling 1) to inhibit the degradation of SOCS1 (Genes & Development 12, 3872-3881, 1998). In the meantime, SOCS1 forms a complex with Elongin B, Elongin C and Cul2 and thus exhibits E3 ubiquitin ligase activity similar to VHL E3 ubiquitin ligase (JBC 275, 14005-14008, 2000). Thus, the present inventors further examined if UCP induced the degradation of SOCS1. HEK293 cells were transfected with Flag-VHL and Flag-SOCS1 expression vectors respectively by calcium phosphate method, which were equally distributed in a 6 well-plate. After culturing for 24 hours, GST-UCP and GST expression vectors were introduced into the cells by the same manner as the above. 24 hours later, the cells were recovered and frozen at −70° C. The frozen cells were lysed in a cell lysis buffer. Western blotting with the lysate was performed by using mouse anti-Flag, mouse anti-GST, and mouse anti-actin antibodies by the same manner as described above. As a result, UCP did not affect the stability of SOCS1 and only reduced Flag-VHL (FIG. 18b).

MDM2 is a protein having a RING finger structure and induces MDM2 autoubiquitination and p53 ubiquitination (JBC 275, 8945-8951, 2000). Such E2 enzymes as UbCH5c and E2-25K induce MDM2 autoubiquitination (JBC 279, 42169-42181, 2004). Based on the foundings, the present inventors investigated whether UCP, as an E2 enzyme, could regulate endogenous MDM2 in the liver cancer cell line JSHC. UbCH5C was used as a positive control. JSHC cells cultured in a 100 mm culture dish were transfected with 10 μg of GST-UbCH5c, GST-UCP and GST expression vectors by calcium phosphate method. 48 hours later, the cells were harvested and lysed in an immunoprecipitation buffer solution (50 mM Tris, 150 mM NaCl, 1% NP-40, 0.5% deoxycholate, 0.1% SDS). Western blotting with the lysate was performed using mouse anti-MDM2 antibody (Pharmingen), mouse anti-GST antibody, and mouse anti-actin antibody. As a result, UbCH5C reduced MDM2 protein level, while UCP did not change MDM2 level (FIG. 18c).

<4-3> VHL Stability by UCP and Rbx1

Figure 19A:
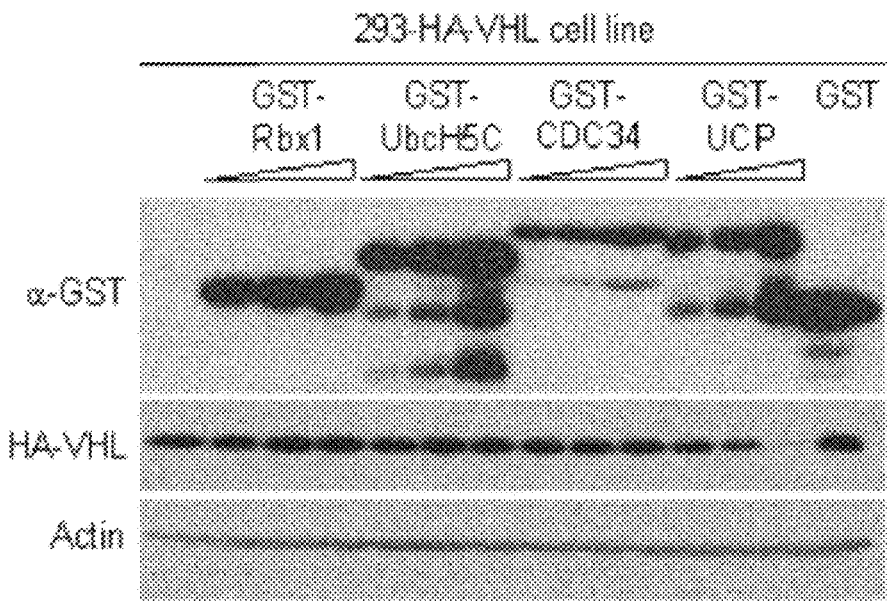
Figure 19B:
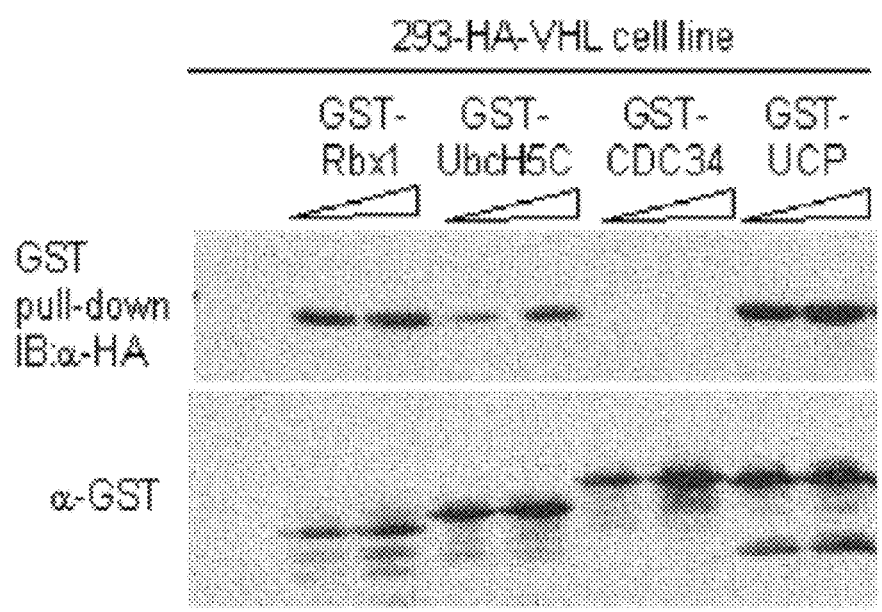

Rbx1 induces VHL ubiquitination in vitro in the absence of Elongin B and Elongin C, but dose not induce Ubc5H mediated VHL ubiquitination in the presence of Elongin B and Elongin C (JBC 277, 30338-30393, 2002). CDC34 forms a protein complex with Skp1-Cul1 and thus exhibits E3 ubiquitin ligase activity. This complex is similar in structure to VHL E3 ubiquitin ligase (Curr Biol 9, 1180-1182, 1999) and induces ubiquitination of CDC4, an F-box protein, in vitro (JBC 277, 30338-30393, 2002). 293-HA-VHL cells were transfected with GST-Rbx1, GST-UbCH5C, GST-CDC34 and GST-UCP expression vectors by calcium phosphate method. The transfected cells were collected and lysed in a cell lysis buffer. Western blotting was performed with each lysate using mouse anti-HA antibody and mouse anti-GST antibody by the same manner as described above. Interaction between each molecule with VHL was also investigated by GST-pull down assay. As a result, GST-Rbx1 and GST-UbCH5C interacted with VHL but did not reduce VHL level. In the meantime, CDC34 neither interact with HA-VHL nor affect the stability of HA-VHL. Only GST-UCP reduced HA-VHL (FIG. 19).

The above results indicate that UCP targets specifically VHL to induce ubiquitin-mediated proteolysis.

Example 5

Decrease of VHL Expression by UCP in Mouse Liver Tissue

Whether VHL protein degradation by UCP detected in vitro culture cells was equally observed in vivo was investigated. To do so, the adenoviral vector expressing Flag-UCP was constructed by cloning Flag-UCP into the NotI/XbaI site of pCMV shuttle vector (QUANTUM biotechnology), which was co-introduced with pAdEasy-1 containing the adenovirus genome into E. coli BJ5183, resulting in the construction of Ad.F-UCP virus. The method for constructing the recombinant adenovirus is precisely described in the previous patent description (Invention Title: Small Interfering RNA Specific for PTTG1, Expression Vector thereof and Therapeutic Agent for Tumor Comprising the Same; Application Date: 2005 Mar. 4; Korean Patent Application No.: 2005-18140).

Particularly, $2\times10^8$ plaque-forming unit (pfu) of purified Ad.F-UCP or Ad.GFP (as a control) virus were injected into the tail vein of female Balb/c mice at 6 weeks, and PBS alone was also injected thereto (3 mice per each experimental group). 3 days later, the mouse liver was excised and the tissues were crushed in a mortar containing liquid nitrogen. In the meantime, frozen sections were also prepared.

Figure 20:
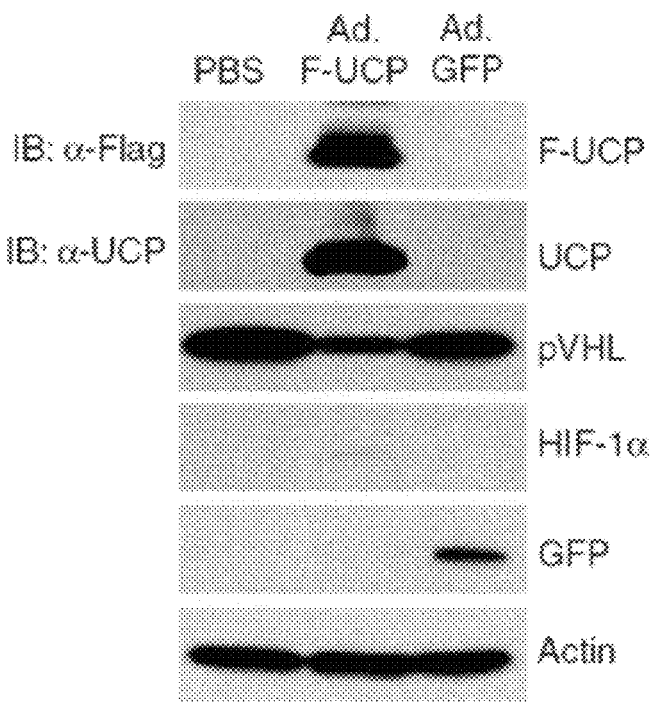
FIG. 20 is a photograph of Western blotting illustrating that Ad.F-UCP is injected into the mouse liver, resulting in the decrease of VHL protein but the increase of HIF-1α protein.

Cell lysate for Western blotting was prepared with the crushed liver tissues in liquid nitrogen using a mammalian proteasome extraction kit (Calbiochem, USA). Western blotting was performed with the cell lysate using anti-Flag, anti-UCP, anti-VHL, anti-HIF-1α antibodies by the same manner as described above. As a result, UCP over-expression reduced VHL level but increased HIF-1α (FIG. 20). The endogenous UCP was not detected in the mouse liver tissues.

Figure 21:
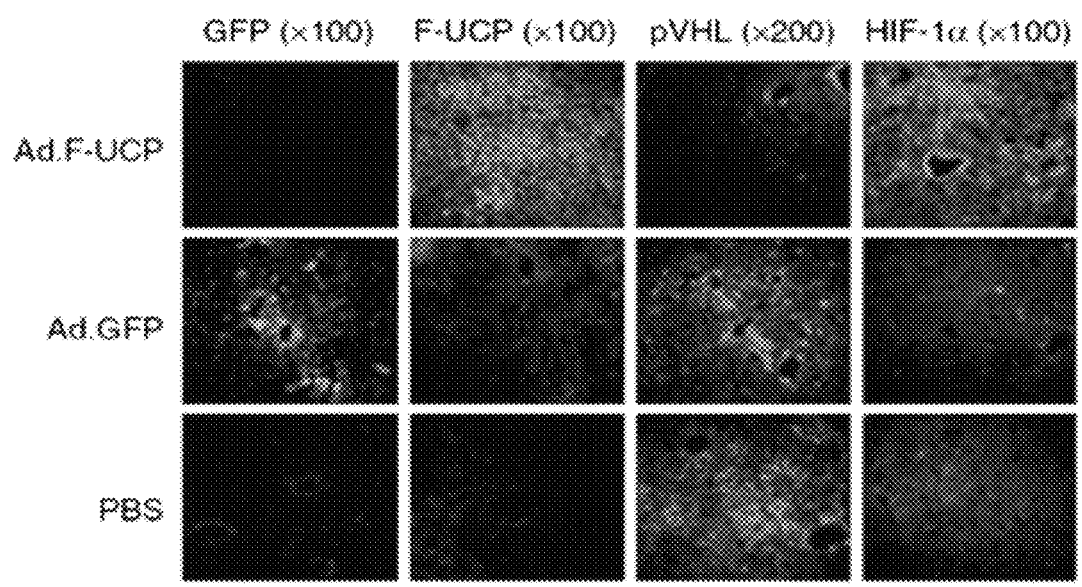
FIG. 21 is immunofluorescent photographs illustrating the mouse liver tissues under the conditions as indicated in FIG. 20.

Immunohistochemical staining with the liver tissues prepared on a slide was performed for detecting Flag-UCP, VHL and HIF-1α. The slide adhered each section of the tissue was blocked with PBS containing 1% FBS at room temperature for one hour, followed by reaction with PBS containing 0.1% FBS and each antibody at 37° C. for one hour. After washing with PBST three times for 5 minutes, reaction with 0.1% FBS PBS containing anti-mouse IgG was induced at room temperature for 30 minutes. Then, the remaining antibodies were eliminated by washing with PBST three times for 5 minutes. Reaction to each antibody in every tissue was observed under fluorescent microscope. As a result, Flag-UCP expression reduced VHL level but increased HIF-1α level (FIG. 21), suggesting that the decrease of VHL level by Flag-UCP was equally observed in vivo and in vitro.

<5-1> UCP, VHL and HIF-1α Expressions in Cancer Patient Tissues

Figure 22:
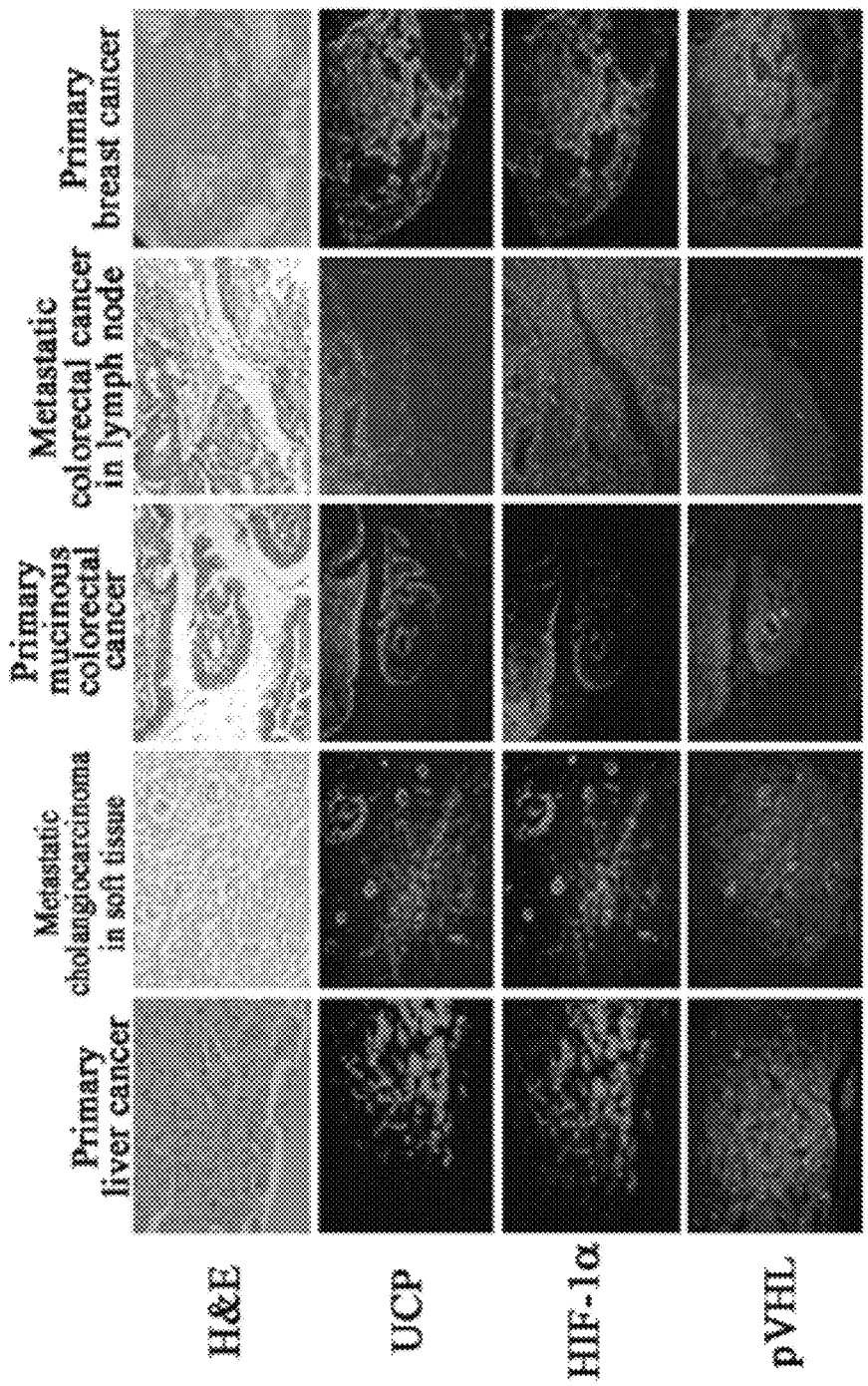
FIG. 22 is hematoxylin & eosin (H&E) staining and immunofluorescent photographs illustrating that UCP and HIF-1α are co-expressed more abundantly in such human cancer cells as liver cancer, metastatic cholangiocarcinoma, colorectal cancer, metastatic colorectal cancer, and breast cancer cells but VHL expression is reduced therein.

Immunohistochemical staining with tissue array slide (See internet address tissue-array.com, SuperBioChips Lab) placed tissues of liver cancer, colorectal cancer, and breast cancer patients was performed using UCP, VHL and HIF-1α antibodies by the same manner as described above. As a result, UCP was highly co-expressed with HIF-1α in primary cancer tissues and metastatic cancer tissues, while VHL was hardly detected (FIG. 22). The fact that high expressions of UCP and HIF-1α were detected in the oxygen abundant regions of cancer tissues indicates that the decrease of VHL level by UCP stabilizes HIF-1α so that it might play a certain role in tumor growth and metastasis.

Example 6

UCP Functions Associated with Tumor Cell Growth and Invasion/Metastasis

The above results indicate that UCP targets VHL, one of tumor suppressor proteins, for degradation. These results also support the presumption that UCP plays an important role in tumor progression and metastasis, and thus UCP is a new molecular target for the treatment of cancer. The present inventors investigated the expressions of UCP and VHL in various cancer cells to examine the effect of UCP over-expression and/or inhibition on tumor cell growth and invasion/metastasis.

<6-1> UCP and VHL Expressions in Various Cancer Cell Lines

Figure 23:
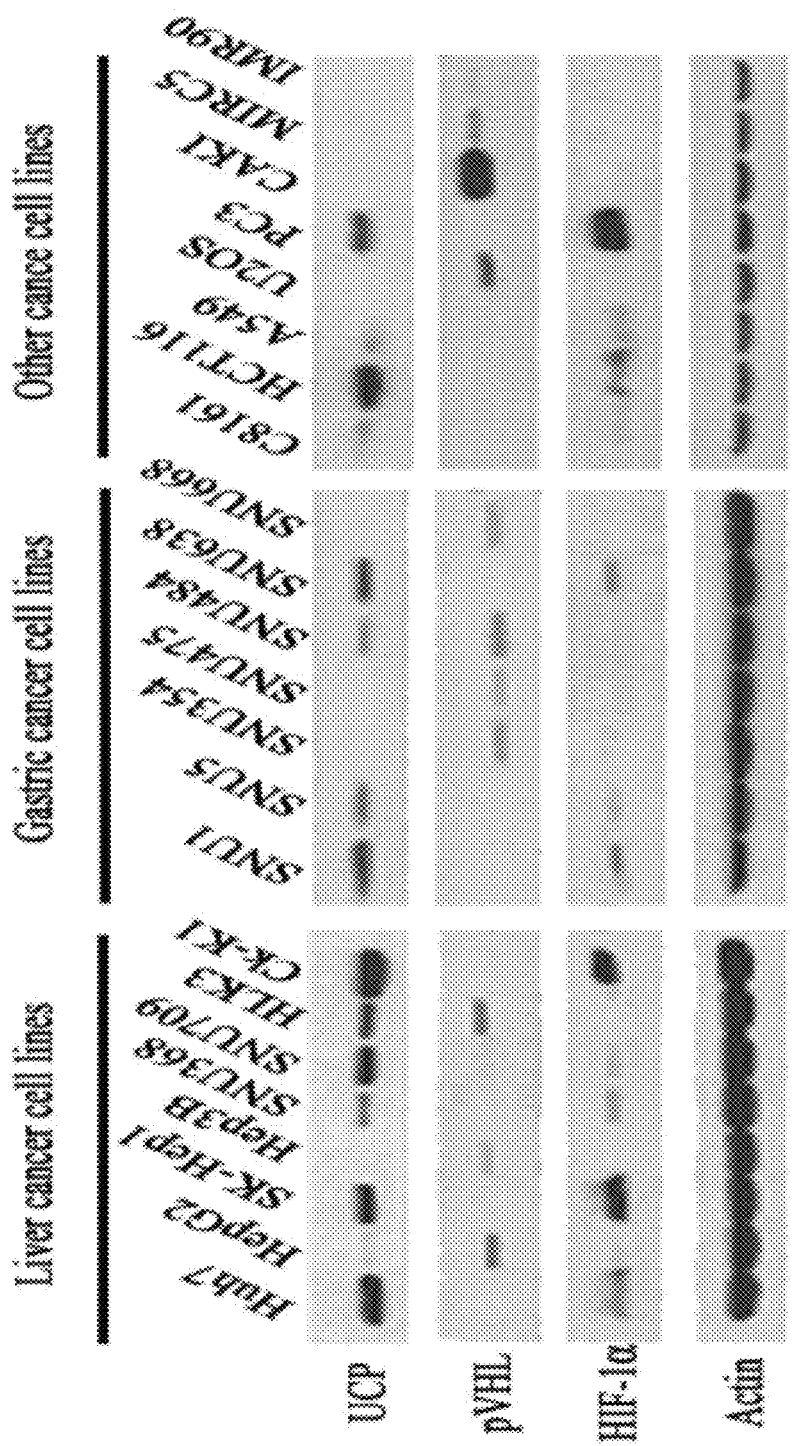
FIG. 23 is a photograph of Western blotting illustrating that UCP level is in reverse proportion to VHL protein level in various cancer cell lines.

Seven liver cancer cell lines (ATCC, SNU368, SNU709, Korean Cell Line Bank, Cancer Research Institute, Seoul National University College of Medicine), a cholangiocarcinoma cell line (Ck-K1) (Prof. DG Kim, Chonbuk National University Medical School), 7 stomach cancer cell lines (Korean Cell Line Bank, Cancer Research Institute, Seoul National University College of Medicine), a skin cancer cell line (C8161) (Dr. J H Lee, Korea Research Institute of Bioscience and Biotechnology), colon cancer cell line (HCT116) (ATCC), a lung cancer cell line (A549) (ATCC), an osteosarcoma cell line (U2O5) (ATCC), a prostate cancer cell line (PC3) (ATCC), a kidney cancer cell line (CAKI) (ATCC) and 2 normal fibroblast cell lines (MRC5 and IMR90 (ATCC)) were cultured in 100 mm culture dishes containing HDMEM (containing 4.5 g/l glucose, 10% FBS, 100 unit/ml penicillin and 100 μg/ml streptomycin) at the concentration of $10^6$ cells per dish for 24 hours under normoxic condition. The cells were harvested, frozen at −70° C. and lysed in a cell lysis buffer. Western blotting was performed with the lysate using mouse anti-UCP antibody, mouse anti-VHL antibody, and mouse anti-actin antibody. As a result, UCP expression was in reverse proportion to VHL level in almost every cell lines except HLK3, a liver cancer cell line (FIG. 23). Even though HIF-1α level was not exactly in proportion to UCP level, HIF-1α was co-detected with UCP in 12 out of 15 cell lines. This result indicates that UCP expression affects HIF-1α stability under normoxic condition.

<6-2> The Effect of UCP Over-Expression on Tumor Cell Growth and Invasion

Figure 24:
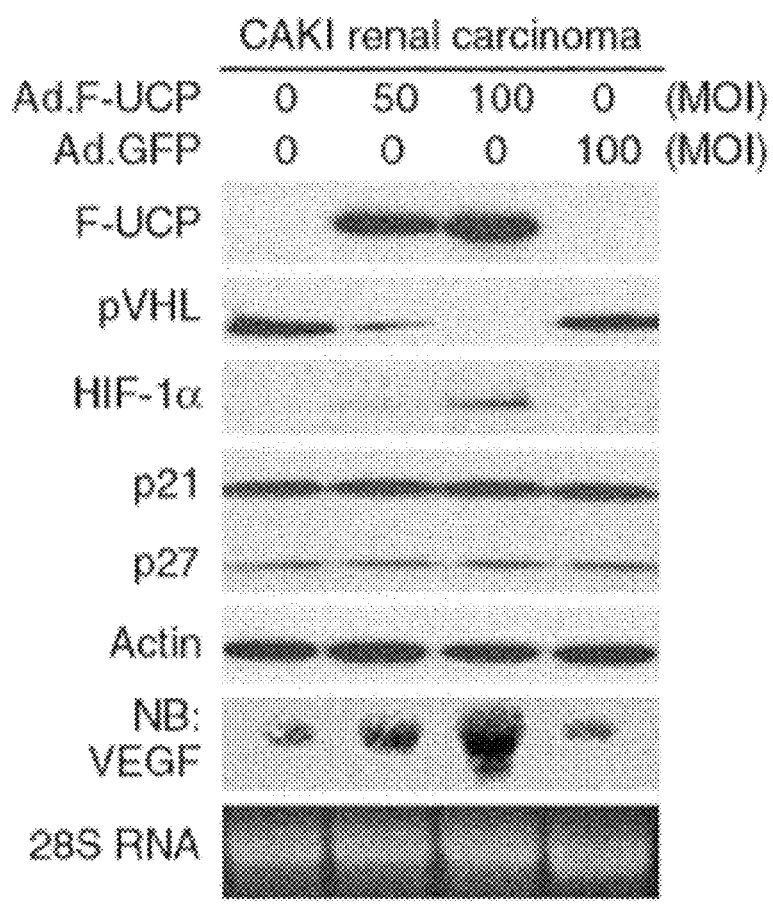
FIG. 24 is a photograph of Northern blotting illustrating that UCP over-expression by Ad.F-UCP in CAKI kidney cancer cells expressing low UCP expression and high VHL expression results in the decrease of VHL level and the increase of HIF-1α level, and thereby results in the increase of VEGF expression.

CAKI, the kidney cancer cell line, was infected with a Flag-UCP containing adenovirus (Ad.F-UCP, 50, 100 multiplicity of infection: MOI) and a GFP containing control virus (Ad.GFP, 100 MOI). 48 hours later, the cells were harvested, frozen at −70° C. and lysed in a cell lysis buffer. Western blotting was performed with the lysate using mouse anti-Flag, mouse anti-VHL, mouse anti-HIF-1α, mouse anti-p21, mouse anti-actin p27, and mouse anti-actin antibodies. The level of VEGF mRNA was investigated by Northern blotting using [$^{32}$P]dCTP-labeled actin VEGF cDNAs by the same manner as described above. As a result, UCP over-expression in CAKI cells expressing VHL at high level reduced VHL level, and thereby increased HIF-1α and VEGF expressions (FIG. 24). The levels of p21 and p27 proteins were not changed, suggesting that UCP regulates specifically VHL-HIF pathway (FIG. 24).

Figure 25:
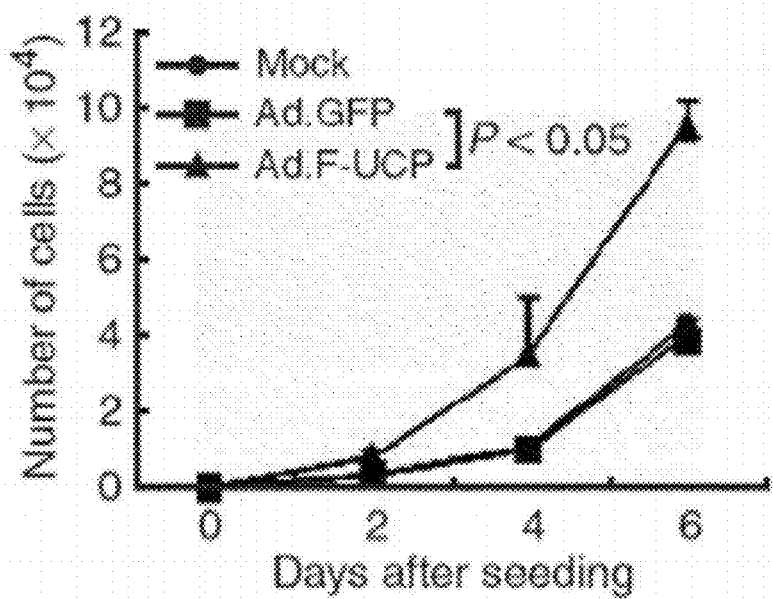
FIG. 25 is a graph illustrating that UCP over-expression by Ad.F-UCP enhances prolieration of CAKI kidney cancer cells.
Figure 26:
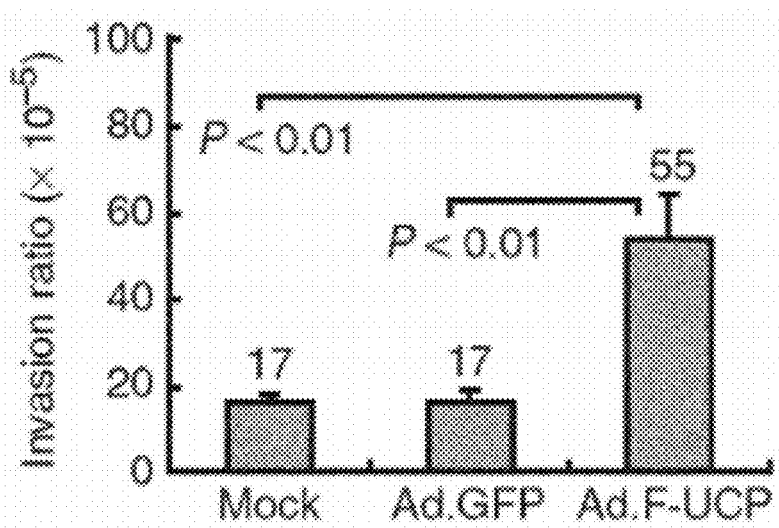
FIG. 26 is a graph illustrating that UCP over-expression promotes invasion of CAKI kidney cancer cells.

CAKI, the kidney cancer cell line, was infected with Ad.F-UCP and Ad.GFP as a control by 50 MOI for each and the cells treated with PBS was used as a control. 16 hours later, the cells were distributed by 100 cells per well and incubated. The number of cells of each well was counted with a hemacytometer at two day intervals. UCP over-expression increased cell growth rate approximately at least two-fold (FIG. 25). Invasion assay was also performed. CAKI cells were infected with Ad.F-UCP and Ad.GFP respectively by 50 MOI and the cells treated with PBS was used as a control. 16 hours later, $10^4$ cells were distributed in a trans-well (Costar) coated with matrigel (BD), followed by culture for 24 hours in HDMEM (4.5 g/l glucose, 10% FBS, 100 μg penicillin/streptomycin). Cells that had been passed through the trans-well were stained with haematoxylin-eosin and counted. As a result, UCP over-expression increased invasion rate up to 3 fold, compared with a control (FIG. 26).

<6-3> The Effect of UCP Depletion by siRNA on Tumor Cell Growth and Invasion

The previous experiment confirmed that UCP expression was significantly high in the skin cancer cell line C8161 associated with metastasis to lung (FIG. 23). To inhibit UCP expression, the present inventors generated siRNA and constructed adenovirus encoding UCP-siRNA (Ad.UCP-siRNA). The nucleotide sequence of UCP-siRNA was prepared by cloning 615-633 nucleotide region of UCP mRNA represented by SEQ. ID. NO: 6 into HindIII/Bg/II site of pSuper plasmid vector (OligoEngine, USA) so as to be expressed by H1 promoter later. The pSuper plasmid vector was digested with XbaI/HindIII, and the resulting DNA fragment containing H1 promoter, the sequence for UCP-siRNA, and $T_5$ transcription termination sequence, was introduced into the adenoviral pShuttle vector (BD Bioscience, USA) carrying and expressing a target gene (pShuttle/UCP-siRNA). The pShuttle/UCP-siRNA and an adenovirus gene containing pAdEasy-1 were introduced into E. coli BJ5183 strain to prepare a recombinant vector. Adenovirus particles were prepared by using the above UCP-siRNA containing adenoviral vector by the same manner as described in Example 5. The control virus (Ad.Con-siRNA), Con-siRNA represented by SEQ. ID. NO: 7, was prepared by the same manner as described above.

Figure 27:
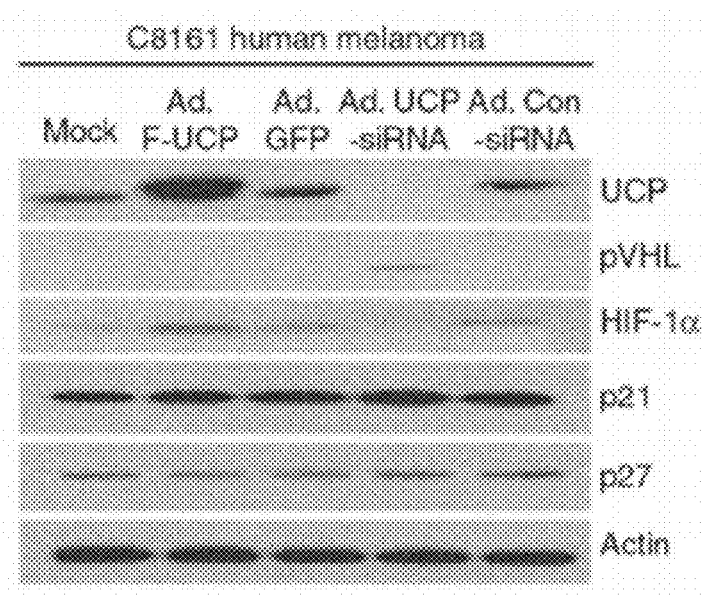
FIG. 27 is a photograph illustrating that UCP depletion by Ad.UCP-siRNA results in the increase of VHL level and the decrease of HIF-1α level in the melanoma cell line C8161.

C8161, the skin cancer cell line, was transduced respectively with Ad.F-UCP, Ad.UCP-siRNA, and Ad.GFP and Ad.Con-siRNA as control viruses by 50 MOI. 48 hours later, the cells were harvested, frozen at −70° C. and lysed in a cell lysis buffer. Western blotting was performed with the lysate using mouse anti-Flag, mouse anti-VHL, mouse anti-HIF-1α, mouse anti-p21, mouse anti-p27 antibody, and mouse anti-actin antibodies by the same manner as described earlier. As a result, the higher UCP expression, the higher HIF-1α expression was. In the meantime, the inhibition of UCP expression results in increase of VHL level and in decrease of HIF-1α, but the levels of p21 and p27 were not changed (FIG. 27).

Figure 28:
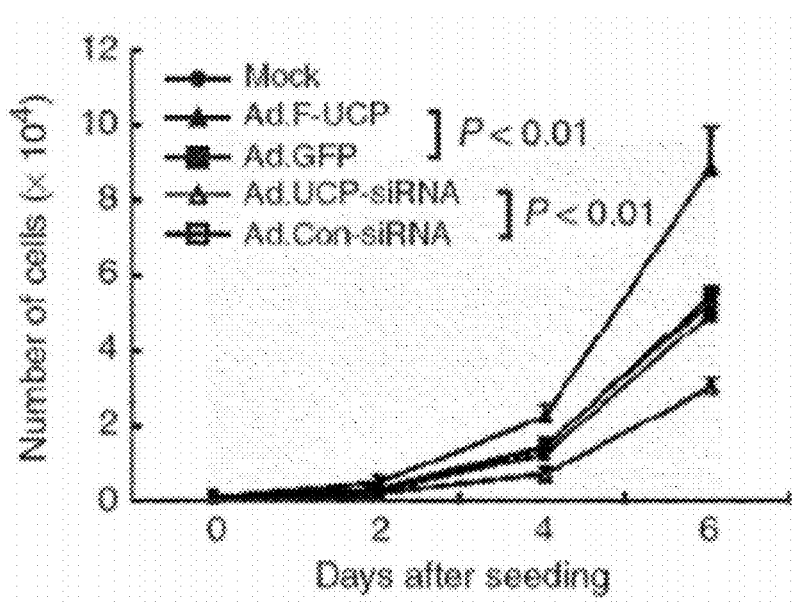
FIG. 28 is a graph illustrating that UCP depletion by Ad.UCP-siRNA results in the suppression of the human melanoma C8161 cell proliferation.

C8161, the skin cancer cell line, was transduced with Ad.F-UCP, Ad.UCP-siRNA and Ad.GFP and Ad.Con-siRNA as control viruses by 50 MOI. The control group was treated with PBS. 16 hours later, the cells were distributed into a 6-well plate at the density of 100 cells per well. The cell number was counted with a hemacytometer at two day intervals. UCP over-expression increased cell growth rate approximately up to two-fold. However, UCP depletion by Ad.UCP-siRNA resulted in the decrease of cell growth rate approximately up to two-fold (FIG. 28).

Figure 29:
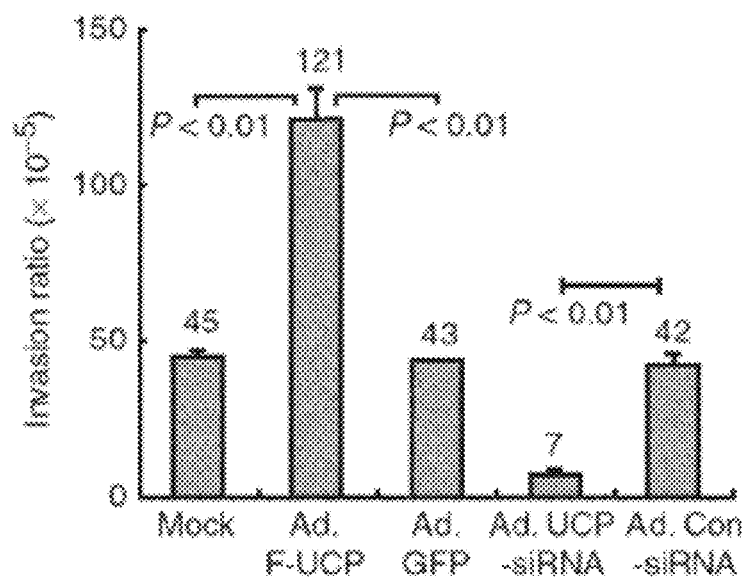
FIG. 29 is a graph illustrating that UCP depletion by Ad.UCP-siRNA results in the inhibition of the human melanoma C8161 cell invasion.

Invasion assay was performed to investigate if UCP expression affects invasiveness of C8161 cell. The C8161 cells were treated as the above and 16 hours later, $10^4$ cells were distributed in a trans-well (Costar, USA) coated with matrigel (BD, USA), followed by culture for 24 hours in HDMEM (10% FBS, 100 µg penicillin/streptomycin). Cells that had been passed through the trans-well were stained with haematoxylin-eosin and counted. As a result, UCP over-expression increased cell invasion rate up to 3 fold, compared with the control group. UCP depletion resulted in the decrease of cell invasion approximately 73% (FIG. 29).

The above results indicate that UCP plays an important role in tumor cell growth and invasion, and thus UCP inhibition will result in the inhibition of tumor cell growth and invasion.

<6-4> The Effect of UCP-siRNA on Ck-K1, the Cholangiocarcinoma Cell Line

The present inventors investigated whether the effect of UCP on the skin cancer cell line C8161 was consistent with the effect on the cholangiocarcinoma cell line (Ck-K1).

Figure 30:
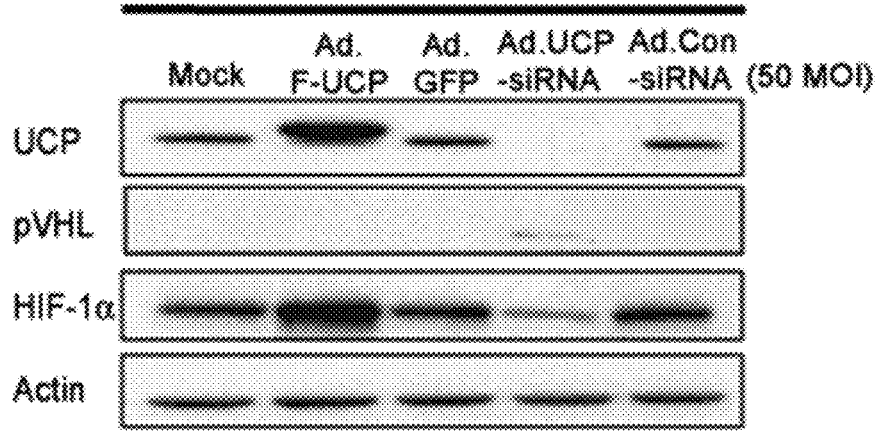
FIG. 30 is a photograph of Western blotting illustrating that UCP depletion by Ad.UCP-siRNA results in the increase of VHL level and the decrease of HIF-1α level in the cholangiocarcinoma cell line Ck-K1.

Ck-K1 cells were infected with Ad.F-UCP, Ad.UCP-siRNA and Ad.GFP and Ad.Control-siRNA, as control viruses, by 50 MOI each. 48 hours later, the cells were harvested, frozen at −70° C. and lysed in a cell lysis buffer. Western blotting was performed with the lysate using mouse anti-Flag, mouse anti-VHL, mouse anti-HIF-1α, and mouse anti-actin antibodies by the same manner as described above. The result was consistent with that from the skin cancer cell line, that is, HIF-1α expression was increased with the increase of UCP expression in Ck-K1 cells, and UCP depletion results in the increase of VHL level (FIG. 30).

Example 7

Specificity of Ad.UCP-siRNA

Following experiments were performed to confirm that UCP-siRNA specifically depleted endogenous UCP alone.

<7-1> Preparation of Secondary UCP siRNA Oligomer and Control siRNA Oligomer

The present inventors prepared mRNA sequence corresponding to 272-290 region of UCP (SEQ. ID. NO: 8, sense 5'AUGGCGAGAUCUGCGUCAATT3'; SEQ. ID. NO: 9, antisense 5'UUGACGCAGAUCUCGCCAUTT3' (Samchully Pharm. Co. Ltd., Korea)), which were dissolved in RNase free distilled water at the concentration of 20 µM and then loaded in an annealing buffer (20 mM KCl, 6 mM HEPES-KOH, pH 7.5, 0.2 mM $MgCl_2$) at the final concentration of 8 µM. After denaturation at 90° C. for 2 minutes, the temperature was lowered slowly, leading to annealing. The product was stored at −70° C. for further use. Control siRNA was prepared using sequences represented by SEQ. ID. NO: 10 (sense 5'AAGGAGACGAGCAAGAGAATT3') and NO: 11 (antisense 5'UUCUCUUGCUCGUCUCCUUTT3' (Samchully Pharm. Co. Ltd., Korea)) (Chen Z et al. Nature 436; 725-730, 2005) by the same manner as described hereinbefore.

Figure 31A:
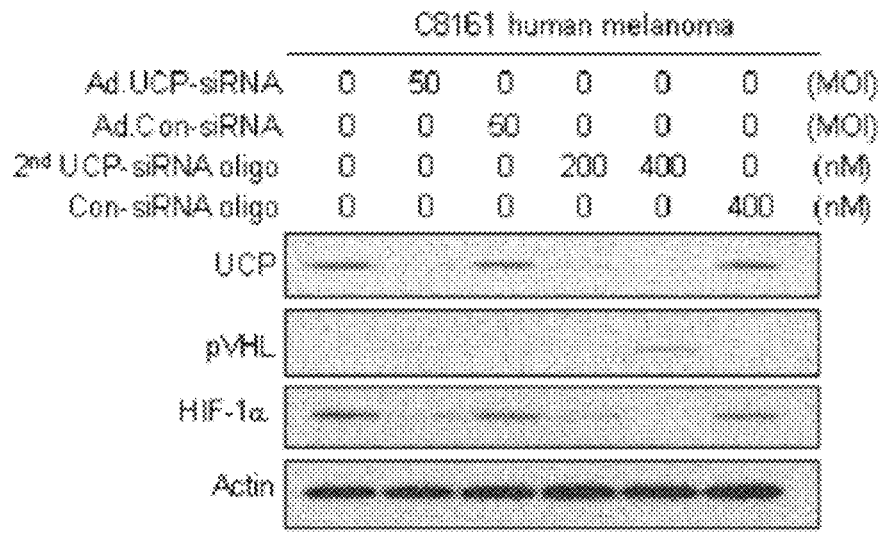
FIG. 31a is a photograph of Western blotting illustrating that UCP depletion can also be achieved by a secondary UCP-siRNA that targets different UCP mRNA sequence from that targeted by Ad.UCP-siRNA encoded siRNA.

C8161 cells were infected with Ad.UCP-siRNA and Ad.Con-siRNA by 50 MOI for each. The cells were transfected with UCP-siRNA oligomer (200 nM and 400 nM) and control siRNA oligomer (400 nM) by Lipofectamine 2000. 48 hours later, the cells were harvested, followed by Western blotting. As a result, secondary UCP-siRNA oligomer effectively inhibited UCP expression (FIG. 31a).

<7-2> F-UCP Silent Mutant (SM) Test

A mutant F-UCP (SM) (SEQ. ID. NO: 12) with the change of nucleotide sequence without changing amino acids of UCP-siRNA target sequence (AAG AAG CTG GCG GCC AAG AAA (SEQ. ID. NO: 19)->AAA AAA TTA GCA GCT AAA AAG (SEQ. ID. NO. 20)) was prepared by cloning a mutant fragment obtained from PCR using wild type F-UCP as a template into NotI/BamHI site of pCMV taq1 vector (Stratagene, USA).

Figure 31B:
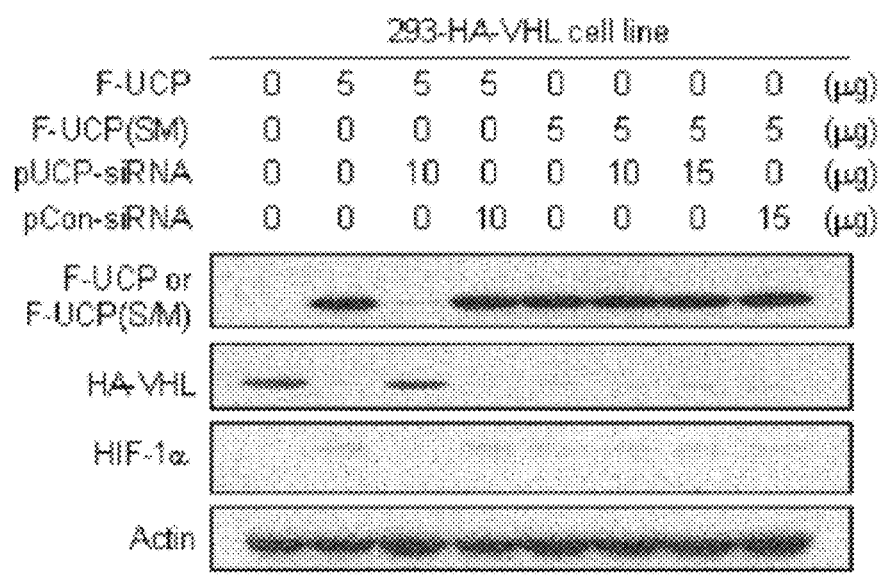
FIG. 31b is a photograph of Western blotting illustrating the rescue of the targeted transcript by using a codon-optimized non-degradable form of UCP mutant, UCP (SM).

293-HA-VHL cells were co-transfected with F-UCP or F-UCP (SM) expression vectors and pSuper UCP-siRNA or pSuper Con-siRNA. 48 hours later, the cells were harvested, followed by Western blotting to investigate functionality of UCP-siRNA. As a result, UCP-siRNA inhibited wild type F-UCP expression but did not affect F-UCP (SM) expression (FIG. 31b). UCP depletion resulted in the increase of HA-VHL level and in the decrease of HIF-1α only in wild type F-UCP. The above results indicate that UCP-siRNA prepared herein specifically recognizes and degrades a specific target of nucleic acid of UCP, which seems not to be resulted from innate immune system.

Example 8

The Effect of UCP on Tumor Growth and Metastasis in a Mouse Cancer Model

Figure 32:
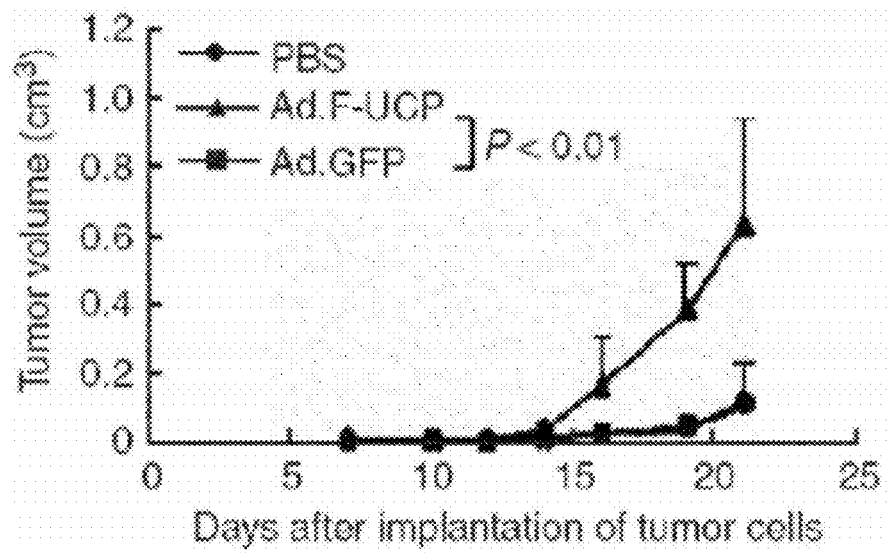
FIG. 32 is a graph illustrating that Ad.F-UCP is introduced into the human melanoma C8161 cell line and this cancer cell line is subcutaneously inoculated into a nude mouse, as a result UCP promotes tumor cell proliferation in vivo.
Figure 33:
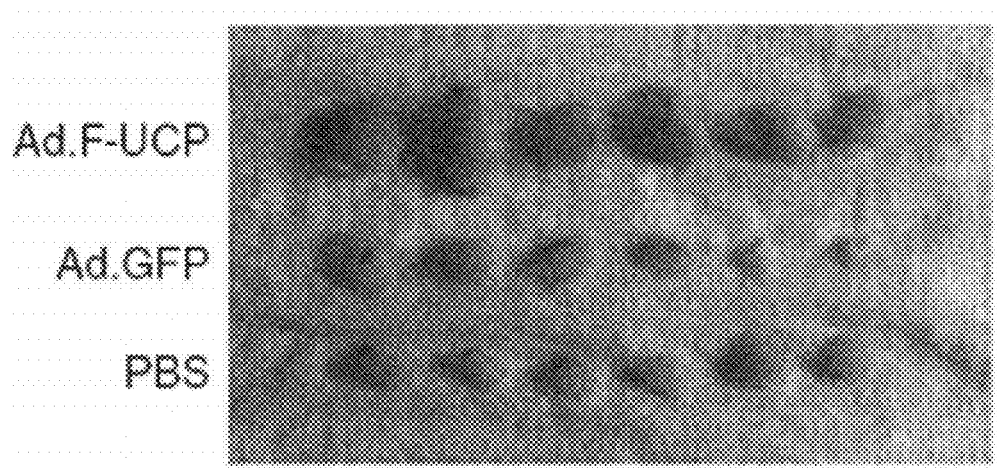
FIG. 33 is a photograph illustrating tumor nodules excised from mice 21 days after the cell implantation.

<8-1> The Effect of UCP on Tumor Growth in a Mouse Model $5 \times 10^5$ C8161 cells were infected with Ad.F-UCP and Ad.GFP by 100 MOI respectively or treated with PBS. The cells were subcutaneously injected into different areas of female nude mice at 6 weeks (3 mice per each group, 2 sites injection/mouse). The growth of C8161 cancer cells implanted in the mouse was measured for 21 days from injection. The tumor size was calculated by the formula 'width $(mm^2) \times$ length $(mm)/2 =$ tumor volume $(mm^3)$'. As a result, the tumor size was increased approximately at least 4 fold, compared with a control group (FIG. 32 and FIG. 33).

Figure 34:
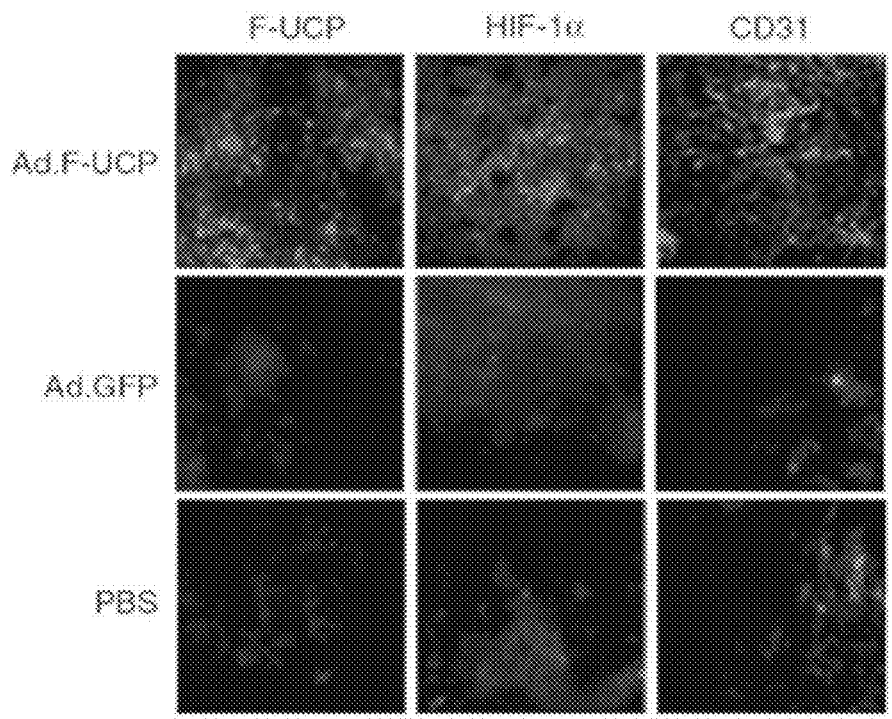
FIG. 34 is immunofluorescent photographs of sections of the excised tumor illustrating the expressions of F-UCP, HIF-1α and the vascular cell marker CD31.

To confirm the increase of HIF-1α by UCP, tumors were excised and frozen blocks were cut into sections. Immunohistochemical staining was performed using mouse anti-Flag antibody, mouse anti-HIF-1α antibody, and mouse anti-CD31 antibody (Pharmingen, USA) by the same manner as described above. As a result, HIF-1α and CD31 expressions were increased in the tumor nodule infected with Ad.F-UCP, compared with a control (FIG. 34). The present inventors also investigated whether the adenoviral vector genome could survive for 21 days in the tumor. 100 MOI of Ad.F-UCP and Ad.GFP treating or non-treating C8161 cells ($5 \times 10^5$/site) were subcutaneously injected into a nude mouse and tumors were excised 21 days later. Genomic DNA was extracted from the tumor by Phenol/Chloroform method and recovered with 100% ethanol. Southern blotting was performed using a 2 kb fragment obtained by treating adenovirus type 5 genomic DNA with HindIII as a probe. As a result, the adenovirus nucleic acid was constantly detected for 21 days in the tumor (FIG. 40*a*). Total RNA was extracted from the tumor by Rneasy mini kit (Qiagen, GERMANY) protocol. RT-PCR was performed to confirm Flag-UCP with a primer set (SEQ. ID. NO: 13, 5'-ATGAACTCCAACGTGGAGAA-3' and SEQ. ID. NO: 14, 5'-CTACAGCCGCCGCAGCGC-3') and to confirm GFP with another primer set (SEQ. ID. NO: 16, 5'-AAGGAGAAAACTTTTCACT-3' and SEQ. ID. NO: 15, 5'-TAATGGTCTGCTAGTTGAAC-3'). As a result, F-UCP and GFP mRNAs were detected in the tumor cells (FIG. 40*b*).

<8-2> Anticancer Effect of Ad.UCP-siRNA Virus in a Mouse Cancer Model

Figure 35:
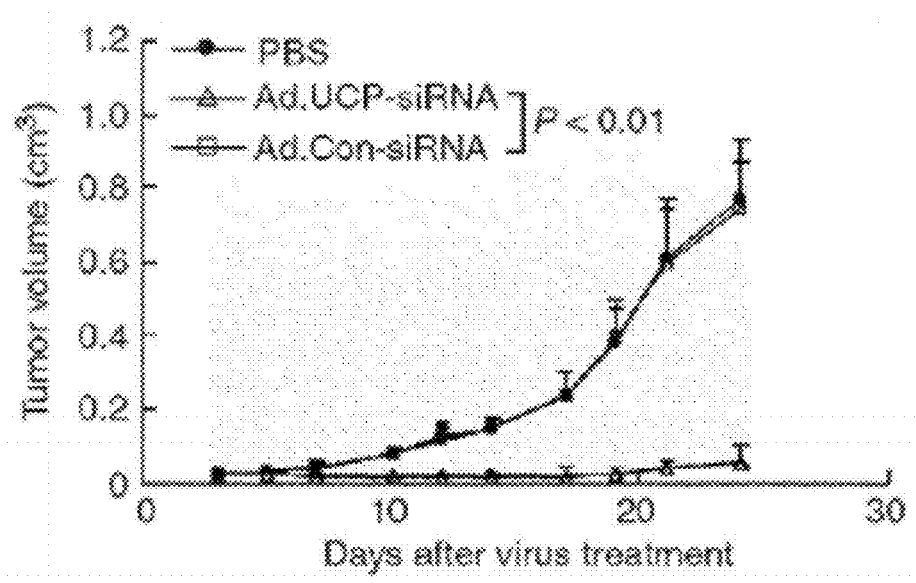
FIG. 35 is a graph illustrating that nude mice are subcutaneously inoculated with human melanoma C8161 cells to form a tumor nodule and then injected with Ad.UCP-siRNA, resulting in the significant inhibition of tumor cell growth.

To verify the anticancer effect of UCP-siRNA, $5 \times 10^5$ C8161 cells were subcutaneously injected into a nude mouse. Two weeks later when a tumor reached 3 mm in mean diameter, 100 μl of PBS containing or not containing $10^9$ pfu of purified Ad.UCP-siRNA or Ad.Con-siRNA was injected directly to the tumor nodule and then the tumor size was measured for 17 days. As a result, Ad.UCP-siRNA treatment resulted in significant inhibition of C8161 tumor growth (FIG. 35).

Figure 36:
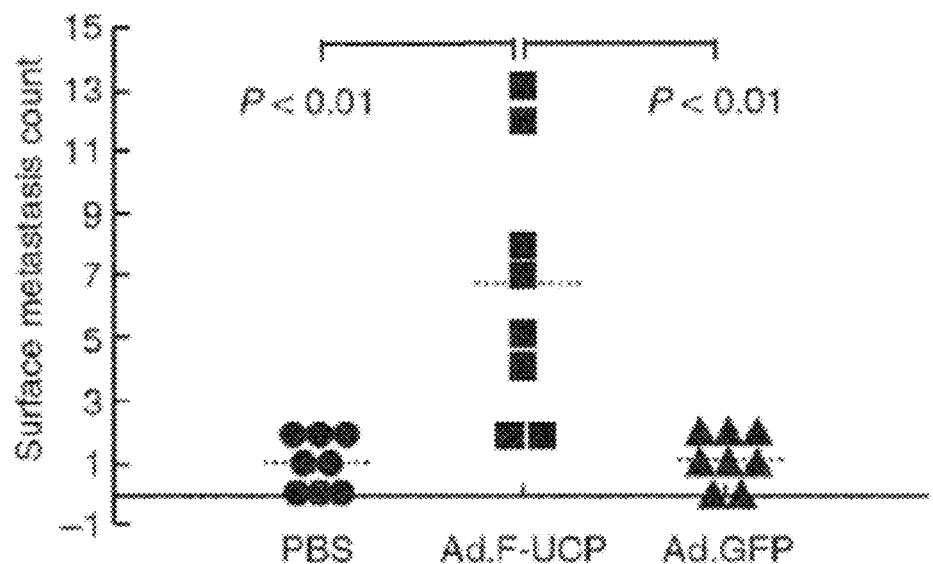
FIG. 36 is a graph illustrating that nude mice are subcutaneously inoculated with human melanoma C8161 cells, followed by direct injection of Ad.F-UCP into the tumor tissues to examine UCP effect on metastasis. As a result, UCP over-expression induces spontaneous metastasis to the lung.
Figure 37:
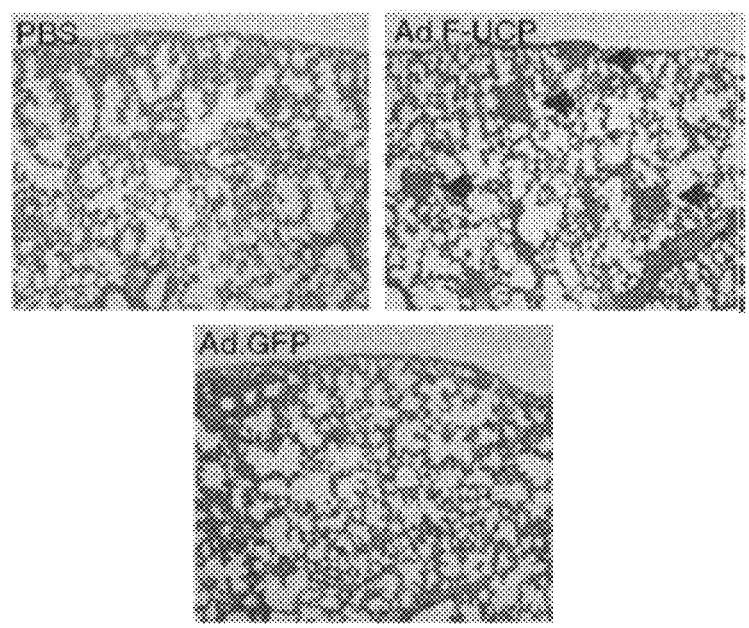
FIG. 37 is a set of photographs of H&E staining illustrating the metastasis of melanoma cells into the mouse lung, as indicated in FIG. 36.

<8-3> The Effect of UCP on Metastasis in a Mouse Cancer Model $10^6$ C8161 cancer cells in 100 μl PBS were subcutaneously injected into the center of abdomen of a nude mouse (female, 5W, nude Balb/c, N=8). One week later when the tumor reached 3 mm in mean diameter, each virus (Ad.F-UCP, Ad.GFP) was dissolved in 50 ul PBS at the concentration of $10^9$ pfu, which was injected into the center of the tumor nodule. 9 weeks later, the lung was excised, fixed in Bouin's solution and stained with H&E, followed by observation on the tumor metastasis. As a result, metastasis was significantly promoted in the group over-expressing UCP (FIG. 36 and FIG. 37).

Figure 38:
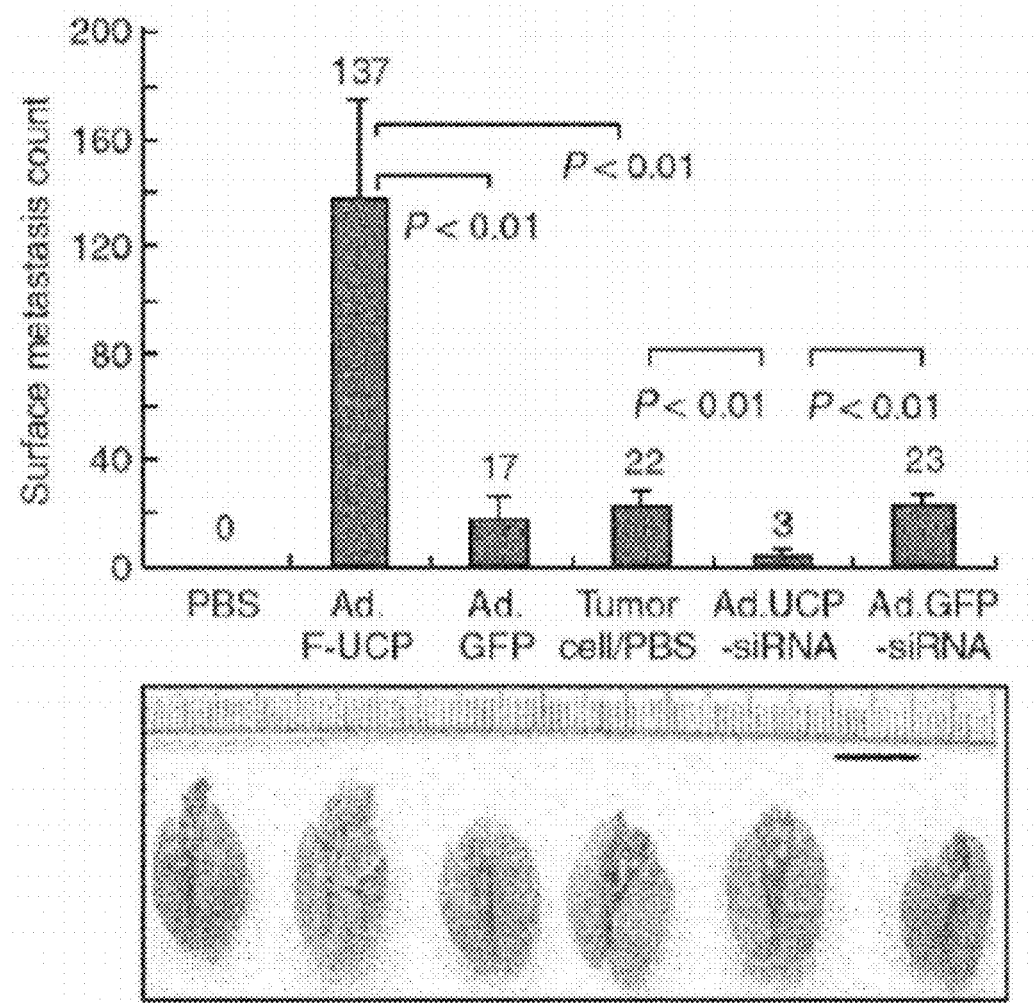
FIG. 38 is a set of a graph and a photograph of excised lung organs from mice 4 weeks after the tumor cell injection, illustrating that human melanoma cells transduced with Ad.F-UCP or Ad.UCP-siRNA are injected into a nude mouse through the tail vein and UCP effect on metastasis is examined. UCP over-expression promoted metastasis to the lung and Ad.UCP-siRNA inhibited the metastasis to the lung.

$5 \times 10^5$ human melanoma C8161 cells were infected with 100 MOI of Ad.F-UCP, Ad.GFP, Ad.UCP-siRNA, or Ad.GFP-siRNA (SEQ. ID. NO: 17). PBS with or without C8161 cells as controls and the infected C8161 cells were intravenously injected through the tail vein of a female nude mouse (6 weeks old). Four weeks later, the lung of the mouse was excised, washed with water and fixed in Bouin's solution (SIGMA). The morphology of the sliced lung tissue (FIG. 39) and the metastasized tumor nodule (>2 mm in diameter) on the surface of the lung were observed under microscope, and the mean number of the tumor nodule is shown in FIG. 38.

As a result, the numbers of metastasized tumor nodule to the lung were 17 for Ad.GFP, 22 for C8161 cells in PBS, and 23 for Ad.GFP-siRNA, while metastatic tumor was not detected when PBS alone was injected, suggesting that metastasis to the lung was induced by injection of the cancer cells.

Metastasis to the lung was increased approximately 6-8 fold when UCP was over-expressed by Ad.F-UCP, whereas metastasis to the lung was inhibited approximately 6-7 fold when UCP expression was inhibited by Ad.UCP-siRNA. The above result indicates that UCP acts as a positive factor for cancer metastasis and thus inhibition of UCP expression or UCP activity results in the suppression of cancer metastasis.

The above results indicate that UCP increases tumor growth and metastasis in mouse cancer models and thus inhibition of UCP function results in the inhibition of tumor cell growth and metastasis. Therefore, UCP is a new molecular target for the treatment of cancer.

Example 9

Figure 41:
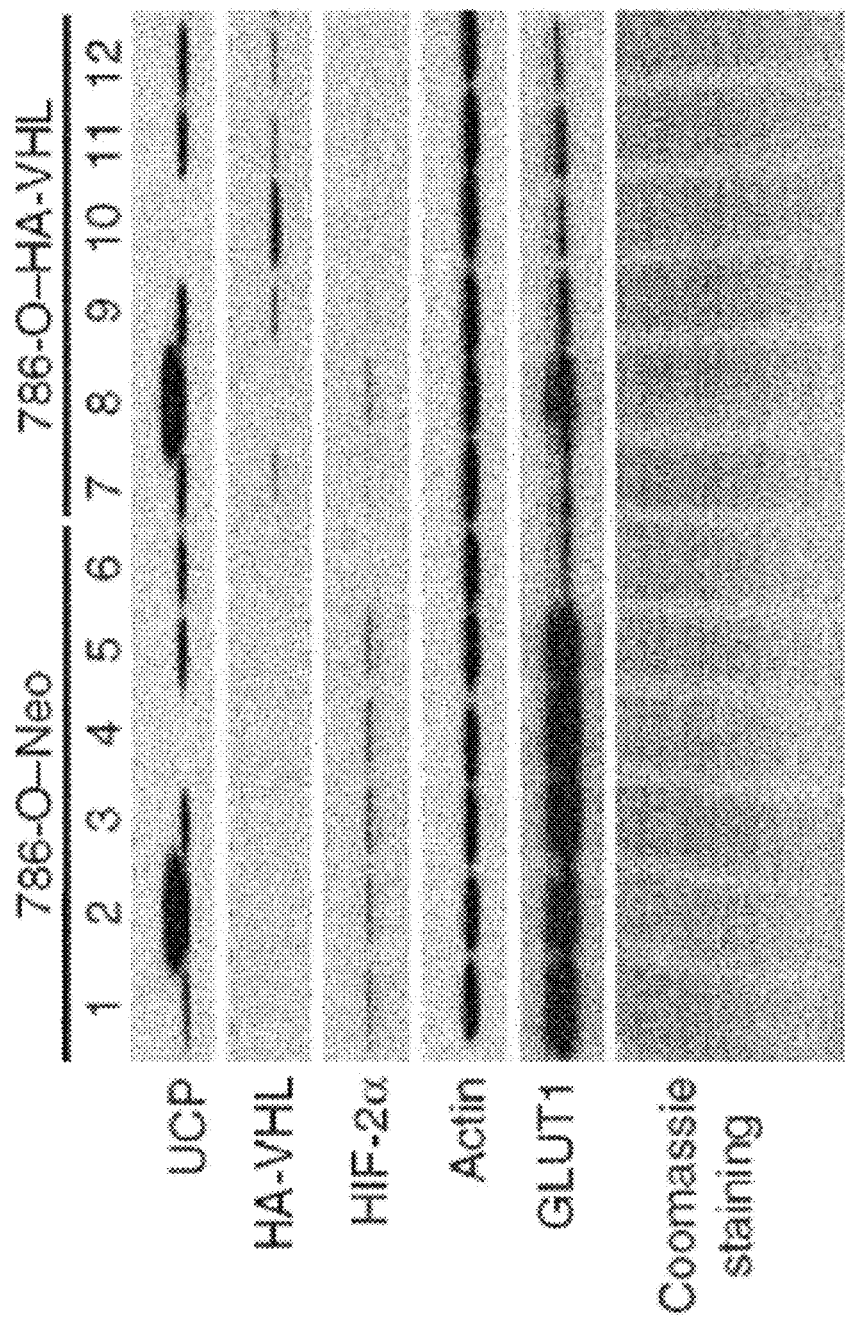
FIG. 41 is a photograph of Western blotting illustrating that UCP regulates HIF-2α through VHL.

UCP Specificity to VHL-HIF Pathway 786-0, a kidney cancer cell line not expressing VHL, exhibits HIF-2α over-expression (Nat 399, 271-299, 1999) and UCP expression therein is high (FIG. 41). This cell line was modified to constitutively express HA-VHL, which is named 786-0-HA-VHL cell line (by transfection with the expression vector pcDNA-HA-VHL constructed by inserting HA-VHL into the commercial pcDNA vector from Invitrogen, followed by selection under culture medium containing neomycin), and then UCP effect therein was investigated. For the experiment, Ad.HIF2α-siRNA (SEQ. ID. NO: 18) was generated containing 5' GGAGACGGAGGTGTTCTAT 3', nucleotides 1-19 of SEQ. ID. NO. 18, the sequence of 86-104 region of HIF-2α mRNA, by the same manner as described above.

<9-1> UCP Regulates the VHL-HIF Pathway in Culture Cell 786-0-HA-VHL and 786-0 cell lines were infected with or without Ad.F-UCP, Ad.GFP, Ad.UCP-siRNA, Ad.Con-siRNA, or Ad.HIF-2α-siRNA by 50 MOI, followed by Western blotting to investigate expression patterns of UCP, VHL, HIF-2α, and GLUT1 (Expression of this gene is induced by HIF-1α or HIF-2α). GLUT1 was detected by GLUT1 antibody (Santa Cruz, USA). As a result, neither HIF-2α nor GLUT1 expression level was changed in the 786-0 cell line regardless of UCP over-expression or depletion. On the other hand, HA-VHL level was reduced by UCP over-expression in 786-o-HA-VHL cells, and thereby HIF-2α and GLUT1 expressions were increased and UCP depletion increased VHL level and consequently decreased HIF-2α and GLUT1 levels (FIG. 41).

Figure 42:
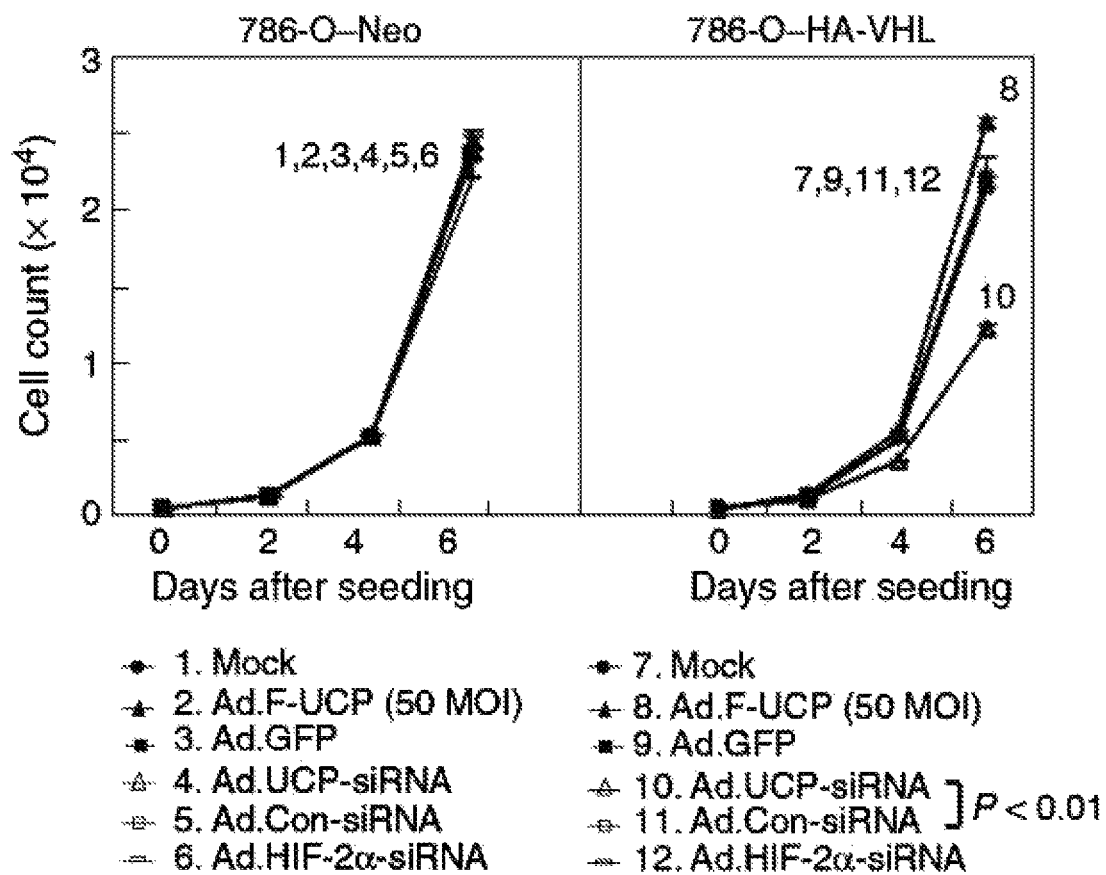
FIG. 42 is a set of graphs illustrating that UCP regulates cell growth through VHL.

The tumor cell growth rates between the two cell lines treated with different viruses as indicated above were compared. As a result, in the 786-0 cell line, the tumor cell growth rates were not much different among the groups treated with different viruses, whereas the cell growth rate of Ad.UCP-siRNA treated 786-0-HA-VHL cell line was significantly decreased (FIG. 42).

Figure 43:
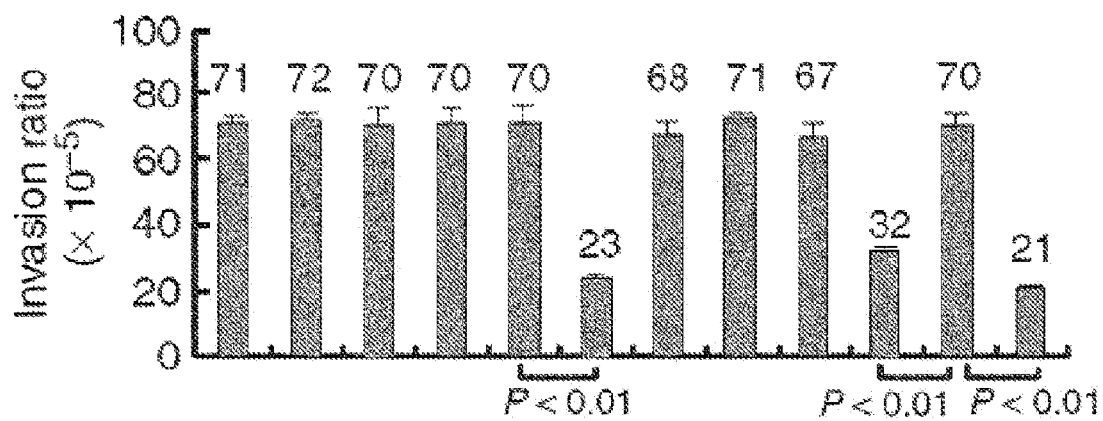
FIG. 43 is a graph illustrating that UCP regulates cell invasion through VHL-HIF pathway.

The tumor cell invasiveness between the two cell lines treated with different viruses as indicated above were compared. As a result, invasiveness was reduced only in the 786-0-cells treated with Ad.HIF-2α-siRNA among those treated cells. Invasiveness was reduced in 786-0-HA-VHL cells treated with Ad.UCP-siRNA or Ad.HIF-2α-siRNA among those treated cells (FIG. 43).

These results suggest that i) VHL regulates cell growth in culture independent of HIF-2α level; ii) HIF-2α regulates cell invasiveness, but not cell growth in culture; and iii) UCP regulates cell growth through VHL and cell invasion through the VHL-HIF pathway.

Figure 44:
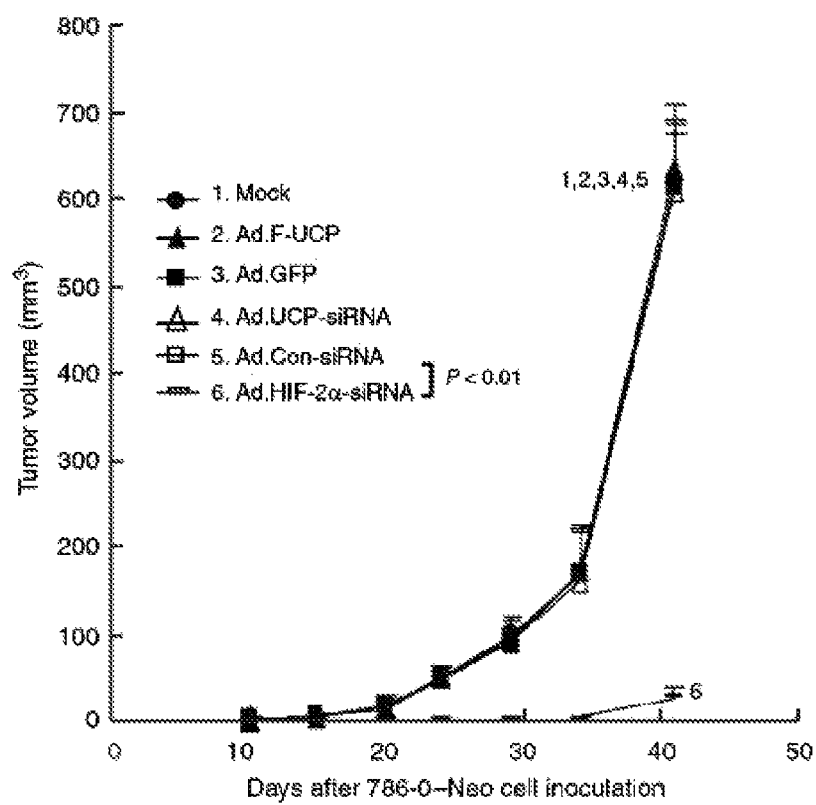
FIG. 44 is a graph illustrating that UCP regulates tumor growth through VHL in mouse.
Figure 45:
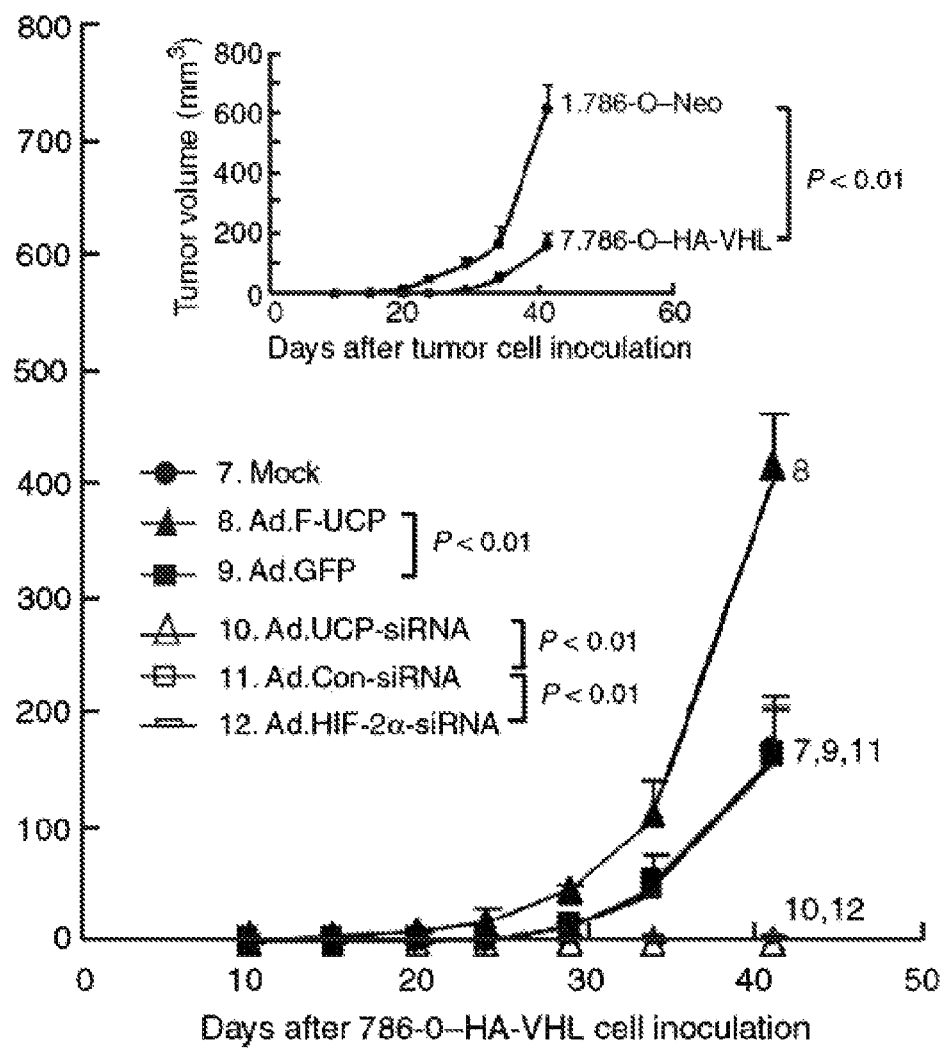
FIG. 45 is also a set of graphs illustrating that UCP regulates tumor growth through VHL in mouse.

<9-2> UCP Regulates the VHL-HIF Pathway In Vivo 786-0-HA-VHL and 786-0-cell lines were infected with or without Ad.F-UCP, Ad.GFP, Ad.UCP-siRNA, Ad.Con-siRNA, Ad.HIF-2α-siRNA at an MOI of 100 for 2 hours. The cells were harvested and 16 hours later, they were suspended in PBS ($10^7$ cells/100 µl), which was subcutaneously injected under the right thigh of a nude mouse (female, 5W, Balb/c, N=5). Tumor growth over the times was observed. Ad.HIF-2α-siRNA exhibited tumor suppression effect in both 786-0 and 786-0-HA-VHL cells (FIG. 44 and FIG. 45). Ad.UCP-siRNA inhibited growth of 786-0-HA-VHL cell, but not 786-0 cell. UCP over-expression by Ad.F-UCP promoted growth of 786-0-HA-VHL, but not 786-0 cell (FIG. 44 and FIG. 45). These results indicate that the effect of UCP on tumor growth in mice is mediated by the VHL-HIF pathway.

Example 10

Construction of a Cell Line for High Throughput Screening (HTS) of a UCP Inhibitor UCP was confirmed hereinbefore to promote tumor cell growth and metastasis by regulating the VHL-HIF pathway and thus inhibition of UCP expression by UCP-siRNA increased VHL level, resulted in tumor cell growth inhibition (FIGS. 41 and 42). Therefore, the present inventors investigated the possibility of using 786-0 and 786-0-HA-VHL cell lines for the cell-based HTS assay to screen a UCP specific inhibitor.

Figure 46A:
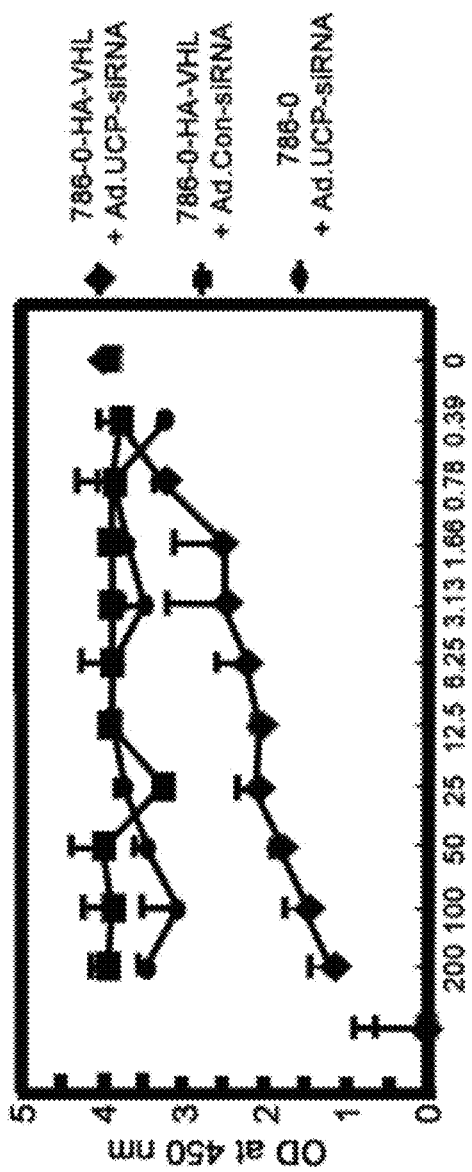
FIG. 46a is a graph illustrating that cell growth inhibition by UCP depletion was observed in 786-0-HA-VHL cells.

786-0 and 786-0-HA-VHL cells were inoculated in a 96-well plate ($10^3$ cells/well). Ad.UCP-siRNA and Ad.Con-siRNA as a control were serially diluted from 200 MOI to 0.39 MOI, two fold each time, which infected the above cells. 48 hours after the infection, cell growth was measured with WST-1 (Roche, Germany). 786-0 cells were treated with Ad.UCP-siRNA as a control to find out whether a compound specifically inhibits the function of UCP. As a result, cell growth inhibition by UCP depletion was observed in HA-VHL expressing 786-0 cells, but no such effect was detected in 786-0-cells or Ad.Con-siRNA treated cells (FIG. 46a).

Figure 46C:
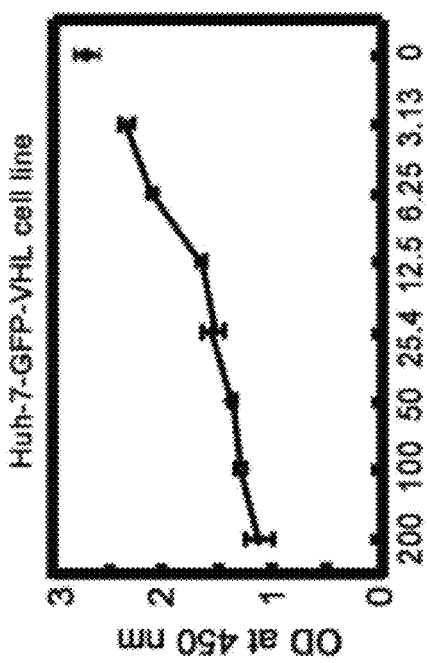
FIG. 46c is a graph illustrating that cell growth inhibition by UCP depletion was observed in Huh-7-GFP-VHL cells.
Figure 46B:
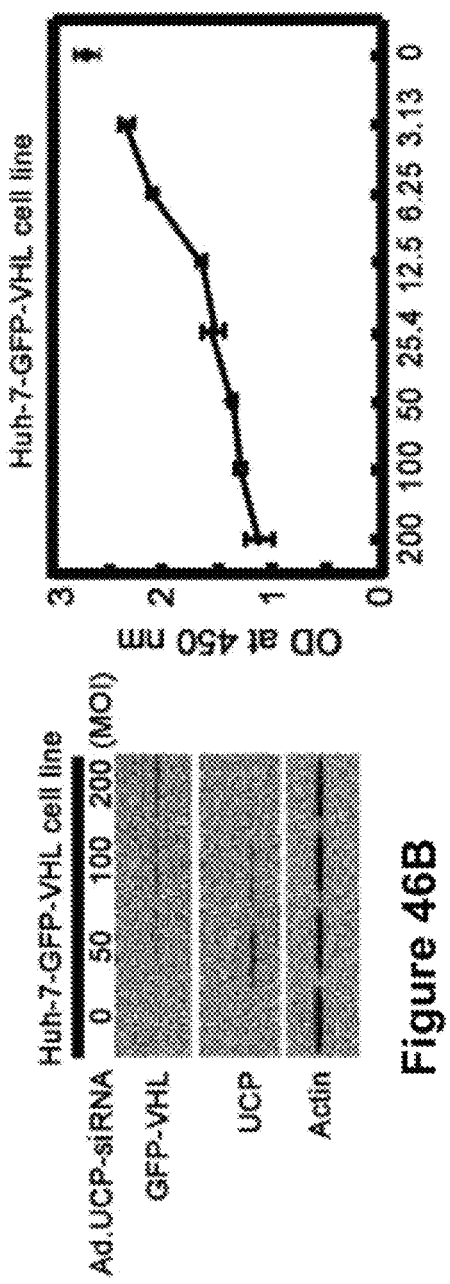
FIG. 46b is a photograph of Western blotting illustrating the increase of GFP-VHL level by UCP depletion.

Huh-7, a liver cancer cell line, was transfected with pCNA-GFP-VHL expression vector constructed by inserting GFP-VHL fusion gene into pcDNA vector provided by Invitrogen. A Huh-7-GFP-VHL cell line, a Huh-7 cell line permanently expressing GFP-VHL, was generated for another cell based assay. From the Western blotting, it was proved that UCP depletion in this cell line resulted in the increase of GFP-VHL (FIG. 46b).

Huh-7-GFL-VHL cells were inoculated in a 96-well plate ($10^3$ cells/well). Ad.UCP-siRNA was serially diluted from 200 MOI to 3.13 MOI, two fold each time, which infected the above cells. 48 hours after the infection, cell growth was measured with WST-1 (Roche, Germany). As a result, UCP depletion resulted in cell growth inhibition (FIG. 46c).

Therefore, 786-0, 786-0-HA-VHL and Huh-7-GFP-VHL cell lines can be effectively used for the screening of a UCP enzyme activity inhibitor and a UCP-VHL interaction inhibitor.

Example 11

The Effect of UCP on the Proliferation of Vascular Cells

As explained hereinbefore, UCP over-expression resulted in HIF-1α stabilization and thereby increased VEGF expression. VEGF is an angiogenic factor. To examine the possibility of using UCP gene for the treatment of ischemic diseases, the level of VEGF in UCP over-expressed cell culture media was measured. In addition, whether the UCP over-expressed cell culture media could promote the proliferation of HUVEC (human umbilical vascular endothelial cell, Cambrex, USA) was also investigated.

Figure 47A:
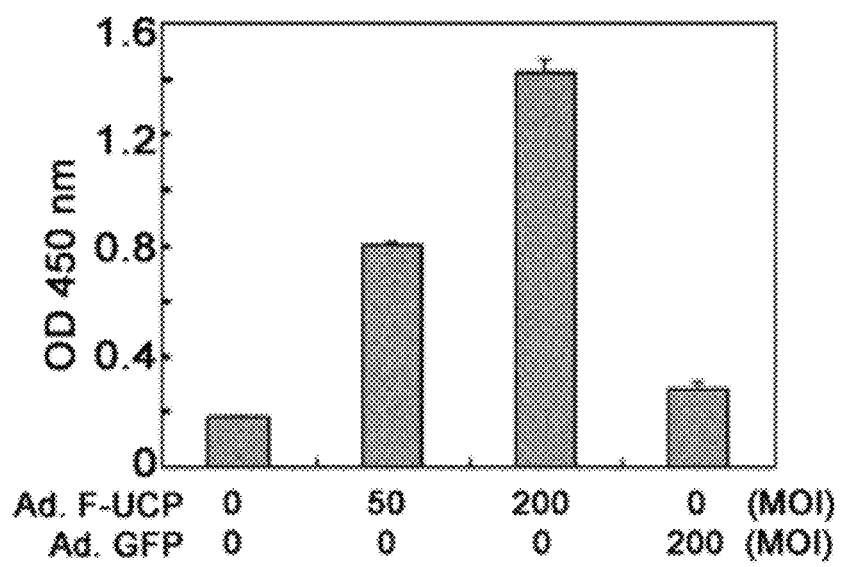
FIG. 47a is a graph illustrating that the increase of UCP expression results in the increase of VEGF level in cell culture media.
Figure 47B:
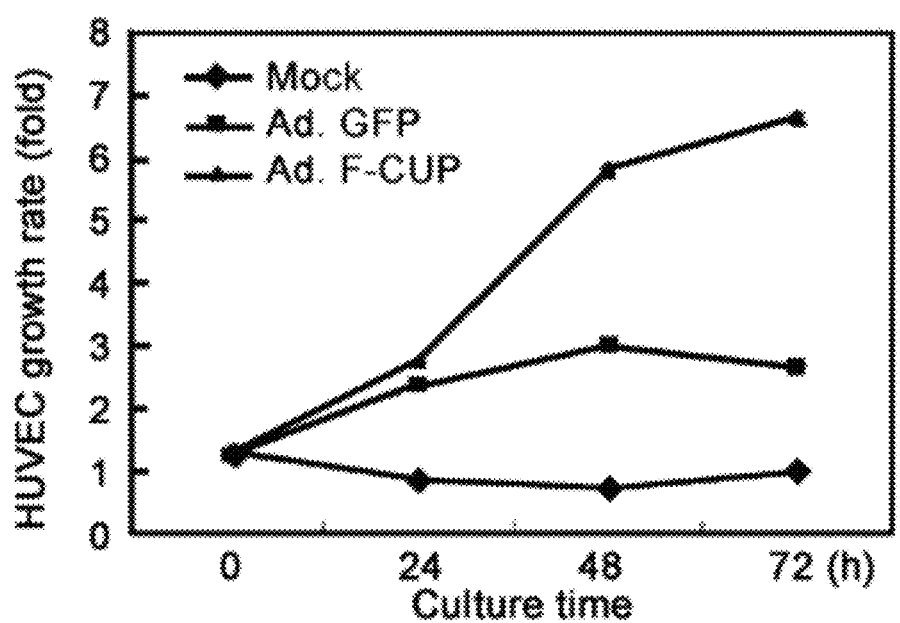
FIG. 47b is a graph illustrating that the culture media from the UCP over-expressing cell prepared in the above FIG. 47a promoted HUVEC proliferation.

Particularly, HeLa cells were infected or not infected with Ad.F-UCP (50, 200 MOI) and Ad.GFP (200 MOI) respectively. Culture supernatants (serum free media, Opti-MEM, Invitrogen) were obtained 48 hours later. The levels of VEGF in the culture supernatants were measured by using an ELISA kit (TiterZyme EIA kit, Assay designs, USA). As a result, the level of VEGF in the culture supernatant of UCP over-expressing cells was three-fold higher than in control group (FIG. 47a). The present inventors further investigated whether the biological activity of VEGF to promote angiogenesis was detected in the culture supernatant. HeLa cells were infected or not infected with Ad.F-UCP and Ad.GFP respectively by 200 MOI. 48 hours after the infection, culture supernatants (serum free media, Opti-MEM, Invitrogen) were obtained, which were further treated to HUVEC in a 96-well plate ($3 \times 10^3$/well). Cell growth over the times was measured by WST-1 method. As a result, HUVEC growth was approximately two fold increased in UCP expressing group, compared with a control group (FIG. 47b). Theses results indicate that angiogenesis is promoted with the increase of UCP expression, suggesting the usability of UCP for the treatment of ischemic diseases.

Example 12

UCP Increases Expression and Secretion of Angiogenesis-Related Factors in Cells

Ad-F-UCP was prepared by introducing Flag epitope tagged UCP gene (F-UCP) into gene carrier (Nature Medicine 12, 809-816, 2006; PCT No. 108014, filed on Nov. 13, 2006; Korean Patent Registration No. 877824, registered on Jan. 2, 2009; U.S. patent application Ser. No. 12/093,093, filed on May 8, 2008; Japan Patent Application No. 2008-539939, filed on May 9, 2008; EP Patent Application No. 06812582.2, filed on Jun. 4, 2008). The effect of Ad-F-UCP-mediated gene transfer of UCP on expression of angiogenesis-related factor has been demonstrated as explained below.

<12-1> UCP Induces Expression of Angiogenesis-Related Factors in Cells

VEGF (vascular endothelial growth factor) expression is regulated by the UCP-VHL-HIF1 pathway (Nat Med 12, 809-816, 2006). HIF1 transcription factor increases expression of IGF-2 and TGF-β3, along with VEGF, and thereby is involved in angiogenesis (Nat Rev Cancer 3, 721-732, 2003). It was also reported that HIF1 is involved in FGF-2 expression which induces angiogenesis (Blood 107, 2705-2712, 2006; Histopathology 46, 31-36, 2005). Since HIF1α protein is stabilized by the UCP over-expression, it has been investigated to see if expression of angiogenesis-related factor (VEGF, FGF-2, IGF-2, TGF-β3) actually increases at mRNA level as explained below. HeLa (100 multiplicity of infection, MOI), NIH3T3 (200 MOI) or MRC-5 (100 MOI) cell lines were either infected or not infected by Ad-F-UCP or Ad-LacZ, and after 48 hours, the total RNA was extracted, and RT-PCR was carried out using respective primers regarding the angiogenesis-related factors. As a result, mRNA of VEGF and FGF-2 increased 1.5 times or higher due to the increase of UCP expression, and IGF-2 and TGF-β3 showed slight increase (FIG. 48a). The above result suggests that the UCP over-expression can induce angiogenesis by increasing expression of a variety of angiogenesis-related growth factors including VEGF.

<12-2> Confirming Exocytosis of Angiogenesis-Related Factors by UCP

In order to demonstrate that the increased mRNA due to over-expression of UCP gene can actually increase the VEGF, and FGF-2 protein levels that indicate activity, HeLa (100 MOI), NIH3T3 (200 MOI), MRC-5 (100 MOI) cells were either infected or not infected with Ad-F-UCP, or Ad-LacZ viruses. After 48 hours, the cell culture media were collected, and the protein amount of VEGF, or FGF-2 of angiogenesis factors in the cell culture media were quantified using ELISA. As a result, the cell lines infected by Ad-F-UCP showed increased degree of cell release of the VEGF, and FGF-2 proteins compared to the control group (FIG. 48b), although degree of cell release of the VEGF, and FGF-2 proteins varies depending on the cell lines.

Example 13

UCP Promotes Proliferation, Tubule Formation, and Invasion of Human Umbilical Vein Endothelial Cells (HUVEC)

It was confirmed that the over-expression of UCP increases expression of angiogenesis-related factors including VEGF, and promotes exocytosis of the VEGF, and FGF-2 proteins from the UCP-over-expressed cell (FIG. 48). The activity of angiogenesis-related factors which were released out of the cells was confirmed using human umbilical vein endothelial cells (HUVEC) as explained below.

<13-1> The UCP-Over-Expressed Cell Culture Media Promote Proliferation of HUVEC

Figure 49A:
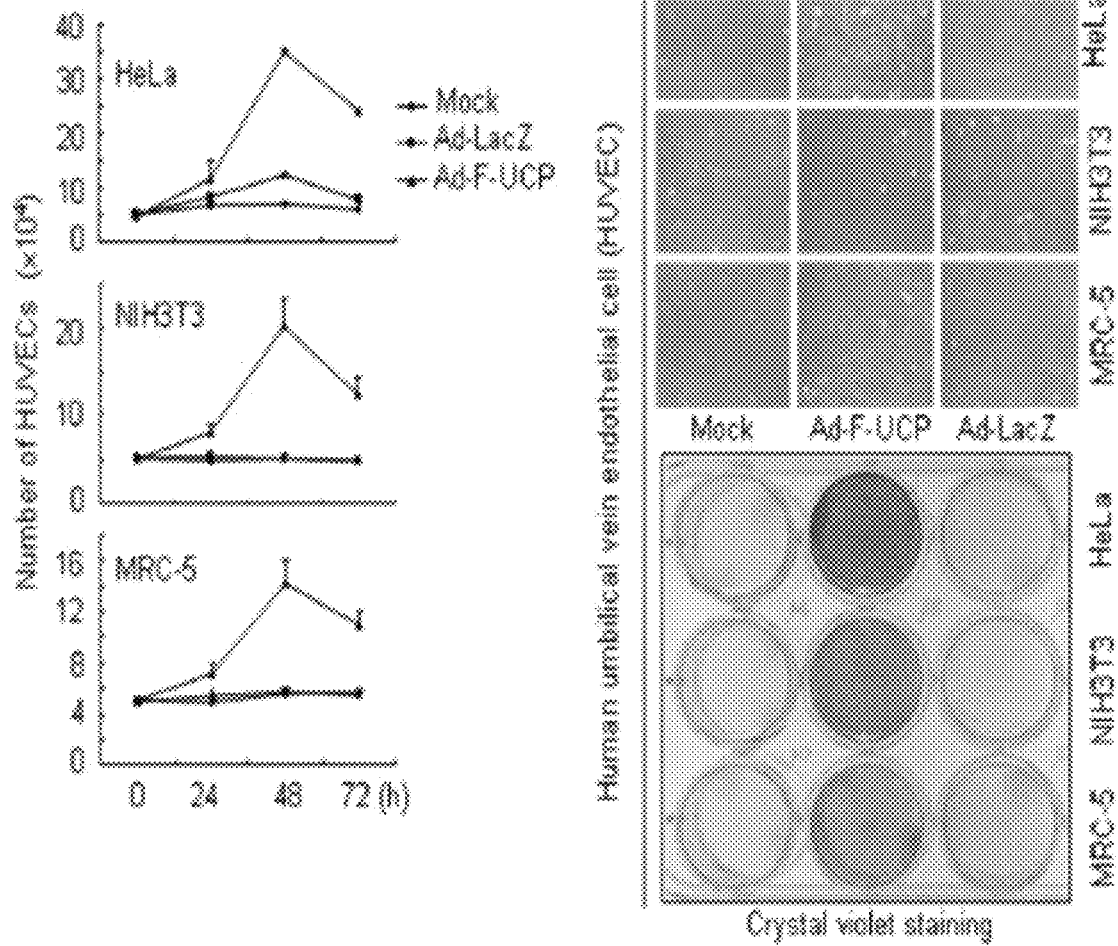
FIG. 49a is a graph showing that culture supernatants from HeLa, NIH3T3, or MRC-5 cell lines with UCP over-expression, promote proliferation of human umbilical vein endothelial cells (HUVECs) (left), a photograph showing that HUVECs proliferate rapidly when they were incubated with the supernatants from the cells with UCP over-expression (right-upper), and a photograph of HUVECs stained with crystal violet after their incubation with the culture supernatants (right-bottom).

HeLa (100 MOI), NIH3T3 (200 MOI), MRC-5 (100 MOI) cells were either infected or not infected with Ad-F-UCP, or Ad-LacZ viruses. After 48 hours, only the cell culture media were collected, treated to HUVECs and then viable HUVECs were counted with a hemocytometer every 24 hours for 72 hours. At 72 hours, the cells were photographed under a light microscope and then stained with 0.05% crystal violet (FIG. 49a, right). As a result, the culture media from the cells with Ad-F-UCP promoted proliferation of HUVECs greatly compared to control groups (Mock or Ad-LacZ) (FIG. 49a).

<13-2> UCP Promotes Tubule Formation and Invasiveness of HUVEC

Figure 49B:
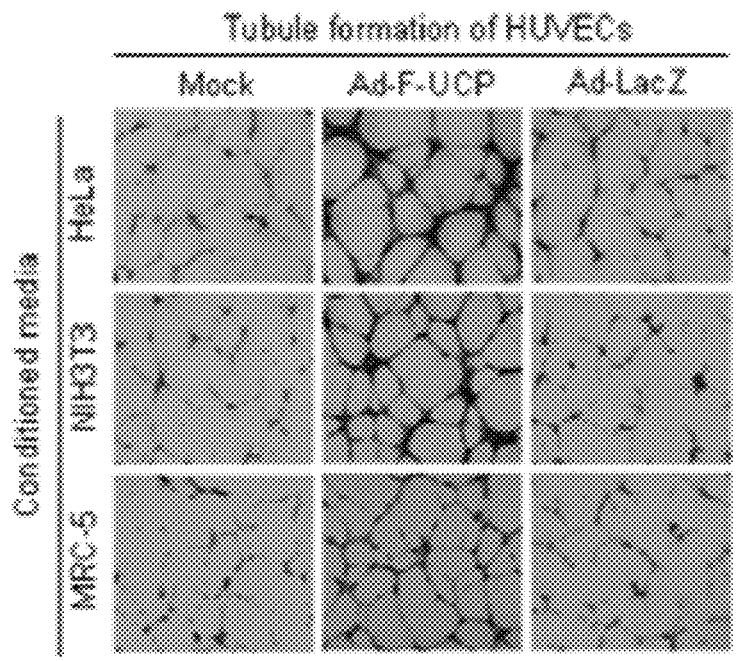
FIG. 49b is photographs demonstrating promotion of tubule formation of HUVECs by the treatment with culture media from HeLa, NIH3T3, or MRC-5 cells with UCP over-expression.
Figure 49C:
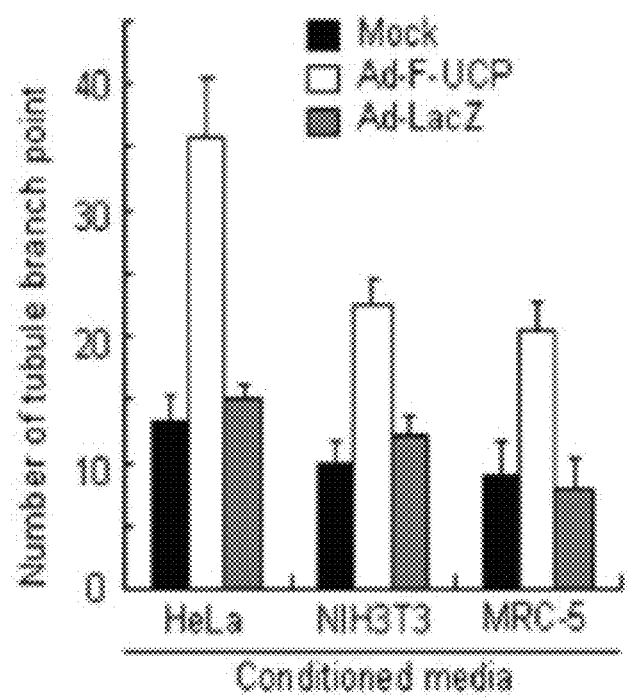
FIG. 49c is a graph quantitatively showing promotion of tubule formation of HUVECs by the treatment with culture media from HeLa, NIH3T3, or MRC-5 cells with UCP over-expression.

HeLa (100 MOI), NIH3T3 (200 MOI), or MRC-5 cells (100 MOI) were infected by Ad-F-UCP or Ad-LacZ at the indicated MOI. After 48 hours, the cell culture media were collected. HUVECs were incubated in the collected cell culture media in a Matrigel-coated 24-well plate for 24 hours. After that, HUVECs were stained with 0.05% crystal violet, photographed (FIG. 49b), and branch point of tubules was counted and quantified (FIG. 49c). As a result, it was demonstrated that the generation of tubules was noticeably increased in HUVECs incubated with the culture media from HeLa, NIH3T3, MRC-5 cells infected with Ad-F-UCP, compared to the control group (Mock or Ad-LacZ).

Figure 49D:
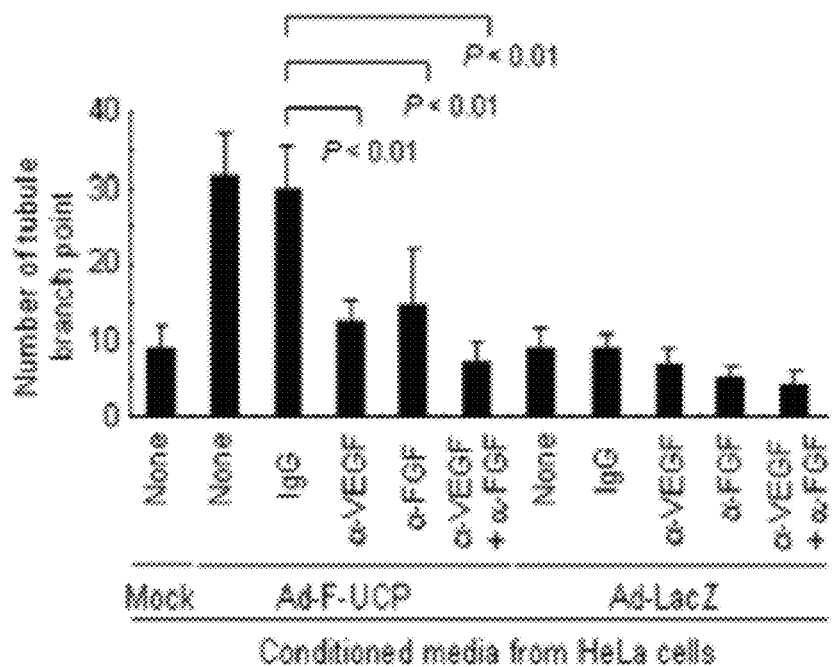
FIG. 49d is a graph demonstrating that VEGF and FGF-2 in culture media from HeLa cells with UCP over-expression are involved in tubule formation.

In order to show that the VEGF and FGF-2 existing in the UCP-expressing cell culture media actually caused the increased tubule formation of HUVEC, HeLa cells were infected with or without Ad-F-UCP or Ad-LacZ virus at an MOI of 100. We prepared the conditioned media at 48 h after transduction, preincubated them in the presence or absence of 5 μg/ml anti-VEGF and/or 2 μg/ml anti-FGF2 antibodies, or IgG for 24 h at 4° C., and then incubated HUVECs in the preincubated media for 24 h. The amount of antibody was adjusted to a total of 7 μg/ml by the addition of IgG. HUVECs were stained with 0.05% crystal violet and then photographed. We counted branch point of tubule (FIG. 49d). The branch point, which was increased by the conditioned media from cells with Ad-F-UCP, was significantly reduced by the VEGF or FGF-2 antibody, and further decreased when both antibodies were together present.

Figure 49E:
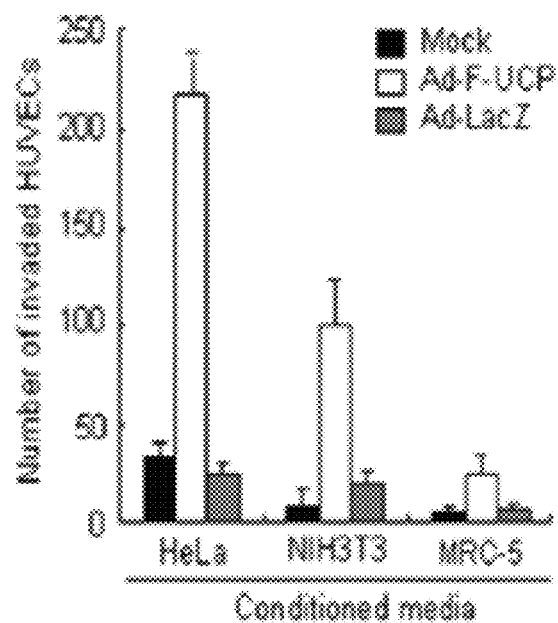
FIG. 49e illustrates that culture supernatants from HeLa, NIH3T3, or MRC-5 cells over-expressing UCP increase invasiveness of HUVEC.

After culturing HUVECs in serum-free medium for 24 h, HUVECs were plated at 5×10$^4$ cells/ml in serum-free medium in the upper chamber in Transwell chambers (8 μm, 24-well format; Corning, N.Y., USA). The insert membranes were coated with diluted Matrigel (BD Biosciences, San Jose, USA). The culture media from HeLa, NIH3T3, MRC-5 cells infected with or without Ad-F-UCP or Ad-LacZ were added to the lower chamber. HUVECs were then cultured for 24 h. After culturing, the insert membranes were cut and performed H&E staining and the permeating cells were counted under an inverted light microscope. It was demonstrated that the invasion ability of HUVEC noticeably increased with the culture media of HeLa, NIH3T3, MRC-5 cells infected with Ad-F-UCP (FIG. 49E).

Example 14

UCP Induces Neo-Vascularization in Mouse

It was demonstrated that over-expression of UCP in cultured cells stimulates expression and exocytosis of angiogenesis-related factors, and the culture media from UCP-over-expressing cells can promote angiogenesis by stimulating proliferation, tubule formation, and invasion of HUVECs (FIG. 49). Effect of UCP on in vivo angiogenesis was demonstrated as explained below.

Figure 50A:
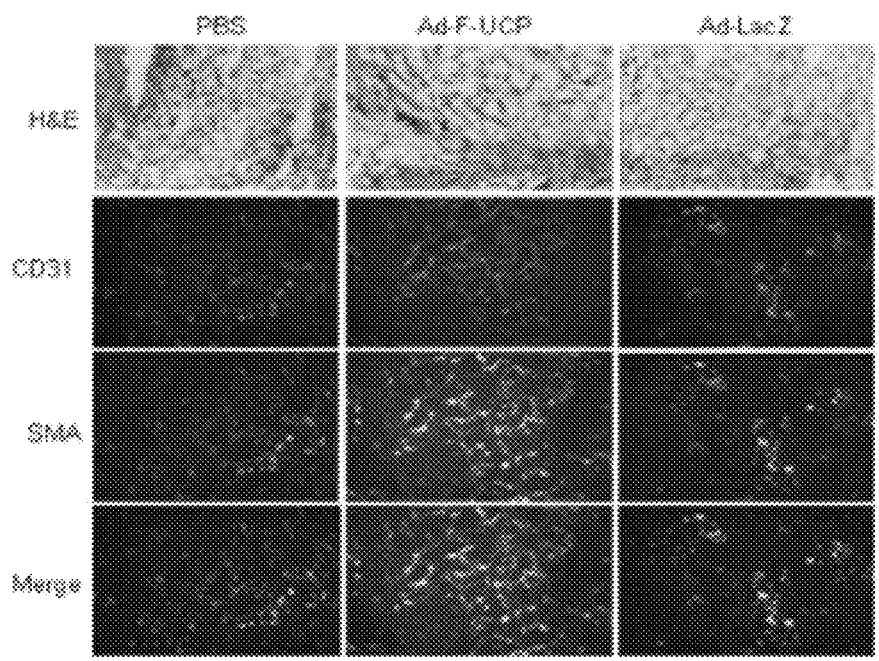
FIG. 50a is a hematoxylin & eosin (H&E) stained photograph illustrating that when NIH3T3 cells with UCP over-expression are mixed with Matrigel and then transplanted into mouse subcutaneously, vascular cells' invasion and proliferation into Matrigel increase, and immuno-fluorescent photographs acquired by using vascular cell marker CD31 (PEACAM-1) or SMA antibodies, which illustrate that UCP expression promotes mature blood vessel formation.
Figure 50B:
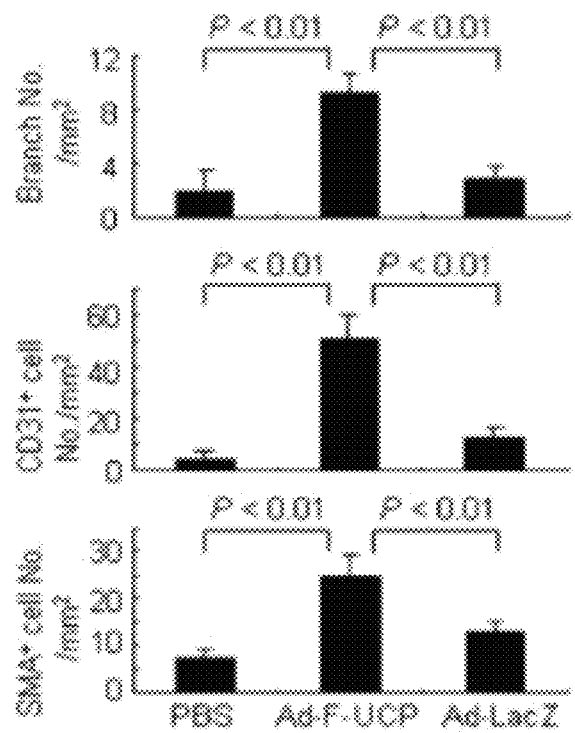

<14-1> Demonstrating UCP-Mediated Neo-Vascularization in Mouse by In Vivo Matrigel Plug Assay In order to investigate effect of the increased expression of angiogenesis-related factors by UCP in vivo, NIH3T3 cells were infected with or without Ad-F-UCP or Ad-LacZ virus at an MOI of 200. After 24 hours, the cells were mixed with Matrigel (500 μl), and the mixtures were subcutaneously injected in the right abdominal surface of mouse (BALb/c, 8-10 week, male). Five days after injection, the plug was removed and frozen in OCT compound for immunohistochemistry or fixed with 10% formalin for H&E staining. Frozen sections of 5 to 7 μm of the plug were immuno-stained with specific antibodies to CD31 (PECAM-1) and SMA, which are markers of mature blood vessel (FIG. 50a). Branch number of blood vessels, and CD31-positive and SMA-positive cells were counted from 5 randomly chosen fields and expressed quantitatively (FIG. 50b). As a result, the case of introducing Ad-F-UCP exhibited significant increase of blood vessel, CD31 or SMA-stained cells, compared to the control group. The results suggest that the expression-secreted angiogenesis-related factors by UCP-over-expression induced generation of vascular endothelial cells and smooth muscle cells, which are the building blocks for the blood vessels, and thereby promoting in vivo neovascularization.

Figure 50C:
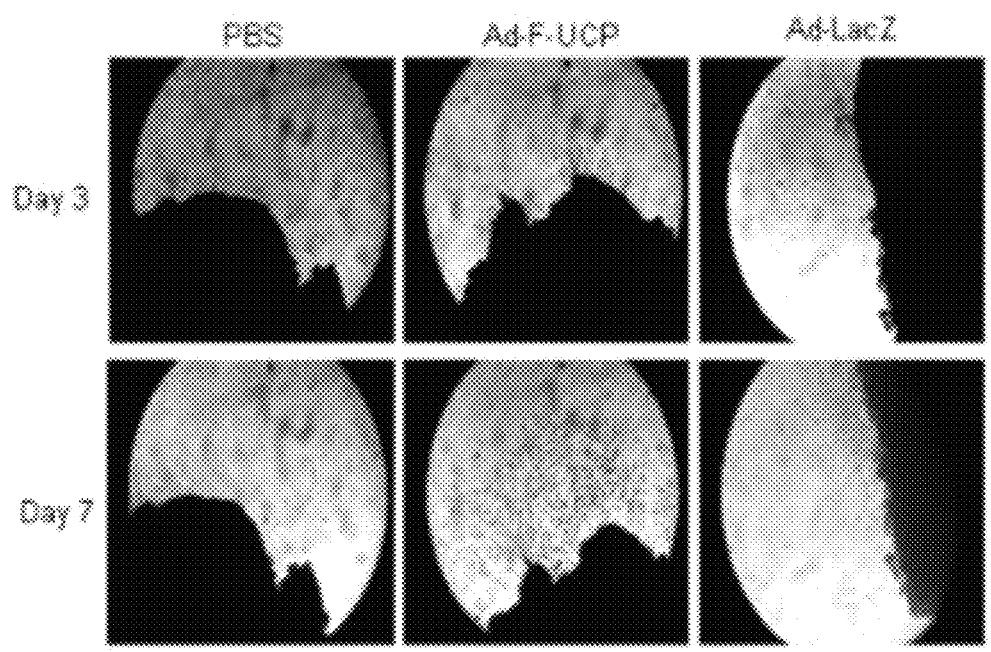
FIG. 50c is a photograph illustrating the promotion of capillary network formation observed after infecting mouse muscle with Ad-F-UCP, wherein the muscle tissues were removed after 3 days, then mixing the removed tissues with Matrigel and cultivating the same for 7 days.

<14-2> Demonstrating UCP-Mediated Neo-Vascularization in Mouse by Ex Vivo Angiogenesis Assay In order to test the effect of UCP on in vivo angiogenesis, PBS, Ad-F-UCP, or Ad-LacZ viruses were injected into hindlimb muscle of mouse by $2 \times 10^8$ plaque-forming-unit (PFU). Three days after adenoviral infection, the muscles were excised and were cut in the middle to expose the injection area and washed three times in PBS. The washed muscles were placed in a 24-well plate containing 250 µl of Matrigel and incubated at 37° C. for 30 min to solidify the gel. The plate was then covered with 500 µl of DMEM containing 5% FBS and 100 U/ml penicillin plus streptomycin. The plate was cultured at 37° C. under 5% $CO_2$. Outgrowth of capillary-like structures was observed in muscles with an inverted microscope at day 3 and day 7 after cultivation. As a result, it was demonstrated that sprouting of blood vessels from the muscle tissues injected with Ad-F-UCP virus noticeably increased at day 7, compared to the control group (PBS or Ad-LacZ) (FIG. 50c).

Figure 50D:
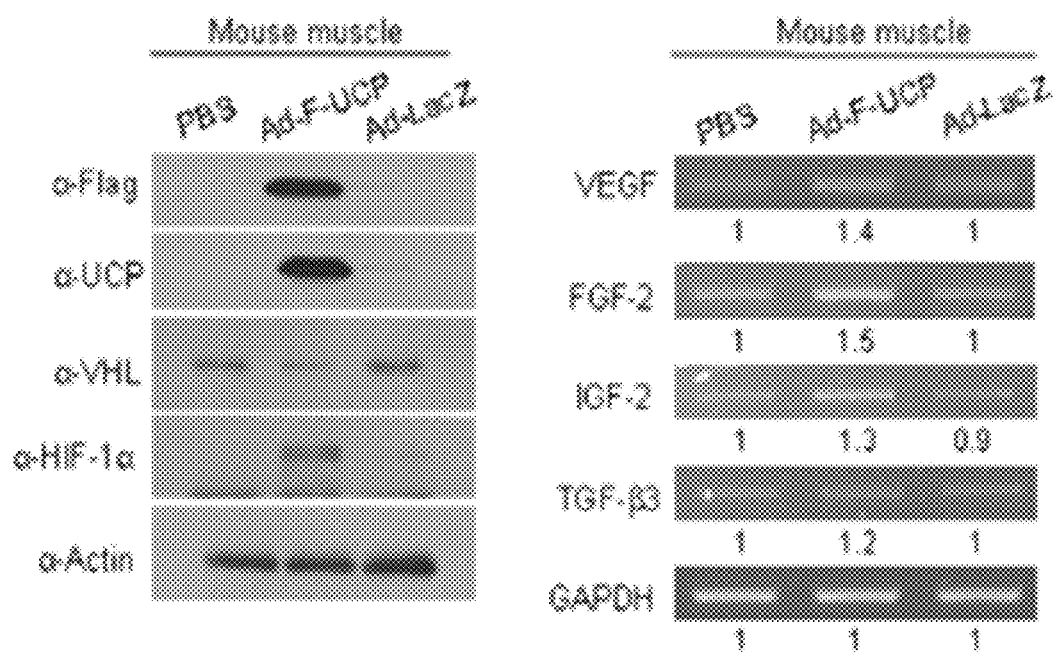
FIG. 50d is western blotting (left) and RT-PCR (right) photographs illustrating the increased expression of angiogenesis-related factors as the VHL-HIF pathway is controlled via UCP expression in mouse muscle tissue after Ad-F-UCP is injected.

<14-3> UCP Induces Expression of Angiogenesis-Related Factors in Mouse Muscle Tissue In order to examine if UCP would be actually expressed in the mouse muscle tissue injected with Ad-F-UCP (Embodiment <14-2>) and the VHL-HIF pathway would be regulated by the UCP over-expression, and if the expression of the angiogenesis-related factors would be actually increased, protein and the total RNA were extracted from the mouse hindlimb muscle tissues which were injected with PBS, Ad-F-UCP or Ad-LacZ virus. As a result of analyzing the extracted protein by the Western blotting, UCP was detected only when Ad-F-UCP was injected, and while the VHL level was decreased compared to the control group, higher HIF1α was observed (FIG. 50d, left panels). This result suggests that the VHL-HIF pathway is regulated by UCP in vivo. RT-PCR was conducted with total RNAs extracted from the muscle tissue as a template and specific primers for VEGF, FGF-2, IGF-2, and TGF-β3, respectively. As a result, it was demonstrated that the tissue injected with Ad-F-UCP exhibited increase of mRNA of VEGF and FGF-2, compared to the control group (PBS or Ad-LacZ) (FIG. 50d, right panels). This result implies that the HIF1a stabilization caused by the UCP over-expression can increase the expression of angiogenesis-related factors in vivo, such as VEGF and FGF-2, thereby stimulating angiogenesis.

Example 15

Demonstrating UCP-Mediated Angiogenesis by CAM Assay

Stimulation of in vivo angiogenesis by UCP was demonstrated using chicken chorioallantoic membrane (CAM) assay as follows. Fertilized chicken eggs were purchased from Korean poultry TS Company, and eggs were used within two days of laying. Only the eggs, confirmed as the fertilized ones, were used. HeLa cells were infected with or without Ad-F-UCP or Ad-LacZ (100 MOI each), and only the culture media was collected after 48 hours and concentrated by 50 times. Cover glasses were coated with 10 µl of the enriched media, dried, and put on the CAM of fertilized eggs that had been pre-incubated for 3 days. Seven days later, the CAM was cut out, and photographed under a microscope. Degree of angiogenesis was quantified by counting the number of branch points from which at least 3 blood vessels were branched (FIG. 51). As a result, it was demonstrated that the culture media from HeLa cells infected with Ad-F-UCP had about four times greater effect of stimulating angiogenesis of the fertilized chicken eggs, compared to the control group.

Example 16

UCP Induces Therapeutic Angiogenesis in a Mouse Model of Hindlimb Ischemia

From the embodiments explained above, it has been shown that the increasing UCP expression is related to the increase of expression of the angiogenesis-related factors via the VHL-HIF pathway, and thereby induces angiogenesis in vivo. In order to demonstrate the possibility of using UCP gene for the treatment of the diseases of peripheral blood vessel and coronary arteries, Ad-F-UCP virus was injected into the thigh muscle of mouse ischemic hindlimb, and the degree of vessel formation and treatment outcome were assessed as explained in detail below. The mouse hindlimb ischemic model was prepared by tying aorta of one limb with silk thread and tying second time immediately therebelow, and cutting in between the two places as tied. 6-10 mice were used per experimental group and experiment repeated more than 5 times to examine the ischemic treatment effect.

<16-1> Therapeutic Effect of UCP Gene Transfer in Ischemic Hindlimb Model

Figure 52A:
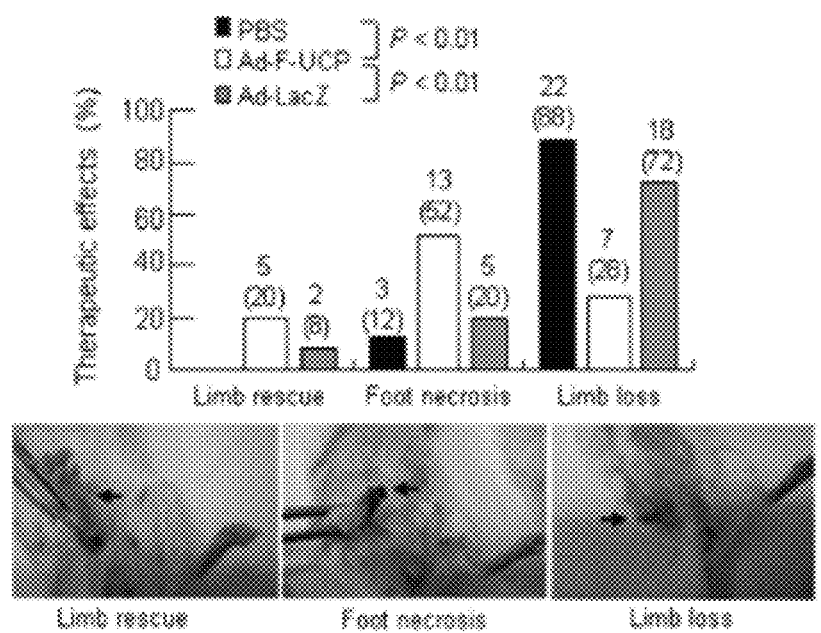
FIG. 52a is a phenotypic photograph of hindlimb illustrating level of recovery or necrosis comparing Ad-F-UCP injection group and control groups of the mouse hindlimb ischemia model as produced, photographs illustrating quantitatively degree of recovery or progress of mouse hindlimb ischemia in each experiment group (N=25) based on the phenotype.

Twenty-four hours after preparing ischemic hindlimb of mouse (N=25/experimental group), PBS or Ad-F-UCP, Ad-LacZ virus ($2 \times 10^9$ PFU) was injected into four sites of the operated leg (OL) once for each, and the recovery and necrosis of the ischemia-induced hindlimb were evaluated on the 21st day thereafter. The treatment effect of UCP was measured based on the categories of: 'limb rescue' which exhibited the condition similar to that of non-operated leg (NOL) (i.e., leg in which ischemia was not induced) and thus exhibited almost no loss of hindlimb; 'foot necrosis' which showed loss of foot but not knee; and 'limb loss' which showed complete loss of the hindlimb (FIG. 52a, bottom). While 88% (N=22) and 72% (N=18) of the mice of the control group injected with PBS and Ad-LacZ showed ischemic loss of the hindlimb, only 28% (N=7) of the mice injected with Ad-F-UCP showed loss of limb. Also, 20% (N=5) of the ischemia-induced mice treated with Ad-F-UCP showed recovery, and 52% (N=13) showed foot necrosis. Ad-LacZ cases exhibited 8% (N=2) of recovery of the hindlimb, and 20% (N=5) of foot necrosis. In the case of injecting only the PBS, none had recovery, and 12% (N=3) had foot necrosis. The differences in therapeutic effect between the Ad-F-UCP group and the control groups (Ad-LacZ or PBS) were significant. The above results indicate that UCP is effective for the treatment of ischemic diseases.

Figure 52B:
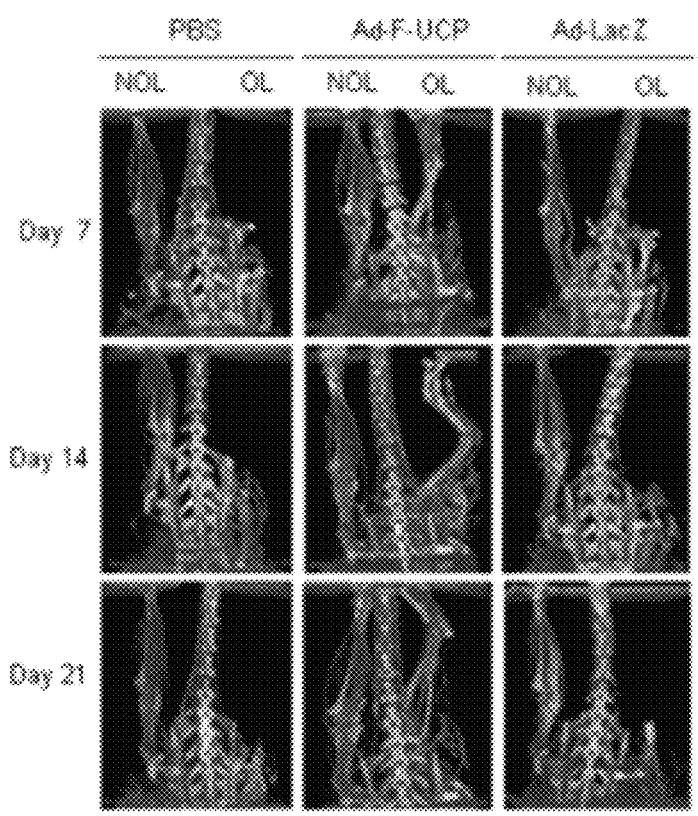
FIG. 52b is micro-CT photographs showing progress or overcoming of the hindlimb necrosis at one week intervals starting from the seventh day after injecting Ad-F-UCP virus.

In order to demonstrate the angiogenesis effect in the mouse hindlimb ischemic model through image, the case of recovery of the ischemia-induced limb by the injection of Ad-F-UCP was imaged using micro-CT (NANO-FOCUS-RAY) on the 7th, 14th and 21st days after injection. The contrast agent (fenestra VC, 400 µl/BALb/c 20-25 g) was injected into vein of the mouse tail, had the mouse go under inhalation anesthesia, and the blood vessels were imaged by micro-CT (FIG. 52b). As a result, it was demonstrated that the mouse, which was ischemia-induced and then recovered by the injection of Ad-F-UCP, had increased number of new capillaries (angiogenesis) compared to the limb in which vessels were not cut, and also the existent vessels were thickened (arteriogenesis) (FIG. 52b).

Figure 52C:
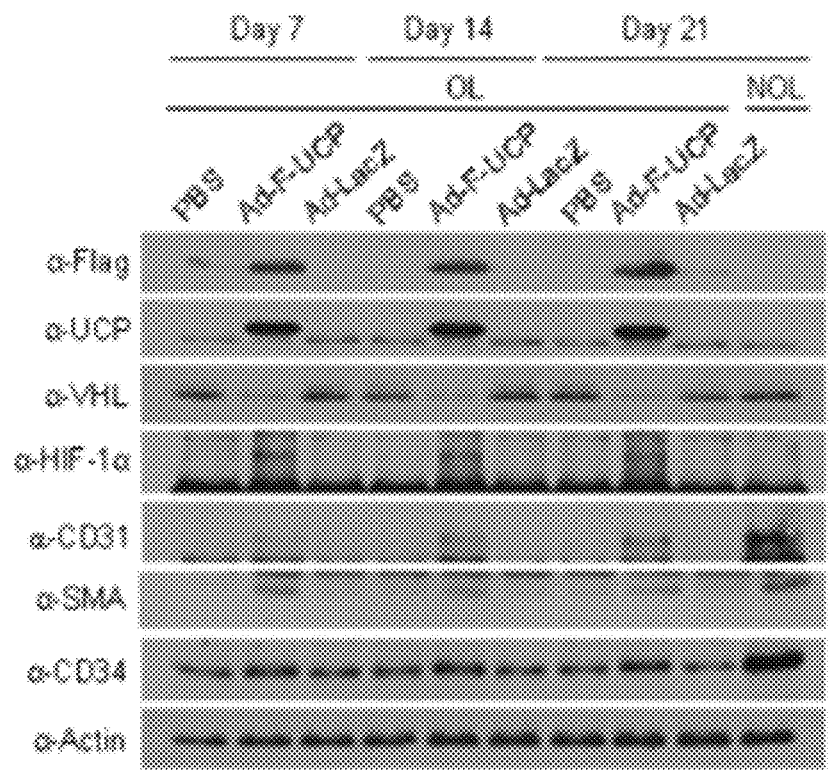
FIG. 52c is a western blotting result showing the UCP regulates the VHL-HIF1 pathway in ischemic hindlimb muscle tissue and thereby markers of mature blood vessel are increased.

<16-2> UCP Regulates the VHL-HIF-VEGF Pathway in Ischemic Hindlimb of Mouse and Promotes Formation of Mature Blood Vessel Mouse hindlimb ischemic model was prepared and after 24 hours, as explained above in Embodiment <16-1>, Ad-F-UCP, Ad-LacZ virus (2×10$^9$ PFU) was injected into the hindlimb ischemic site. On 7th, 14th and 21st days, protein extracts (OL) from the limb muscle tissue and protein extract (NOL) from the site without scission were analyzed by Western blotting (FIG. 52c). As a result, UCP expression was detected only in tissues injected with the Ad-F-UCP, the amount of VHL protein decreased, and HIF1α was detected, suggesting that UCP gene transfer occurred and UCP regulated the VHL-HIF1 pathway. The control group did not have endogenous UCP detected, and accordingly, relatively large amount of VHL was detected in the control group compared to Ad-F-UCP injected group, and HIF1α was barely detected. Furthermore, markers of mature blood vessel, CD31 and SMA, were markedly increased in Ad-F-UCP injected group compared to the control group (PBS or Ad-LacZ), although those levels appeared to be lower compared to the levels in non-operated leg (FIG. 52c). The effect of UCP gene transfer lasted by 21 days after the injection.

Figure 52D:
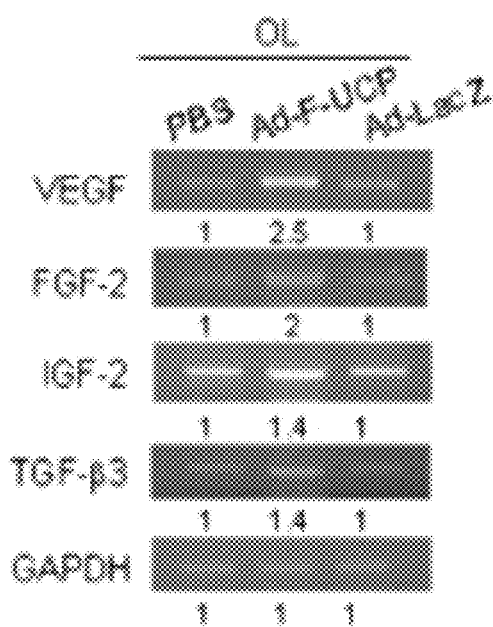
FIG. 52d is a RT-PCR photo illustrating when Ad-F-UCP is injected in ischemic hindlimb muscle tissue, expression of angiogenesis-related factors was increased compared to the control group.

On the 21st day after injecting Ad-F-UCP, total RNA was extracted from the muscle tissues and RT-PCR was conducted to determine if the expression of the angiogenesis related factors including VEGF, FGF-2, IGF-2, and TGF-63 increased (FIG. 52d). As a result, the Ad-F-UCP injected tissue showed increase of VEGF and FGF-2 mRNA levels by two times more than the control group (PBS or Ad-LacZ). Collectively, these results imply that UCP is expressed efficiently in the Ad-F-UCP injected tissue, thereby destabilizes VHL and stabilizes HIF1a, subsequently increases expression of the angiogenesis-related factors, and thereby promotes angiogenesis (FIG. 52d).

Figure 52E:
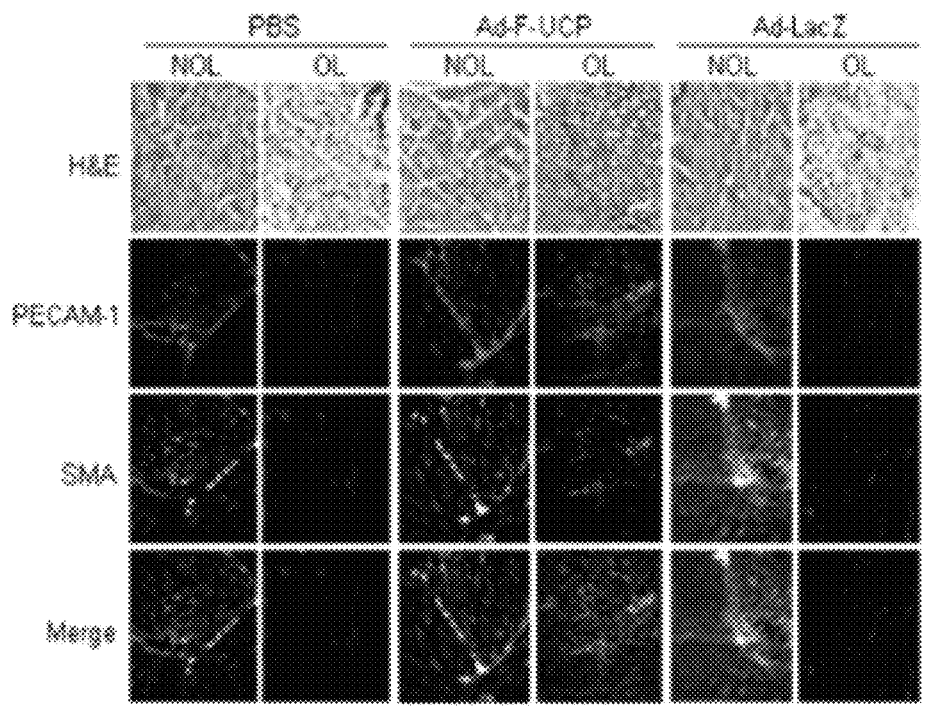
FIG. 52e is an H&E stain and immuno-fluorescent photographs of CD31 and SMA, showing that UCP increases formation of mature blood vessels in ischemic hindlimb tissue.
Figure 52F:
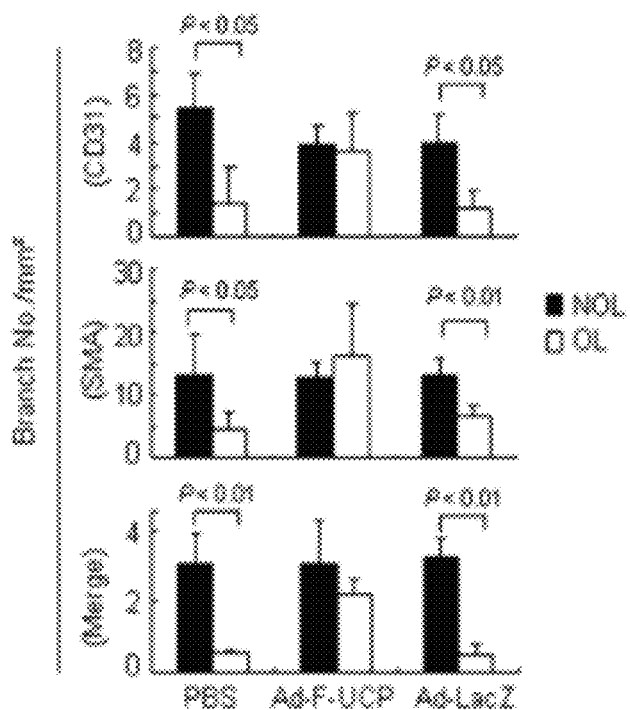
FIG. 52f is a graph quantitatively showing UCP increases formation of blood vessel in ischemic hindlimb tissue.

<16-3> UCP Promotes Generation of Mature Blood Vessel in Ischemic Hindlimb of Mouse In order to examine if UCP gene transfer results in efficient generation of blood vessel in the mouse hindlimb ischemic model, on the 21st day of injecting Ad-F-UCP or Ad-LacZ, frozen sections were prepared from the sites of the mouse with and without vessel scission, and stained with H&E method and CD31, SMA antibodies (FIG. 52e). H&E staining revealed massive muscle degeneration in the ischemic muscle with PBS or Ad-LacZ, but not with Ad-F-UCP (FIG. 5e). CD31-positive and SMA-positive cells, and double-positive cells (Merge) in immuno-fluorescent staining of the sections were assessed in five randomly chosen fields and quantified (FIG. 52f). As a result, with respect to the control group, the hindlimb tissue with ischemia (OL) had lower branch number than the hindlimb tissue without vessel scission (NOL), and not so many cells were stained with CD31, SMA antibodies. In the case of injecting Ad-F-UCP into ischemia-induced muscle tissue (OL), the muscle tissue had more branch number than the control group (PBS or Ad-LacZ), and significantly more cells were observed as being stained with CD31, SMA, as many as observed in the muscle tissue in which ischemia has not been induced. Moreover, most of CD31-positive cells were overlapped with SMA-positive cells in the muscle of the operated leg injected with Ad-F-UCP, suggesting efficient maturation of blood vessels by the UCP gene transfer.

These results suggest that F-UCP induces increased expression of angiogenesis inducing factors and generation of new blood vessels and thereby that damage caused by tissue ischemia can be significantly recovered by the UCP gene transfer.

INDUSTRIAL APPLICABILITY

As explained hereinbefore, UCP expression induces ubiquitination of VHL, a tumor suppressor protein, and thereby proteasome mediated VHL degradation, resulting in the stabilization of HIF-1α to increase active VEGF. Therefore, the inhibition of UCP activity or UCP depletion in cancer cells increases endogenous VHL, promotes HIF-1α degradation and thereby inhibits tumor growth and metastasis. Thus, the UCP activity inhibitor of the present invention can be used as an anticancer agent. UCP over-expression induces VHL degradation and HIF-1α stabilization, resulting in the increase of VEGF activity. Therefore, the UCP functionality can be effectively used for gene therapy for those patients who have to get dismemberment because of critical limb ischemia (CLI) caused by deficient blood vessels and who are suffering from inoperable coronary artery disease (CAD), dementia caused by insufficient blood supply, amyotrophic lateral sclerosis (ALS), diabetic neuropathy and stroke.

SEQUENCE LISTING

SEQ. ID. NO: 1 and NO: 2 are the forward and reverse primers for the construction of Flag-UCP, SEQ. ID. NO: 3 and NO: 4 are the forward and reverse primers for the construction of Flag-UCPm, SEQ. ID. NO: 5 is the sequence of UCP cDNA, SEQ. ID. NO: 6 is the DNA sequence expressing UCP-siRNA, SEQ. ID. NO: 7 is the DNA sequence expressing control-siRNA, SEQ. ID. NO: 8 and NO: 9 are the sense and antisense sequences of UCP mRNA (272-290), SEQ. ID. NO: 10 and NO: 11 are the sense and antisense sequences of Control siRNA, SEQ. ID. NO: 12 is the sequence of F-UCP (Silent Mutation), SEQ. ID. NO: 13 and NO: 14 are the primer sequences for confirming Flag-UCP, SEQ. ID. NO: 15 and NO: 16 are the primer sequences for confirming GFP, SEQ. ID. NO: 17 is the DNA sequence expressing GFP-siRNA, SEQ. ID. NO: 18 is the DNA sequence expressing HIF2 alpha-siRNA and SEQ. ID. NO:19 is the UCP-siRNA target sequence and SEQ. ID. NO:20 is a synonymous mutant variant of SEQ. ID. NO:19.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for stimulating angiogenesis in a subject, including the step of administering a pharmaceutically effective dosage of an expression vector with the insertion of an E2-Endemic pemphigus foliaceus Ubiquitin Carrier Protein (E2-EPF UCP) gene, or an E2-EPF UCP protein to the subject.

2. The method according to claim 1, wherein the E2-EPF UCP gene or the E2-EPF UCP protein reduces Von Hippel-Lindau (VHL) activity or level.

3. The method according to claim 1, wherein the E2-EPF UCP gene or the E2-EPF UCP protein increases Hypoxia-inducible factor (HIF) stability.

4. The method according to claim 1, wherein the E2-EPF UCP gene or the E2-EPF UCP protein increases expression of angiogenesis factors.

5. The method according to claim 4, wherein the angiogenesis factor is a vascular endothelial growth factor (VEGF).

* * * * *

SEQUENCE LISTING

<160> NUMBER OF SEQ ID NOS: 20

<210> SEQ ID NO 1
<211> LENGTH: 31
<212> TYPE: DNA
<213> ORGANISM: Artificial Sequence
<220> FEATURE:
<223> OTHER INFORMATION: Synthetic construct: Flag-UCP primer

<400> SEQUENCE: 1
tccgcggccg catgaactcc aacgtggaga a                                31

<210> SEQ ID NO 2
<211> LENGTH: 29
<212> TYPE: DNA
<213> ORGANISM: Artificial Sequence
<220> FEATURE:
<223> OTHER INFORMATION: Synthetic construct: Flag-UCP primer

<400> SEQUENCE: 2
accggatccc tacagccgcc gcagcgccc                                   29

<210> SEQ ID NO 3
<211> LENGTH: 30
<212> TYPE: DNA
<213> ORGANISM: Artificial Sequence
<220> FEATURE:
<223> OTHER INFORMATION: Synthetic construct: Flag-UCP primer, internal
      sense primer

<400> SEQUENCE: 3
aaaggcgaga tcagcgtcaa cgtgctcaag                                  30

<210> SEQ ID NO 4
<211> LENGTH: 30
<212> TYPE: DNA
<213> ORGANISM: Artificial Sequence
<220> FEATURE:
<223> OTHER INFORMATION: Synthetic construct: Flag-UCPm, internal
      antisense

<400> SEQUENCE: 4
cttgagcacg ttgacgctga tctcgccatt                                  30

<210> SEQ ID NO 5
<211> LENGTH: 678
<212> TYPE: DNA
<213> ORGANISM: Artificial Sequence
<220> FEATURE:
<223> OTHER INFORMATION: Synthetic construct: UCP cDNA sequence

<400> SEQUENCE: 5
atgaactcca acgtggagaa cctaccccg cacatcatcc gcctggtgta caaggaggtg    60
acgacactga ccgcagaccc acccgatggc atcaaggtct ttcccaacga ggaggacctc   120
accgacctcc aggtcaccat cgagggccct gaggggaccc catatgctgg aggtctgttc   180
cgcatgaaac tcctgctggg gaaggacttc cctgcctccc cacccaaggg ctacttcctg   240
accaagatct ccacccgaa cgtgggcgcc aatggcgaga tctgcgtcaa cgtgctcaag   300
agggactgga cggctgagct gggcatccga cacgtactgc tgaccatcaa gtgcctgctg   360
atccacccta accccgagtc tgcactcaac gaggaggcgg ccgcctgct cttggagaac   420 tacgaggagt atgcggctcg ggcccgtctg ctcacagaga tccacggggg cgccggcggg   480
cccagcggca gggccgaagc cggtcgggcc ctggccagtg gcactgaagc ttcctccacc   540

```
gaccctgggg ccccaggggg cccgggaggg gctgagggtc ccatggccaa gaagcatgct      600
ggcgagcgcg ataagaagct ggcggccaag aaaaagacgg acaagaagcg ggcgctgcgg      660
gcgctgcggc ggctgtag                                                    678
```

<210> SEQ ID NO 6
<211> LENGTH: 52
<212> TYPE: DNA
<213> ORGANISM: Artificial Sequence
<220> FEATURE:
<223> OTHER INFORMATION: Synthetic construct: DNA sequence expressing
      UCP-siRNA

<400> SEQUENCE: 6

```
gaagctggcg gccaagaaat tcaagagatt tcttggccgc agcttctttt tt             52
```

<210> SEQ ID NO 7
<211> LENGTH: 52
<212> TYPE: DNA
<213> ORGANISM: Artificial Sequence
<220> FEATURE:
<223> OTHER INFORMATION: Synthetic construct: DNA sequence expressing
      control-siRNA

<400> SEQUENCE: 7

```
gctcaccctg aaattcatct tcaagagaga tgaatttcag ggtgagcttt tt             52
```

<210> SEQ ID NO 8
<211> LENGTH: 21
<212> TYPE: DNA
<213> ORGANISM: Artificial Sequence
<220> FEATURE:
<223> OTHER INFORMATION: Synthetic construct: UCP mRNA (272-290, sense)

<400> SEQUENCE: 8

```
auggcgagau cugcgucaat t                                                21
```

<210> SEQ ID NO 9
<211> LENGTH: 21
<212> TYPE: DNA
<213> ORGANISM: Artificial Sequence
<220> FEATURE:
<223> OTHER INFORMATION: Synthetic construct: UCP mRNA (272-290,
      antisense)

<400> SEQUENCE: 9

```
uugacgcaga ucucgccaut t                                                21
```

<210> SEQ ID NO 10
<211> LENGTH: 21
<212> TYPE: DNA
<213> ORGANISM: Artificial Sequence
<220> FEATURE:
<223> OTHER INFORMATION: Synthetic construct: Control siRNA, sense

<400> SEQUENCE: 10

```
aaggagacga gcaagagaat t                                                21
```

<210> SEQ ID NO 11
<211> LENGTH: 21
<212> TYPE: DNA
<213> ORGANISM: Artificial Sequence
<220> FEATURE:
<223> OTHER INFORMATION: Synthetic construct: Control siRNA, antisense

<400> SEQUENCE: 11

```
uucucuugcu cgucuccuut t                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic construct:   F-UCP (Silent Mutation)

<400> SEQUENCE: 12
aaaaaattag cagctaaaaa g                                              21

<210> SEQ ID NO 13
<211> LENGTH: 20
<212> TYPE: DNA
<213> ORGANISM: Artificial Sequence
<220> FEATURE:
<223> OTHER INFORMATION: Synthetic construct:   Flag/UCP confirmation
      primer

<400> SEQUENCE: 13
atgaactcca acgtggagaa                                                20

<210> SEQ ID NO 14
<211> LENGTH: 18
<212> TYPE: DNA
<213> ORGANISM: Artificial Sequence
<220> FEATURE:
<223> OTHER INFORMATION: Synthetic construct:   Flag/ UCP confirmation
      primer

<400> SEQUENCE: 14
ctacagccgc cgcagcgc                                                  18

<210> SEQ ID NO 15
<211> LENGTH: 19
<212> TYPE: DNA
<213> ORGANISM: Artificial Sequence
<220> FEATURE:
<223> OTHER INFORMATION: Synthetic construct:   GFP confirmation primer

<400> SEQUENCE: 15
aaggagaaaa cttttcact                                                 19

<210> SEQ ID NO 16
<211> LENGTH: 20
<212> TYPE: DNA
<213> ORGANISM: Artificial Sequence
<220> FEATURE:
<223> OTHER INFORMATION: Synthetic construct:   GFP confirmation primer

<400> SEQUENCE: 16
taatggtctg ctagttgaac                                                20

<210> SEQ ID NO 17
<211> LENGTH: 52
<212> TYPE: DNA
<213> ORGANISM: Artificial Sequence
<220> FEATURE:
<223> OTHER INFORMATION: Synthetic construct:   DNA sequence expressing
      GFP-siRNA

<400> SEQUENCE: 17
gctcaccctg aaattcatct tcaagagaga tgaatttcag ggtgagcttt tt            52
```

-continued

```
<210> SEQ ID NO 18
<211> LENGTH: 52
<212> TYPE: DNA
<213> ORGANISM: Artificial Sequence
<220> FEATURE:
<223> OTHER INFORMATION: Synthetic construct:  DNA sequence expressing
      HIF2 alpha-siRNA

<400> SEQUENCE: 18
ggagacggag gtgttctatt tcaagagaat agaacacctc cgtctccttt tt           52

<210> SEQ ID NO 19
<211> LENGTH: 21
<212> TYPE: DNA
<213> ORGANISM: Artificial Sequence
<220> FEATURE:
<223> OTHER INFORMATION: Synthetic construct:  UCP siRNA target sequence

<400> SEQUENCE: 19
aagaagctgg cggccaagaa a                                              21

<210> SEQ ID NO 20
<211> LENGTH: 21
<212> TYPE: DNA
<213> ORGANISM: Artificial Sequence
<220> FEATURE:
<223> OTHER INFORMATION: Synthetic construct:  variant UCP siRNA target
      sequence

<400> SEQUENCE: 20
aaaaaattag cagctaaaaa g                                              21
```